US009783576B2

(12) United States Patent
Fukuda et al.

(10) Patent No.: US 9,783,576 B2
(45) Date of Patent: Oct. 10, 2017

(54) COMPOSITIONS AND METHODS FOR TARGETED ENDOMETRIOSIS TREATMENT

(71) Applicant: Sanford-Burnham Medical Research Institute, La Jolla, CA (US)

(72) Inventors: Michiko Fukuda, La Jolla, CA (US); Kazuhiro Sugihara, Hamamatsu (JP)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 14/897,757

(22) PCT Filed: Jun. 11, 2014

(86) PCT No.: PCT/US2014/041912
§ 371 (c)(1),
(2) Date: Dec. 11, 2015

(87) PCT Pub. No.: WO2014/201118
PCT Pub. Date: Dec. 18, 2014

(65) Prior Publication Data
US 2016/0145308 A1    May 26, 2016

Related U.S. Application Data

(60) Provisional application No. 61/833,519, filed on Jun. 11, 2013.

(51) Int. Cl.

| A61K 45/06 | (2006.01) |
| C07K 7/08 | (2006.01) |
| C07K 14/47 | (2006.01) |
| A61K 38/08 | (2006.01) |
| A61K 38/10 | (2006.01) |
| C07K 16/28 | (2006.01) |

(52) U.S. Cl.
CPC .............. *C07K 7/08* (2013.01); *A61K 38/08* (2013.01); *A61K 38/10* (2013.01); *A61K 45/06* (2013.01); *C07K 14/4747* (2013.01); *C07K 16/28* (2013.01); *C07K 2319/03* (2013.01); *C07K 2319/70* (2013.01)

(58) Field of Classification Search
None
See application file for complete search history.

(56) References Cited

FOREIGN PATENT DOCUMENTS

| WO | 02096928 | 12/2005 |
| WO | 2007076501 | 7/2007 |
| WO | 2012013326 | 2/2012 |

OTHER PUBLICATIONS

Amsterdam, et al., "Anastrazole and oral contraceptives: a novel treatment for endometriosis", Fertil Steril., 84:300-4 (2005).

Aoki, et al., "Successful heterotransplantation of human endometrium in SCID mice", Obstet Gynecol., 83:220-8 (1994).
Aplin, et al., "Human endometrial MUC1 carries keratan sulfate: characteristic glycoforms in the luminal epithelium at receptivity", Glycobiology, 8:269-76 (1998).
Arap, et al., "Cancer treatment by targeted drug delivery to tumor vasculature in a mouse model", Science, 279:377-80 (1998).
Arici, et al., "Increased pregnancy-associated plasma protein-A (PAPP-A) concentrations in peritoneal fluid of women with endometriosis", Am J Reprod Immunol., 49:70-4 (2003).
Arimoto, et al., "Genome-wide cDNA microarray analysis of gene-expression profiles involved in ovarian endometriosis", Int J Oncol., 22:551-60 (2003).
Awwad, et al., "The SCID mouse: an experimental model for endometriosis", Hum Reprod., 14:3107-11 (1999).
Barbieri and Missmer, "Endometriosis and infertility: a cause-effect relationship?", Ann N Y Acad Sci., 955:23-33; discussion 34-6, 396-406 (2002).
Barbieri, "New therapy for endometriosis", N Engl J Med., 318:512-4 (1998).
Beck, et al., Adenosine 3',5'-monophosphate mediates progesterone effect on sulfate uptake in endometrial epithelial cells!, Endocrinology, 136:1737-43 (1995).
Beliard, et al., "Reduction of apoptosis and proliferation in endometriosis", Fertil Steril., 82: 80-85 (2004).
Brodzik, et al., "Plant-derived anti-Lewis Y mAb exhibits biological activities for efficient immunotherapy against human cancer cells", PNAS, 103:8804-9 (2006).
Castillo, et al., "Newer monoclonal antibodies for hematological malignancies", Exp Hematol., 36:755-768 (2008).
Clayton, et al., "Structural basis of ligand activation in a cyclic nucleotide regulated potassium channel", Cell, 119:615-27 (2004).
Cramer, et al., "The epidemiology of endometriosis", Ann N Y Acad Sci., 955:11-22; discussion 34-6, 396-406 (2002).
Das, et al., "Cannabinoid ligand-receptor signaling in the mouse uterus", PNAS, 92:4332-6 (1995).
De Maria, et al., "Requirement for GD3 ganglioside in CD95- and ceramide-induced apoptosis", Science, 277:1652-5 (1997).
del Rio, et al., "APAP, a sequence-pattern-recognition approach identifies substance P as a potential apoptotic peptide", FEBS Lett., 494:213-9 (2001).
Dimasi, et al., "Trends in risks associated with new drug development: success rates for investigational drugs", Clin Pharmacol Ther., 87: 272-7 (2010).
Dmowski, et al., "Apoptosis in endometrial glandular and stromal cells in women with and without endometriosis", Hum Reprod., 16:1802-8 (2001).
Eisenhardt, et al., "Subtractive single-chain antibody (scFv) phage-display: tailoring phage-display for high specificity against function-specific conformations of cell membrane molecules", Nat Protoc., 2:3063-73 (2007).
Ellerby, et al., "Anti-cancer activity of targeted pro-apoptotic peptides", Nat Med., 5:1032-8 (1999).

(Continued)

*Primary Examiner* — Thomas S Heard
(74) *Attorney, Agent, or Firm* — Pabst Patent Group LLP

(57) ABSTRACT

Disclosed are compositions and methods for selectively targeting an endometriosis cell. Also disclosed are compositions and methods for treating endometriosis.

51 Claims, 4 Drawing Sheets

(56) References Cited

OTHER PUBLICATIONS

Eyster, wt al., "DNA microarray analysis of gene expression markers of endometriosis", Fertil Steril., 77:38-42 (2002).
Fantin, et al., "A bifunctional targeted peptide that blocks NER02 tyrosine kinase and disables mitochondrial function in HER-2positive carcinoma cells", pp. 6891-6900,http://cancerres.aacrjournals.org/content/65/16/6891.full.pdf#page.1&view=FitH,Retrieved from the Internet Sep. 15, 2014.
Farquhar, "Extracts from the clinical evidence Endometriosis". BMJ, 320:1449-52 (2000).
Fukuda, et al., "Trophinin and tastin, a novel cell adhesion molecule complex with potential involvement in embryo implantation", Genes Dev., 9:1199-210 (1995).
Fukuda, et al., "A peptide mimic of E-selectin ligand inhibits sialyl Lewis X-dependent lung colonization of tumor cells", Cancer Res., 60:450-6 (2000).
Gerlag, et al., "Suppression of murine collagen-Induced arthritis by targeted apoptosis of synovial neovasculature", Arthritis Res., 3:357-61(2001).
Giudice and Kao, "Endometriosis", Lancet, 364:1789-99 (2004).
Grummer, et al., "Peritoneal endometriosis: validation of an in-vivo model", Hum Reprod., 16:1736-43 (2001).
Haffner, et al., "Two decades of orphan product development", Nat Rev Drug Discov., 1:821-5 (2002).
Hayes and Rock, "Cox-2 inhibitors and their role in gynecology", Obstet Gynecol Surv., 57:768-80 (2002).
Houston, "Evidence for the risk of pelvic endometriosis by age, race and socioeconomic status", Epidemiol Rev., 6:167-91 (1984).
Iwamori, et al., "Monoclonal antibody-defined antigen of human uterine endometrial carcinomas is Leb", J Biochem., 105:718-22 (1998).
Johnson and Farquhar, "Endometriosis", Clin Evid., 2449-64 (2006).
Jones, et al., "Computer programs to identify and classify amphipathic alpha helical domains", J Lipid Res 33:287-96 (1992).
Kao, et al., "Expresilon profiling of endometrium from women with endometriosis reveals candidate genes for disease-based implantation failure and infertility", Endocrinology, 144:2870-81(2003).
Kessler, et al., "Cannabinoid receptor I activation markedly inhibits human decidualization", Mol Cell Endocrinol., 229:65-74 (2005).
Kolonin, et al., "Reversal of obesity by targeted ablation of adipose tissue", Nat Med., 10: 625-32 (2004).
Laakkonen, et al., "Antitumor activity of a homing peptide that targets tumor lymphatics and tumor cells", PNAS, 101(25):9381-6 (2004).
Lessey, et al., "Integrin adhesion molecules in the human endometrium. Correlation with the normal and abnormal menstrual cycle", J Clin.Invest., 90:188-95 (1992).
Malisan and Testi, "GD3 ganglioside and apoptosis", Biochim Biophys Acta, 1585:179-87, (2002).
Martin and Rice, "Peptide-guided gene delivery", Aaps J, 9(1): E18-29. (2007).
Matsuzaki, et al., "Differential expression of genes in eutopic and ectopic endometrium from patients with ovarian endometriosis", Fertil Steril., 86:548-53 (2006).
Matsuzaki, et al., "DNA microarray analysis of gene expression profiles in deep endometriosis using laser capture microdissection", Mol Hum Reprod., 10:719-28 (2004).
Midoux, et al., "Histidine containing peptides and polypeptides as nucleic acid vectors", Somat Cell Mol Genet., 27:27-47 (2002).
Moutsatsou and Sekeris, "Estrogen and progesterone receptors in the endometrium", Ann N Y Acad Sci., 816:99-115 (1997).
Murphy, "Clinical aspects of endometriosis", Ann N Y Acad Sci., 955:1-10; discussion 34-16, 396-406 (2002).
Murphy, et al., "Unsuspected endometriosis documented by scanning electron microscopy in visually normal peritoneum", Fertil Steril., 46:522-4 (1986).
Nisolle, et al., "Immunohistochemical analysis of proliferative activity and steroid receptor expression in peritoneal and ovarian endometriosis", Fertil Steril., 68:912-9 (1997).
Okada, et al., "Functional role of hCngb3 in regulation of human cone cng channel: effect of rod monochromacy-associated mutations in hCNGB3 on channel function", Invest Ophthalmol Vis Sci., 45:2324-32 (2004).
Oku, et al., "Anti-neovascular therapy using novel peptides homing to angiogenic vessels", Oncogene, 21:2662-9 (2002).
Oku et al., "Therapeutic effect of adriamycin encapsulated in long-circulating liposomes on Meth-A-sarcoma-bearing mice", Int J Cancer, 58:415-9 (1994).
Olive and Pritts, "Treatment of endometriosis", N Engl J Med., 345: 266-75 (2001).
O'Mahony and Bishop, "Monoclonal antibody therapy", Front Biosci., 11:1620-35 (2006).
Pan, et al., "The expression profile of micro-RNA in endometrium and endometriosis and the influence of ovarian steroids on their expression", Mol Hum Reprod., 13:797-806 (2007).
Pasqualini and Ruoslahti, "Organ targeting in vivo using phage display peptide libraries", Nature, 380:364-6 (1996).
Pasqualini, et al., "Aminopeptidase N is a receptor for tumor-homing peptides and a target for inhibiting angiogenesis", Cancer Res., 60:722-7 (2000).
Peng,et al., "Achromatopsia-associated mutation in the human cone photoreceptor cyclic nucleotide-gated channel CNGB3 subunit alters the ligand sensitivity and pore properties of heteromeric channels", J Biol Chem., 278; 34533-40 (2003).
Pichon, et al., "Histidine-rich peptides and polymers for nucleic acids delivery", Adv Drug Deliv Rev., 53:75-94 (2001).
Rajotte and Ruoslahti, "Membrane dipeptidase is the receptor for a lung-targeting peptide identified by in vivo phage display", J.Biol. Chem., 274, 11593-8 (1999).
Rajotte, et al., "Molecular heterogeneity of the vascular endothelium revealed by in vivo phage display", J Clin Invest 102, 430-437 (1998).
Rasmussen, et al., "Tumor cell-targeting by phage-displayed peptides", Cancer Gene Ther., 9:606-12 (2002).
Rier, et al., "Endometriosis in rhesus monkeys (*Macaca mulatta*) following chronic exposure to 2,3,7,8-tetrachlorodibenzo-p-dioxin", Fundam Appl Toxicol., 21: 433-41 (1993).
Rier, et al., "Serum levels of TCDD and dioxin-like chemicals in Rhesus monkeys chronically exposed to dioxin: correlation of increased serum PCB levels with endometriosis", Toxicol Sci., 59:147-59 (2001).
Ruoslahti, "Targeting tumor vasculature with homing peptides from phage display", Semin Cancer Biol., 10:435-42 (2000).
Ruoslahti, "Drug targeting to specific vascular sites", Drug Discov Today, 7:1138-43 (2002).
Sensky and Liu, "Endometriosis: associations with menorrhagia, infertility and oral contraceptives", Int J Gynaecol Obstet., 17:573-6 (1980).
Shampson, "The development of the implantation theory for the origin of peritoneal endometriosis", Am. J. Obstet. Gynecol., 40:549-57 (1940).
Sherwin, et al., "Global gene analysis of late secretory phase, eutopic endometrium does not provide the basis for a minimally invasive test of endometriosis", Hum Reprod., 23:1063-8 (2008).
Smith, "Filamentous fusion phage: novel expression vectors that display cloned antigens on the virion surface", Science, 228:1315-7 (1985).
Stausbol-Gron, et al., "A model phage display subtraction method with potential for analysis of differential gene expression", FEBS Lett., 391:71-5 (1996).
Stavreus-Evers, et al., "Formation of pinopodes in human endometrium is associated with the concentrations of progesterone and progesterone receptors", Fertil Steril., 76:782-91 (2001).
Sugihara, et al., "Trophoblast cell activation by trophinin ligation is implicated in human embryo implantation", PNAS; :104:3799-804 (2007).
Thomas and Campbell, "Evidence that endometriosis behaves in a malignant manner", Gynecol Obstet Invest., 50 Suppl 1; 2-10:(2000).

(56) References Cited

OTHER PUBLICATIONS

Torchilin, et al., "TAT peptide on the surface of liposomes affords their efficient intracellular delivery even at low temperature and in the presence of metabolic inhibitors", PNAS, 98;8786-91 (2001).

Traish and Wotiz, "Monoclonal and polyclonal antibodies to human progesterone receptor peptide-(533-547) recognize a specific site in unactivated (8S) and activated (4S) progesterone receptor and distinguish between intact and proteolyzed receptors", Endocrinology, 127:1167-75 (1550).

Van Ewijk, et al., "Subtractive isolation of phage-displayed single-chain antibodies to thymic stromal cells by using intact thymic fragments", PNAS, 94:3903-8 (1997).

Varkouhi, et al., "Endosomal escape pathways for delivery of biologicals", J Cont Release, 151(3):220-8 (2010).

Vercellini, et al., "Repetitive surgery for recurrent symptomatic endometriosis: what to do?" Eur J Obstet Gynecol Reprod Biol., 146:15-21 (2009).

Vercellini, et al., "Continuous use of an oral contraceptive for endometriosis-associated recurrent dysmenorrhea that does not respond to a cyclic pill regimen", Fertil Steril., 80:560-3 (2003).

Vetter, et al., "Na absorption across endometrial epithelial cells is stimulated by cAMP-dependent activation of an inwardly rectifying K channel", J Membr Biol., 160:119-26 (1997).

Vigano, et al., "Expression of intercellular adhesion molecule (ICAM)-1 mRNA and protein is enhanced in endometriosis versus endometrial stromal cells in culture", Mol Hum Reprod., 4:1150-6 (1998).

Vinatier, et al., "Theories of endometriosis", Eur J Obstet Gynecol Reprod Biol., 96:21-34 (2001).

Wender, et al., "The design, synthesis, and evaluation of molecules that enable or enhance cellular uptake: peptoid molecular transporters", PNAS, 97:13003-8 (2000).

Zafrakas, et al., "Genome-wide microarray gene expression, array-CGH analysis, and telomerase activity in advanced ovarian endometriosis: a high degree of differentiation rather than malignant potential", Int J Mol Med., 21:335-44 (2008).

Zhang, et al., "Neuroblastoma tumor cell-binding peptides identified through random peptide phage display", Cancer Lett., 171:153-64 (2001).

International Search Report for corresponding PCT/US2014/041912 mailed Feb. 10, 2015.

SEQUENCE LISTING

```
<160> NUMBER OF SEQ ID NOS: 171

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Val Arg Arg Ala Xaa Asn Xaa Pro Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Val Arg Arg Ala Asn Asn Leu Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Val Arg Arg Ala Asp Asn Arg Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Val Arg Arg Ala Asn Asn Arg Pro Gly
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Cys Arg Gly Met Ser Asp Thr Thr Ala Leu
1               5                   10
```

```
<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Cys Val Arg Arg Ala Asp Asn Arg Pro Gly
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Val Arg Ser Ser Arg Ser Thr Pro Gln
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Met Gln Arg Thr Arg Ala Thr Pro Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Arg Gly Met Ser Asp Thr Thr Ala Leu
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Arg Gln Pro Lys Ile Trp Phe Pro Asn Arg Arg Lys Pro Trp Lys Lys
1               5                   10                  15

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Gly Arg Lys Lys Arg Arg Gln Arg Pro Pro Gln
1               5                   10
```

```
<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Arg Gln Ile Ala Ile Trp Phe Gln Asn Arg Arg Met Lys Trp Ala Ala
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Arg Lys Lys Arg Arg Gln Arg Arg Arg
1               5

<210> SEQ ID NO 15
<211> LENGTH: 21
<212> TYPE: PRT
<213> ORGANISM: Artificial Sequence
<220> FEATURE:
<223> OTHER INFORMATION: Synthetic peptide

<400> SEQUENCE: 15

Thr Arg Ser Ser Arg Ala Gly Leu Gln Phe Pro Val Gly Arg Val His
1               5                   10                  15

Arg Leu Leu Arg Lys
            20

<210> SEQ ID NO 16
<211> LENGTH: 26
<212> TYPE: PRT
<213> ORGANISM: Artificial Sequence
<220> FEATURE:
<223> OTHER INFORMATION: Synthetic peptide

<400> SEQUENCE: 16

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 17
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 17

Lys Leu Ala Leu Lys Leu Ala Leu Lys Ala Leu Lys Ala Ala Leu Lys
1               5                   10                  15

Leu Ala

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide

<400> SEQUENCE: 18

Ala Ala Val Ala Leu Leu Pro Ala Val Leu Leu Ala Leu Leu Ala Pro
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Val Pro Met Leu Lys Pro Met Leu Lys Glu
1               5                   10

<210> SEQ ID NO 20
<211> LENGTH: 28
<212> TYPE: PRT
<213> ORGANISM: Artificial Sequence
<220> FEATURE:
<223> OTHER INFORMATION: Synthetic peptide

<400> SEQUENCE: 20

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide

<400> SEQUENCE: 21

Leu Leu Ile Ile Leu Arg Arg Arg Ile Arg Lys Gln Ala His Ala His
1               5                   10                  15

Ser Lys

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

Lys Glu Thr Trp Trp Glu Thr Trp Trp Thr Glu Trp Ser Gln Pro Lys
1               5                   10                  15

Lys Lys Arg Lys Val
            20
```

```
<210> SEQ ID NO 23
<211> LENGTH: 18
<212> TYPE: PRT
<213> ORGANISM: Artificial Sequence
<220> FEATURE:
<223> OTHER INFORMATION: Synthetic peptide

<400> SEQUENCE: 23

Arg Gly Gly Arg Leu Ser Tyr Ser Arg Arg Arg Phe Ser Thr Ser Thr
1               5                   10                  15

Gly Arg

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ser Asp Leu Trp Glu Met Met Val Ser Leu Ala Cys Gln Tyr
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide

<400> SEQUENCE: 25

Thr Ser Pro Leu Asn Ile His Asn Gly Gln Lys Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Lys Leu Ala Lys Leu Ala Lys Lys Leu Ala Lys Leu Ala Lys
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 27

Lys Leu Ala Lys Leu Ala Lys Lys Leu Ala Lys Leu Ala Lys Val Arg
1               5                   10                  15

Arg Ala Xaa Asn Xaa Pro Gly
            20
```

```
<210> SEQ ID NO 28
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 28

His Leu Ala His Leu Ala His His Leu Ala His Leu Ala His His Leu
1               5                   10                  15

Ala His Val Arg Arg Ala Xaa Asn Xaa Pro Gly
            20                  25

<210> SEQ ID NO 29
<211> LENGTH: 23
<212> TYPE: PRT
<213> ORGANISM: Artificial Sequence
<220> FEATURE:
<223> OTHER INFORMATION: Synthetic peptide

<400> SEQUENCE: 29

Lys Leu Ala Lys Leu Ala Lys Lys Leu Ala Lys Leu Ala Lys Val Arg
1               5                   10                  15

Arg Ala Asp Asn Arg Pro Gly
            20

<210> SEQ ID NO 30
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 30

His Leu Ala His Leu Ala His His Leu Ala His Leu Ala His His Leu
1               5                   10                  15

Ala His Lys Leu Ala Lys Leu Ala Lys Lys Leu Ala Lys Leu Ala Lys
            20                  25                  30

Lys Leu Ala Lys Val Arg Arg Ala Xaa Asn Xaa Pro Gly
            35                  40                  45

<210> SEQ ID NO 31
<211> LENGTH: 23
<212> TYPE: PRT
<213> ORGANISM: Artificial Sequence
<220> FEATURE:
<223> OTHER INFORMATION: Synthetic peptide
```

-continued

```
<400> SEQUENCE: 31

Lys Glu Asn Glu Asp Lys Gly Lys Glu Asn Glu Asp Lys Asp Lys Gly
1               5                   10                  15

Arg Glu Pro Glu Glu Lys Pro
            20

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Phe Val Arg Gly Gly Asp Ile Ile Val Asp Ser Asn Glu Leu
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Tyr Thr Trp Asp Ser Gln Arg Met Leu Asp Glu Ser Asp Leu
1               5                   10

<210> SEQ ID NO 34
<211> LENGTH: 809
<212> TYPE: PRT
<213> ORGANISM: Homo sapiens

<400> SEQUENCE: 34

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190
```

-continued

```
Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu
    210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
                260                 265                 270

Pro Arg Leu Gln Phe Val Arg Gly Gly Asp Ile Ile Val Asp Ser Asn
            275                 280                 285

Glu Leu Arg Lys His Tyr Arg Thr Ser Thr Lys Phe Gln Leu Asp Val
        290                 295                 300

Ala Ser Ile Ile Pro Phe Asp Ile Cys Tyr Leu Phe Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
                340                 345                 350

Val Ile Arg Thr Thr Gly Tyr Leu Leu Phe Ile Leu His Ile Asn Ala
            355                 360                 365

Cys Val Tyr Tyr Trp Ala Ser Asn Tyr Glu Gly Ile Gly Thr Thr Arg
        370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Phe Ser Gly Val Phe
                420                 425                 430

Val Phe Ser Ser Leu Ile Gly Gln Met Arg Asp Val Ile Gly Ala Ala
            435                 440                 445

Thr Ala Asn Gln Asn Tyr Phe Arg Ala Cys Met Asp Asp Thr Ile Ala
        450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
        515                 520                 525

Asp Thr Gln Met Ile Tyr Asp Met Leu Leu Arg Leu Lys Ser Val Leu
        530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
        595                 600                 605
```

```
Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
        675                 680                 685

Ala Arg Leu Leu Lys Leu Lys Arg Glu Gln Ala Ala Gln Lys Lys Glu
690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
        755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805

<210> SEQ ID NO 35
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 35

Lys Leu Ala Lys Leu Ala Lys Lys Leu Ala Lys Leu Ala Lys His Leu
1               5                   10                  15

Ala His Leu Ala His His Leu Ala His Leu Ala His His Leu Ala His
                20                  25                  30

Val Arg Arg Ala Xaa Asn Xaa Pro Gly
            35                  40

<210> SEQ ID NO 36
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (37)..(37)
<223> OTHER INFORMATION: Xaa can be any naturally occurring amino acid
```

```
<220> FEATURE:
<221> NAME/KEY: misc_feature
<222> LOCATION: (39)..(39)
<223> OTHER INFORMATION: Xaa can be any naturally occurring amino acid

<400> SEQUENCE: 36

His Leu Ala His Leu Ala His His Leu Ala His Leu Ala His His Leu
1               5                   10                  15

Ala His Lys Leu Ala Lys Leu Ala Lys Lys Leu Ala Lys Leu Ala Lys
            20                  25                  30

Val Arg Arg Ala Xaa Asn Xaa Pro Gly
        35                  40

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

His Leu Ala His Leu Ala His
1               5

<210> SEQ ID NO 38
<211> LENGTH: 18
<212> TYPE: PRT
<213> ORGANISM: Artificial Sequence
<220> FEATURE:
<223> OTHER INFORMATION: Synthetic peptide

<400> SEQUENCE: 38

His Leu Ala His Leu Ala His His Leu Ala His Leu Ala His His Leu
1               5                   10                  15

Ala His

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Lys Leu Ala Lys Leu Ala Lys
1               5

<210> SEQ ID NO 40
<211> LENGTH: 18
<212> TYPE: PRT
<213> ORGANISM: Artificial Sequence
<220> FEATURE:
<223> OTHER INFORMATION: Synthetic peptide

<400> SEQUENCE: 40

Lys Leu Ala Lys Leu Ala Lys Lys Leu Ala Lys Leu Ala Lys Lys Leu
1               5                   10                  15

Ala Lys

<210> SEQ ID NO 41
<211> LENGTH: 27
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 41

Lys Leu Ala Lys Leu Ala Lys Lys Leu Ala Lys Leu Ala Lys Lys Leu
1               5                   10                  15

Ala Lys Val Arg Arg Ala Xaa Asn Xaa Pro Gly
            20                  25

<210> SEQ ID NO 42
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 42

Lys Leu Ala Lys Leu Ala Lys Lys Leu Ala Lys Leu Ala Lys Lys Leu
1               5                   10                  15

Ala Lys His Leu Ala His Leu Ala His His Leu Ala His Leu Ala His
            20                  25                  30

His Leu Ala His Val Arg Arg Ala Xaa Asn Xaa Pro Gly
            35                  40                  45

<210> SEQ ID NO 43
<211> LENGTH: 27
<212> TYPE: PRT
<213> ORGANISM: Artificial Sequence
<220> FEATURE:
<223> OTHER INFORMATION: Synthetic peptide

<400> SEQUENCE: 43

His Leu Ala His Leu Ala His His Leu Ala His Leu Ala His His Leu
1               5                   10                  15

Ala His Val Arg Arg Ala Asp Asn Arg Pro Gly
            20                  25

<210> SEQ ID NO 44
<211> LENGTH: 23
<212> TYPE: PRT
<213> ORGANISM: Artificial Sequence
<220> FEATURE:
<223> OTHER INFORMATION: Synthetic peptide

<400> SEQUENCE: 44

His Leu Ala His Leu Ala His His Leu Ala His Leu Ala His Val Arg
1               5                   10                  15

Arg Ala Asp Asn Arg Pro Gly
            20
```

```
<210> SEQ ID NO 45
<211> LENGTH: 37
<212> TYPE: PRT
<213> ORGANISM: Artificial Sequence
<220> FEATURE:
<223> OTHER INFORMATION: Synthetic peptide

<400> SEQUENCE: 45

Lys Leu Ala Lys Leu Ala Lys Lys Leu Ala Lys Leu Ala Lys His Leu
1               5                   10                  15

Ala His Leu Ala His His Leu Ala His Leu Ala His Val Arg Arg Ala
            20                  25                  30

Asp Asn Arg Pro Gly
        35

<210> SEQ ID NO 46
<211> LENGTH: 36
<212> TYPE: PRT
<213> ORGANISM: Artificial Sequence
<220> FEATURE:
<223> OTHER INFORMATION: Synthetic peptide

<400> SEQUENCE: 46

Lys Leu Ala Lys Leu Ala Lys Lys Leu Ala Lys Leu Ala His Leu Ala
1               5                   10                  15

His Leu Ala His His Leu Ala His Leu Ala His Val Arg Arg Ala Asp
            20                  25                  30

Asn Arg Pro Gly
        35

<210> SEQ ID NO 47
<211> LENGTH: 35
<212> TYPE: PRT
<213> ORGANISM: Artificial Sequence
<220> FEATURE:
<223> OTHER INFORMATION: Synthetic peptide

<400> SEQUENCE: 47

Lys Leu Ala Lys Leu Ala Lys Lys Leu Ala Lys Leu His Leu Ala His
1               5                   10                  15

Leu Ala His His Leu Ala His Leu Ala His Val Arg Arg Ala Asp Asn
            20                  25                  30

Arg Pro Gly
        35

<210> SEQ ID NO 48
<211> LENGTH: 34
<212> TYPE: PRT
<213> ORGANISM: Artificial Sequence
<220> FEATURE:
<223> OTHER INFORMATION: Synthetic peptide

<400> SEQUENCE: 48

Lys Leu Ala Lys Leu Ala Lys Lys Leu Ala Lys His Leu Ala His Leu
1               5                   10                  15

Ala His His Leu Ala His Leu Ala His Val Arg Arg Ala Asp Asn Arg
            20                  25                  30

Pro Gly

<210> SEQ ID NO 49
<211> LENGTH: 33
<212> TYPE: PRT
<213> ORGANISM: Artificial Sequence
```

-continued

```
<220> FEATURE:
<223> OTHER INFORMATION: Synthetic peptide

<400> SEQUENCE: 49

Lys Leu Ala Lys Leu Ala Lys Lys Leu Ala His Leu Ala His Leu Ala
1               5                   10                  15

His His Leu Ala His Leu Ala His Val Arg Arg Ala Asp Asn Arg Pro
            20                  25                  30

Gly

<210> SEQ ID NO 50
<211> LENGTH: 32
<212> TYPE: PRT
<213> ORGANISM: Artificial Sequence
<220> FEATURE:
<223> OTHER INFORMATION: Synthetic peptide

<400> SEQUENCE: 50

Lys Leu Ala Lys Leu Ala Lys Lys Leu His Leu Ala His Leu Ala His
1               5                   10                  15

His Leu Ala His Leu Ala His Val Arg Arg Ala Asp Asn Arg Pro Gly
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Synthetic peptide

<400> SEQUENCE: 51

Lys Leu Ala Lys Leu Ala Lys Lys His Leu Ala His Leu Ala His His
1               5                   10                  15

Leu Ala His Leu Ala His Val Arg Arg Ala Asp Asn Arg Pro Gly
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic peptide

<400> SEQUENCE: 52

Lys Leu Ala Lys Leu Ala Lys His Leu Ala His Leu Ala His His Leu
1               5                   10                  15

Ala His Leu Ala His Val Arg Arg Ala Asp Asn Arg Pro Gly
            20                  25                  30

<210> SEQ ID NO 53
<211> LENGTH: 37
<212> TYPE: PRT
<213> ORGANISM: Artificial Sequence
<220> FEATURE:
<223> OTHER INFORMATION: Synthetic peptide

<400> SEQUENCE: 53

His Leu Ala His Leu Ala His His Leu Ala His Leu Ala His Lys Leu
1               5                   10                  15

Ala Lys Leu Ala Lys Lys Leu Ala Lys Leu Ala Lys Val Arg Arg Ala
            20                  25                  30

Asp Asn Arg Pro Gly
        35
```

-continued

<210> SEQ ID NO 54
<211> LENGTH: 36
<212> TYPE: PRT
<213> ORGANISM: Artificial Sequence
<220> FEATURE:
<223> OTHER INFORMATION: Synthetic peptide

<400> SEQUENCE: 54

His Leu Ala His Leu Ala His His Leu Ala His Leu Ala Lys Leu Ala
1               5                   10                  15

Lys Leu Ala Lys Lys Leu Ala Lys Leu Ala Lys Val Arg Arg Ala Asp
            20                  25                  30

Asn Arg Pro Gly
        35

<210> SEQ ID NO 55
<211> LENGTH: 35
<212> TYPE: PRT
<213> ORGANISM: Artificial Sequence
<220> FEATURE:
<223> OTHER INFORMATION: Synthetic peptide

<400> SEQUENCE: 55

His Leu Ala His Leu Ala His His Leu Ala His Leu Lys Leu Ala Lys
1               5                   10                  15

Leu Ala Lys Lys Leu Ala Lys Leu Ala Lys Val Arg Arg Ala Asp Asn
            20                  25                  30

Arg Pro Gly
        35

<210> SEQ ID NO 56
<211> LENGTH: 34
<212> TYPE: PRT
<213> ORGANISM: Artificial Sequence
<220> FEATURE:
<223> OTHER INFORMATION: Synthetic peptide

<400> SEQUENCE: 56

His Leu Ala His Leu Ala His His Leu Ala His Lys Leu Ala Lys Leu
1               5                   10                  15

Ala Lys Lys Leu Ala Lys Leu Ala Lys Val Arg Arg Ala Asp Asn Arg
            20                  25                  30

Pro Gly

<210> SEQ ID NO 57
<211> LENGTH: 33
<212> TYPE: PRT
<213> ORGANISM: Artificial Sequence
<220> FEATURE:
<223> OTHER INFORMATION: Synthetic peptide

<400> SEQUENCE: 57

His Leu Ala His Leu Ala His Leu Ala Lys Leu Ala Lys Leu Ala
1               5                   10                  15

Lys Lys Leu Ala Lys Leu Ala Lys Val Arg Arg Ala Asp Asn Arg Pro
            20                  25                  30

Gly

<210> SEQ ID NO 58
<211> LENGTH: 31
<212> TYPE: PRT
<213> ORGANISM: Artificial Sequence

```
<220> FEATURE:
<223> OTHER INFORMATION: Synthetic peptide

<400> SEQUENCE: 58

Leu Ala His Leu Ala His His Leu Lys Leu Ala Lys Leu Ala Lys Lys
1               5                   10                  15

Leu Ala Lys Leu Ala Lys Val Arg Arg Ala Asp Asn Arg Pro Gly
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Synthetic peptide

<400> SEQUENCE: 59

His Leu Ala His Leu Ala His His Lys Leu Ala Lys Leu Ala Lys Lys
1               5                   10                  15

Leu Ala Lys Leu Ala Lys Val Arg Arg Ala Asp Asn Arg Pro Gly
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic peptide

<400> SEQUENCE: 60

His Leu Ala His Leu Ala His Lys Leu Ala Lys Leu Ala Lys Lys Leu
1               5                   10                  15

Ala Lys Leu Ala Lys Val Arg Arg Ala Asp Asn Arg Pro Gly
            20                  25                  30

<210> SEQ ID NO 61
<211> LENGTH: 36
<212> TYPE: PRT
<213> ORGANISM: Artificial Sequence
<220> FEATURE:
<223> OTHER INFORMATION: Synthetic peptide

<400> SEQUENCE: 61

Lys Leu Ala Lys Leu Ala Lys Lys Leu Ala Lys Leu Ala Lys His Leu
1               5                   10                  15

Ala His Leu Ala His His Leu Ala His Leu Ala Val Arg Arg Ala Asp
            20                  25                  30

Asn Arg Pro Gly
        35

<210> SEQ ID NO 62
<211> LENGTH: 35
<212> TYPE: PRT
<213> ORGANISM: Artificial Sequence
<220> FEATURE:
<223> OTHER INFORMATION: Synthetic peptide
```

```
<400> SEQUENCE: 62

Lys Leu Ala Lys Leu Ala Lys Lys Leu Ala Lys Leu Ala His Leu Ala
1               5                   10                  15

His Leu Ala His His Leu Ala His Leu Ala Val Arg Arg Ala Asp Asn
            20                  25                  30

Arg Pro Gly
        35

<210> SEQ ID NO 63
<211> LENGTH: 34
<212> TYPE: PRT
<213> ORGANISM: Artificial Sequence
<220> FEATURE:
<223> OTHER INFORMATION: Synthetic peptide

<400> SEQUENCE: 63

Lys Leu Ala Lys Leu Ala Lys Lys Leu Ala Lys Leu His Leu Ala His
1               5                   10                  15

Leu Ala His His Leu Ala His Leu Ala Val Arg Arg Ala Asp Asn Arg
            20                  25                  30

Pro Gly

<210> SEQ ID NO 64
<211> LENGTH: 33
<212> TYPE: PRT
<213> ORGANISM: Artificial Sequence
<220> FEATURE:
<223> OTHER INFORMATION: Synthetic peptide

<400> SEQUENCE: 64

Lys Leu Ala Lys Leu Ala Lys Lys Leu Ala Lys His Leu Ala His Leu
1               5                   10                  15

Ala His His Leu Ala His Leu Ala Val Arg Arg Ala Asp Asn Arg Pro
            20                  25                  30

Gly

<210> SEQ ID NO 65
<211> LENGTH: 32
<212> TYPE: PRT
<213> ORGANISM: Artificial Sequence
<220> FEATURE:
<223> OTHER INFORMATION: Synthetic peptide

<400> SEQUENCE: 65

Lys Leu Ala Lys Leu Ala Lys Lys Leu Ala His Leu Ala His Leu Ala
1               5                   10                  15

His His Leu Ala His Leu Ala Val Arg Arg Ala Asp Asn Arg Pro Gly
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Synthetic peptide

<400> SEQUENCE: 66

Lys Leu Ala Lys Leu Ala Lys Lys Leu His Leu Ala His Leu Ala His
1               5                   10                  15

His Leu Ala His Leu Ala Val Arg Arg Ala Asp Asn Arg Pro Gly
            20                  25                  30
```

```
<210> SEQ ID NO 67
<211> LENGTH: 30
<212> TYPE: PRT
<213> ORGANISM: Artificial Sequence
<220> FEATURE:
<223> OTHER INFORMATION: Synthetic peptide

<400> SEQUENCE: 67
```

Lys Leu Ala Lys Leu Ala Lys Lys His Leu Ala His Leu Ala His His
1               5                   10                  15

Leu Ala His Leu Ala Val Arg Arg Ala Asp Asn Arg Pro Gly
            20                  25                  30

```
<210> SEQ ID NO 68
<211> LENGTH: 29
<212> TYPE: PRT
<213> ORGANISM: Artificial Sequence
<220> FEATURE:
<223> OTHER INFORMATION: Synthetic peptide

<400> SEQUENCE: 68
```

Lys Leu Ala Lys Leu Ala Lys His Leu Ala His Leu Ala His His Leu
1               5                   10                  15

Ala His Leu Ala Val Arg Arg Ala Asp Asn Arg Pro Gly
            20                  25

```
<210> SEQ ID NO 69
<211> LENGTH: 36
<212> TYPE: PRT
<213> ORGANISM: Artificial Sequence
<220> FEATURE:
<223> OTHER INFORMATION: Synthetic peptide

<400> SEQUENCE: 69
```

His Leu Ala His Leu Ala His His Leu Ala His Leu Ala His Lys Leu
1               5                   10                  15

Ala Lys Leu Ala Lys Lys Leu Ala Lys Leu Ala Val Arg Arg Ala Asp
            20                  25                  30

Asn Arg Pro Gly
        35

```
<210> SEQ ID NO 70
<211> LENGTH: 35
<212> TYPE: PRT
<213> ORGANISM: Artificial Sequence
<220> FEATURE:
<223> OTHER INFORMATION: Synthetic peptide

<400> SEQUENCE: 70
```

His Leu Ala His Leu Ala His His Leu Ala His Leu Ala Lys Leu Ala
1               5                   10                  15

Lys Leu Ala Lys Lys Leu Ala Lys Leu Ala Val Arg Arg Ala Asp Asn
            20                  25                  30

Arg Pro Gly
        35

```
<210> SEQ ID NO 71
<211> LENGTH: 34
<212> TYPE: PRT
<213> ORGANISM: Artificial Sequence
<220> FEATURE:
<223> OTHER INFORMATION: Synthetic peptide
```

```
<400> SEQUENCE: 71

His Leu Ala His Leu Ala His His Leu Ala His Leu Lys Leu Ala Lys
1               5                   10                  15

Leu Ala Lys Lys Leu Ala Lys Leu Ala Val Arg Arg Ala Asp Asn Arg
            20                  25                  30

Pro Gly

<210> SEQ ID NO 72
<211> LENGTH: 33
<212> TYPE: PRT
<213> ORGANISM: Artificial Sequence
<220> FEATURE:
<223> OTHER INFORMATION: Synthetic peptide

<400> SEQUENCE: 72

His Leu Ala His Leu Ala His His Leu Ala His Lys Leu Ala Lys Leu
1               5                   10                  15

Ala Lys Lys Leu Ala Lys Leu Ala Val Arg Arg Ala Asp Asn Arg Pro
            20                  25                  30

Gly

<210> SEQ ID NO 73
<211> LENGTH: 32
<212> TYPE: PRT
<213> ORGANISM: Artificial Sequence
<220> FEATURE:
<223> OTHER INFORMATION: Synthetic peptide

<400> SEQUENCE: 73

His Leu Ala His Leu Ala His His Leu Ala Lys Leu Ala Lys Leu Ala
1               5                   10                  15

Lys Lys Leu Ala Lys Leu Ala Val Arg Arg Ala Asp Asn Arg Pro Gly
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Synthetic peptide

<400> SEQUENCE: 74

His Leu Ala His Leu Ala His His Leu Lys Leu Ala Lys Leu Ala Lys
1               5                   10                  15

Lys Leu Ala Lys Leu Ala Val Arg Arg Ala Asp Asn Arg Pro Gly
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Synthetic peptide

<400> SEQUENCE: 75

His Leu Ala His Leu Ala His His Lys Leu Ala Lys Leu Ala Lys Lys
1               5                   10                  15

Leu Ala Lys Leu Ala Val Arg Arg Ala Asp Asn Arg Pro Gly
            20                  25                  30
```

```
<210> SEQ ID NO 76
<211> LENGTH: 29
<212> TYPE: PRT
<213> ORGANISM: Artificial Sequence
<220> FEATURE:
<223> OTHER INFORMATION: Synthetic peptide

<400> SEQUENCE: 76

His Leu Ala His Leu Ala His Lys Leu Ala Lys Leu Ala Lys Leu
1               5                   10                  15

Ala Lys Leu Ala Val Arg Arg Ala Asp Asn Arg Pro Gly
            20                  25

<210> SEQ ID NO 77
<211> LENGTH: 35
<212> TYPE: PRT
<213> ORGANISM: Artificial Sequence
<220> FEATURE:
<223> OTHER INFORMATION: Synthetic peptide

<400> SEQUENCE: 77

Lys Leu Ala Lys Leu Ala Lys Lys Leu Ala Lys Leu Ala Lys His Leu
1               5                   10                  15

Ala His Leu Ala His His Leu Ala His Leu Val Arg Arg Ala Asp Asn
            20                  25                  30

Arg Pro Gly
        35

<210> SEQ ID NO 78
<211> LENGTH: 34
<212> TYPE: PRT
<213> ORGANISM: Artificial Sequence
<220> FEATURE:
<223> OTHER INFORMATION: Synthetic peptide

<400> SEQUENCE: 78

Lys Leu Ala Lys Leu Ala Lys Lys Leu Ala Lys Leu Ala His Leu Ala
1               5                   10                  15

His Leu Ala His His Leu Ala His Leu Val Arg Arg Ala Asp Asn Arg
            20                  25                  30

Pro Gly

<210> SEQ ID NO 79
<211> LENGTH: 33
<212> TYPE: PRT
<213> ORGANISM: Artificial Sequence
<220> FEATURE:
<223> OTHER INFORMATION: Synthetic peptide

<400> SEQUENCE: 79

Lys Leu Ala Lys Leu Ala Lys Lys Leu Ala Lys Leu His Leu Ala His
1               5                   10                  15

Leu Ala His His Leu Ala His Leu Val Arg Arg Ala Asp Asn Arg Pro
            20                  25                  30

Gly

<210> SEQ ID NO 80
<211> LENGTH: 32
<212> TYPE: PRT
<213> ORGANISM: Artificial Sequence
<220> FEATURE:
<223> OTHER INFORMATION: Synthetic peptide
```

<400> SEQUENCE: 80

Lys Leu Ala Lys Leu Ala Lys Lys Leu Ala Lys His Leu Ala His Leu
1               5                   10                  15

Ala His His Leu Ala His Leu Val Arg Arg Ala Asp Asn Arg Pro Gly
            20                  25                  30

<210> SEQ ID NO 81
<211> LENGTH: 31
<212> TYPE: PRT
<213> ORGANISM: Artificial Sequence
<220> FEATURE:
<223> OTHER INFORMATION: Synthetic peptide

<400> SEQUENCE: 81

Lys Leu Ala Lys Leu Ala Lys Lys Leu Ala His Leu Ala His Leu Ala
1               5                   10                  15

His His Leu Ala His Leu Val Arg Arg Ala Asp Asn Arg Pro Gly
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Synthetic peptide

<400> SEQUENCE: 82

Lys Leu Ala Lys Leu Ala Lys Lys Leu His Leu Ala His Leu Ala His
1               5                   10                  15

His Leu Ala His Leu Val Arg Arg Ala Asp Asn Arg Pro Gly
            20                  25                  30

<210> SEQ ID NO 83
<211> LENGTH: 29
<212> TYPE: PRT
<213> ORGANISM: Artificial Sequence
<220> FEATURE:
<223> OTHER INFORMATION: Synthetic peptide

<400> SEQUENCE: 83

Lys Leu Ala Lys Leu Ala Lys Lys His Leu Ala His Leu Ala His His
1               5                   10                  15

Leu Ala His Leu Val Arg Arg Ala Asp Asn Arg Pro Gly
            20                  25

<210> SEQ ID NO 84
<211> LENGTH: 28
<212> TYPE: PRT
<213> ORGANISM: Artificial Sequence
<220> FEATURE:
<223> OTHER INFORMATION: Synthetic peptide

<400> SEQUENCE: 84

Lys Leu Ala Lys Leu Ala Lys His Leu Ala His Leu Ala His His Leu
1               5                   10                  15

Ala His Leu Val Arg Arg Ala Asp Asn Arg Pro Gly
            20                  25

<210> SEQ ID NO 85
<211> LENGTH: 35
<212> TYPE: PRT
<213> ORGANISM: Artificial Sequence
<220> FEATURE:
<223> OTHER INFORMATION: Synthetic peptide

```
<400> SEQUENCE: 85

His Leu Ala His Leu Ala His His Leu Ala His Leu Ala His Lys Leu
1               5                   10                  15

Ala Lys Leu Ala Lys Lys Leu Ala Lys Leu Val Arg Arg Ala Asp Asn
            20                  25                  30

Arg Pro Gly
        35

<210> SEQ ID NO 86
<211> LENGTH: 34
<212> TYPE: PRT
<213> ORGANISM: Artificial Sequence
<220> FEATURE:
<223> OTHER INFORMATION: Synthetic peptide

<400> SEQUENCE: 86

His Leu Ala His Leu Ala His His Leu Ala His Leu Ala Lys Leu Ala
1               5                   10                  15

Lys Leu Ala Lys Lys Leu Ala Lys Leu Val Arg Arg Ala Asp Asn Arg
            20                  25                  30

Pro Gly

<210> SEQ ID NO 87
<211> LENGTH: 33
<212> TYPE: PRT
<213> ORGANISM: Artificial Sequence
<220> FEATURE:
<223> OTHER INFORMATION: Synthetic peptide

<400> SEQUENCE: 87

His Leu Ala His Leu Ala His His Leu Ala His Leu Lys Leu Ala Lys
1               5                   10                  15

Leu Ala Lys Lys Leu Ala Lys Leu Val Arg Arg Ala Asp Asn Arg Pro
            20                  25                  30

Gly

<210> SEQ ID NO 88
<211> LENGTH: 32
<212> TYPE: PRT
<213> ORGANISM: Artificial Sequence
<220> FEATURE:
<223> OTHER INFORMATION: Synthetic peptide

<400> SEQUENCE: 88

His Leu Ala His Leu Ala His His Leu Ala His Lys Leu Ala Lys Leu
1               5                   10                  15

Ala Lys Lys Leu Ala Lys Leu Val Arg Arg Ala Asp Asn Arg Pro Gly
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Synthetic peptide

<400> SEQUENCE: 89

His Leu Ala His Leu Ala His His Leu Ala Lys Leu Ala Lys Leu Ala
1               5                   10                  15

Lys Lys Leu Ala Lys Leu Val Arg Arg Ala Asp Asn Arg Pro Gly
            20                  25                  30
```

-continued

<210> SEQ ID NO 90
<211> LENGTH: 30
<212> TYPE: PRT
<213> ORGANISM: Artificial Sequence
<220> FEATURE:
<223> OTHER INFORMATION: Synthetic peptide

<400> SEQUENCE: 90

His Leu Ala His Leu Ala His His Leu Lys Leu Ala Lys Leu Ala Lys
1               5                   10                  15

Lys Leu Ala Lys Leu Val Arg Arg Ala Asp Asn Arg Pro Gly
            20                  25                  30

<210> SEQ ID NO 91
<211> LENGTH: 29
<212> TYPE: PRT
<213> ORGANISM: Artificial Sequence
<220> FEATURE:
<223> OTHER INFORMATION: Synthetic peptide

<400> SEQUENCE: 91

His Leu Ala His Leu Ala His His Lys Leu Ala Lys Leu Ala Lys Lys
1               5                   10                  15

Leu Ala Lys Leu Val Arg Arg Ala Asp Asn Arg Pro Gly
            20                  25

<210> SEQ ID NO 92
<211> LENGTH: 28
<212> TYPE: PRT
<213> ORGANISM: Artificial Sequence
<220> FEATURE:
<223> OTHER INFORMATION: Synthetic peptide

<400> SEQUENCE: 92

His Leu Ala His Leu Ala His Lys Leu Ala Lys Leu Ala Lys Lys Leu
1               5                   10                  15

Ala Lys Leu Val Arg Arg Ala Asp Asn Arg Pro Gly
            20                  25

<210> SEQ ID NO 93
<211> LENGTH: 34
<212> TYPE: PRT
<213> ORGANISM: Artificial Sequence
<220> FEATURE:
<223> OTHER INFORMATION: Synthetic peptide

<400> SEQUENCE: 93

Lys Leu Ala Lys Leu Ala Lys Lys Leu Ala Lys Leu Ala Lys His Leu
1               5                   10                  15

Ala His Leu Ala His His Leu Ala His Val Arg Arg Ala Asp Asn Arg
            20                  25                  30

Pro Gly

<210> SEQ ID NO 94
<211> LENGTH: 33
<212> TYPE: PRT
<213> ORGANISM: Artificial Sequence
<220> FEATURE:
<223> OTHER INFORMATION: Synthetic peptide

```
<400> SEQUENCE: 94

Lys Leu Ala Lys Leu Ala Lys Lys Leu Ala Lys Leu Ala His Leu Ala
1               5                   10                  15

His Leu Ala His His Leu Ala His Val Arg Arg Ala Asp Asn Arg Pro
            20                  25                  30

Gly

<210> SEQ ID NO 95
<211> LENGTH: 32
<212> TYPE: PRT
<213> ORGANISM: Artificial Sequence
<220> FEATURE:
<223> OTHER INFORMATION: Synthetic peptide

<400> SEQUENCE: 95

Lys Leu Ala Lys Leu Ala Lys Lys Leu Ala Lys Leu His Leu Ala His
1               5                   10                  15

Leu Ala His His Leu Ala His Val Arg Arg Ala Asp Asn Arg Pro Gly
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Synthetic peptide

<400> SEQUENCE: 96

Lys Leu Ala Lys Leu Ala Lys Lys Leu Ala Lys His Leu Ala His Leu
1               5                   10                  15

Ala His His Leu Ala His Val Arg Arg Ala Asp Asn Arg Pro Gly
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Synthetic peptide

<400> SEQUENCE: 97

Lys Leu Ala Lys Leu Ala Lys Lys Leu Ala His Leu Ala His Leu Ala
1               5                   10                  15

His His Leu Ala His Val Arg Arg Ala Asp Asn Arg Pro Gly
            20                  25                  30

<210> SEQ ID NO 98
<211> LENGTH: 29
<212> TYPE: PRT
<213> ORGANISM: Artificial Sequence
<220> FEATURE:
<223> OTHER INFORMATION: Synthetic peptide

<400> SEQUENCE: 98

Lys Leu Ala Lys Leu Ala Lys Lys Leu His Leu Ala His Leu Ala His
1               5                   10                  15

His Leu Ala His Val Arg Arg Ala Asp Asn Arg Pro Gly
            20                  25

<210> SEQ ID NO 99
<211> LENGTH: 28
<212> TYPE: PRT
<213> ORGANISM: Artificial Sequence
```

```
<220> FEATURE:
<223> OTHER INFORMATION: Synthetic peptide

<400> SEQUENCE: 99

Lys Leu Ala Lys Leu Ala Lys Lys His Leu Ala His Leu Ala His His
1               5                   10                  15

Leu Ala His Val Arg Arg Ala Asp Asn Arg Pro Gly
            20                  25

<210> SEQ ID NO 100
<211> LENGTH: 27
<212> TYPE: PRT
<213> ORGANISM: Artificial Sequence
<220> FEATURE:
<223> OTHER INFORMATION: Synthetic peptide

<400> SEQUENCE: 100

Lys Leu Ala Lys Leu Ala Lys His Leu Ala His Leu Ala His His Leu
1               5                   10                  15

Ala His Val Arg Arg Ala Asp Asn Arg Pro Gly
            20                  25

<210> SEQ ID NO 101
<211> LENGTH: 34
<212> TYPE: PRT
<213> ORGANISM: Artificial Sequence
<220> FEATURE:
<223> OTHER INFORMATION: Synthetic peptide

<400> SEQUENCE: 101

His Leu Ala His Leu Ala His His Leu Ala His Leu Ala His Lys Leu
1               5                   10                  15

Ala Lys Leu Ala Lys Lys Leu Ala Lys Val Arg Arg Ala Asp Asn Arg
            20                  25                  30

Pro Gly

<210> SEQ ID NO 102
<211> LENGTH: 33
<212> TYPE: PRT
<213> ORGANISM: Artificial Sequence
<220> FEATURE:
<223> OTHER INFORMATION: Synthetic peptide

<400> SEQUENCE: 102

His Leu Ala His Leu Ala His His Leu Ala His Leu Ala Lys Leu Ala
1               5                   10                  15

Lys Leu Ala Lys Lys Leu Ala Lys Val Arg Arg Ala Asp Asn Arg Pro
            20                  25                  30

Gly

<210> SEQ ID NO 103
<211> LENGTH: 32
<212> TYPE: PRT
<213> ORGANISM: Artificial Sequence
<220> FEATURE:
<223> OTHER INFORMATION: Synthetic peptide

<400> SEQUENCE: 103

His Leu Ala His Leu Ala His His Leu Ala His Leu Lys Leu Ala Lys
1               5                   10                  15

Leu Ala Lys Lys Leu Ala Lys Val Arg Arg Ala Asp Asn Arg Pro Gly
            20                  25                  30
```

```
<210> SEQ ID NO 104
<211> LENGTH: 31
<212> TYPE: PRT
<213> ORGANISM: Artificial Sequence
<220> FEATURE:
<223> OTHER INFORMATION: Synthetic peptide

<400> SEQUENCE: 104

His Leu Ala His Leu Ala His His Leu Ala His Lys Leu Ala Lys Leu
1               5                   10                  15

Ala Lys Lys Leu Ala Lys Val Arg Arg Ala Asp Asn Arg Pro Gly
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Synthetic peptide

<400> SEQUENCE: 105

His Leu Ala His Leu Ala His His Leu Ala Lys Leu Ala Lys Leu Ala
1               5                   10                  15

Lys Lys Leu Ala Lys Val Arg Arg Ala Asp Asn Arg Pro Gly
            20                  25                  30

<210> SEQ ID NO 106
<211> LENGTH: 29
<212> TYPE: PRT
<213> ORGANISM: Artificial Sequence
<220> FEATURE:
<223> OTHER INFORMATION: Synthetic peptide

<400> SEQUENCE: 106

His Leu Ala His Leu Ala His His Leu Lys Leu Ala Lys Leu Ala Lys
1               5                   10                  15

Lys Leu Ala Lys Val Arg Arg Ala Asp Asn Arg Pro Gly
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic peptide

<400> SEQUENCE: 107

His Leu Ala His Leu Ala His His Lys Leu Ala Lys Leu Ala Lys Lys
1               5                   10                  15

Leu Ala Lys Val Arg Arg Ala Asp Asn Arg Pro Gly
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic peptide

<400> SEQUENCE: 108

His Leu Ala His Leu Ala His Lys Leu Ala Lys Leu Ala Lys Lys Leu
1               5                   10                  15

Ala Lys Val Arg Arg Ala Asp Asn Arg Pro Gly
            20                  25
```

<210> SEQ ID NO 109
<211> LENGTH: 33
<212> TYPE: PRT
<213> ORGANISM: Artificial Sequence
<220> FEATURE:
<223> OTHER INFORMATION: Synthetic peptide

<400> SEQUENCE: 109

```
Lys Leu Ala Lys Leu Ala Lys Lys Leu Ala Lys Leu Ala Lys His Leu
1               5                   10                  15
Ala His Leu Ala His His Leu Ala Val Arg Arg Ala Asp Asn Arg Pro
            20                  25                  30
Gly
```

<210> SEQ ID NO 110
<211> LENGTH: 32
<212> TYPE: PRT
<213> ORGANISM: Artificial Sequence
<220> FEATURE:
<223> OTHER INFORMATION: Synthetic peptide

<400> SEQUENCE: 110

```
Lys Leu Ala Lys Leu Ala Lys Lys Leu Ala Lys Leu Ala His Leu Ala
1               5                   10                  15
His Leu Ala His His Leu Ala Val Arg Arg Ala Asp Asn Arg Pro Gly
            20                  25                  30
```

<210> SEQ ID NO 111
<211> LENGTH: 31
<212> TYPE: PRT
<213> ORGANISM: Artificial Sequence
<220> FEATURE:
<223> OTHER INFORMATION: Synthetic peptide

<400> SEQUENCE: 111

```
Lys Leu Ala Lys Leu Ala Lys Lys Leu Ala Lys Leu His Leu Ala His
1               5                   10                  15
Leu Ala His His Leu Ala Val Arg Arg Ala Asp Asn Arg Pro Gly
            20                  25                  30
```

<210> SEQ ID NO 112
<211> LENGTH: 30
<212> TYPE: PRT
<213> ORGANISM: Artificial Sequence
<220> FEATURE:
<223> OTHER INFORMATION: Synthetic peptide

<400> SEQUENCE: 112

```
Lys Leu Ala Lys Leu Ala Lys Lys Leu Ala Lys His Leu Ala His Leu
1               5                   10                  15
Ala His His Leu Ala Val Arg Arg Ala Asp Asn Arg Pro Gly
            20                  25                  30
```

<210> SEQ ID NO 113
<211> LENGTH: 29
<212> TYPE: PRT
<213> ORGANISM: Artificial Sequence
<220> FEATURE:
<223> OTHER INFORMATION: Synthetic peptide

```
<400> SEQUENCE: 113

Lys Leu Ala Lys Leu Ala Lys Lys Leu Ala His Leu Ala His Leu Ala
1               5                   10                  15

His His Leu Ala Val Arg Arg Ala Asp Asn Arg Pro Gly
            20                  25

<210> SEQ ID NO 114
<211> LENGTH: 28
<212> TYPE: PRT
<213> ORGANISM: Artificial Sequence
<220> FEATURE:
<223> OTHER INFORMATION: Synthetic peptide

<400> SEQUENCE: 114

Lys Leu Ala Lys Leu Ala Lys Lys Leu His Leu Ala His Leu Ala His
1               5                   10                  15

His Leu Ala Val Arg Arg Ala Asp Asn Arg Pro Gly
            20                  25

<210> SEQ ID NO 115
<211> LENGTH: 27
<212> TYPE: PRT
<213> ORGANISM: Artificial Sequence
<220> FEATURE:
<223> OTHER INFORMATION: Synthetic peptide

<400> SEQUENCE: 115

Lys Leu Ala Lys Leu Ala Lys Lys His Leu Ala His Leu Ala His His
1               5                   10                  15

Leu Ala Val Arg Arg Ala Asp Asn Arg Pro Gly
            20                  25

<210> SEQ ID NO 116
<211> LENGTH: 26
<212> TYPE: PRT
<213> ORGANISM: Artificial Sequence
<220> FEATURE:
<223> OTHER INFORMATION: Synthetic peptide

<400> SEQUENCE: 116

Lys Leu Ala Lys Leu Ala Lys His Leu Ala His Leu Ala His His Leu
1               5                   10                  15

Ala Val Arg Arg Ala Asp Asn Arg Pro Gly
            20                  25

<210> SEQ ID NO 117
<211> LENGTH: 33
<212> TYPE: PRT
<213> ORGANISM: Artificial Sequence
<220> FEATURE:
<223> OTHER INFORMATION: Synthetic peptide

<400> SEQUENCE: 117

His Leu Ala His Leu Ala His His Leu Ala His Leu Ala His Lys Leu
1               5                   10                  15

Ala Lys Leu Ala Lys Lys Leu Ala Val Arg Arg Ala Asp Asn Arg Pro
            20                  25                  30

Gly

<210> SEQ ID NO 118
<211> LENGTH: 32
<212> TYPE: PRT
<213> ORGANISM: Artificial Sequence
```

```
<220> FEATURE:
<223> OTHER INFORMATION: Synthetic peptide

<400> SEQUENCE: 118

His Leu Ala His Leu Ala His His Leu Ala His Leu Ala Lys Leu Ala
1               5                   10                  15

Lys Leu Ala Lys Lys Leu Ala Val Arg Arg Ala Asp Asn Arg Pro Gly
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: Synthetic peptide

<400> SEQUENCE: 119

His Leu Ala His Leu Ala His His Leu Ala His Leu Lys Leu Ala Lys
1               5                   10                  15

Leu Ala Lys Lys Leu Ala Val Arg Arg Ala Asp Asn Arg Pro Gly
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Synthetic peptide

<400> SEQUENCE: 120

His Leu Ala His Leu Ala His His Leu Ala His Lys Leu Ala Lys Leu
1               5                   10                  15

Ala Lys Lys Leu Ala Val Arg Arg Ala Asp Asn Arg Pro Gly
            20                  25                  30

<210> SEQ ID NO 121
<211> LENGTH: 29
<212> TYPE: PRT
<213> ORGANISM: Artificial Sequence
<220> FEATURE:
<223> OTHER INFORMATION: Synthetic peptide

<400> SEQUENCE: 121

His Leu Ala His Leu Ala His His Leu Ala Lys Leu Ala Lys Leu Ala
1               5                   10                  15

Lys Lys Leu Ala Val Arg Arg Ala Asp Asn Arg Pro Gly
            20                  25

<210> SEQ ID NO 122
<211> LENGTH: 28
<212> TYPE: PRT
<213> ORGANISM: Artificial Sequence
<220> FEATURE:
<223> OTHER INFORMATION: Synthetic peptide

<400> SEQUENCE: 122

His Leu Ala His Leu Ala His His Leu Lys Leu Ala Lys Leu Ala Lys
1               5                   10                  15

Lys Leu Ala Val Arg Arg Ala Asp Asn Arg Pro Gly
            20                  25
```

-continued

<210> SEQ ID NO 123
<211> LENGTH: 27
<212> TYPE: PRT
<213> ORGANISM: Artificial Sequence
<220> FEATURE:
<223> OTHER INFORMATION: Synthetic peptide

<400> SEQUENCE: 123

His Leu Ala His Leu Ala His His Lys Leu Ala Lys Leu Ala Lys Lys
1               5                   10                  15

Leu Ala Val Arg Arg Ala Asp Asn Arg Pro Gly
            20                  25

<210> SEQ ID NO 124
<211> LENGTH: 26
<212> TYPE: PRT
<213> ORGANISM: Artificial Sequence
<220> FEATURE:
<223> OTHER INFORMATION: Synthetic peptide

<400> SEQUENCE: 124

His Leu Ala His Leu Ala His Lys Leu Ala Lys Leu Ala Lys Lys Leu
1               5                   10                  15

Ala Val Arg Arg Ala Asp Asn Arg Pro Gly
            20                  25

<210> SEQ ID NO 125
<211> LENGTH: 32
<212> TYPE: PRT
<213> ORGANISM: Artificial Sequence
<220> FEATURE:
<223> OTHER INFORMATION: Synthetic peptide

<400> SEQUENCE: 125

Lys Leu Ala Lys Leu Ala Lys Lys Leu Ala Lys Leu Ala Lys His Leu
1               5                   10                  15

Ala His Leu Ala His His Leu Val Arg Arg Ala Asp Asn Arg Pro Gly
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: Synthetic peptide

<400> SEQUENCE: 126

Lys Leu Ala Lys Leu Ala Lys Lys Leu Ala Lys Leu Ala His Leu Ala
1               5                   10                  15

His Leu Ala His His Leu Val Arg Arg Ala Asp Asn Arg Pro Gly
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Synthetic peptide

<400> SEQUENCE: 127

Lys Leu Ala Lys Leu Ala Lys Lys Leu Ala Lys Leu His Leu Ala His
1               5                   10                  15

Leu Ala His His Leu Val Arg Arg Ala Asp Asn Arg Pro Gly
            20                  25                  30

```
<210> SEQ ID NO 128
<211> LENGTH: 29
<212> TYPE: PRT
<213> ORGANISM: Artificial Sequence
<220> FEATURE:
<223> OTHER INFORMATION: Synthetic peptide

<400> SEQUENCE: 128

Lys Leu Ala Lys Leu Ala Lys Lys Leu Ala Lys His Leu Ala His Leu
1               5                   10                  15

Ala His His Leu Val Arg Arg Ala Asp Asn Arg Pro Gly
            20                  25

<210> SEQ ID NO 129
<211> LENGTH: 28
<212> TYPE: PRT
<213> ORGANISM: Artificial Sequence
<220> FEATURE:
<223> OTHER INFORMATION: Synthetic peptide

<400> SEQUENCE: 129

Lys Leu Ala Lys Leu Ala Lys Lys Leu Ala His Leu Ala His Leu Ala
1               5                   10                  15

His His Leu Val Arg Arg Ala Asp Asn Arg Pro Gly
            20                  25

<210> SEQ ID NO 130
<211> LENGTH: 27
<212> TYPE: PRT
<213> ORGANISM: Artificial Sequence
<220> FEATURE:
<223> OTHER INFORMATION: Synthetic peptide

<400> SEQUENCE: 130

Lys Leu Ala Lys Leu Ala Lys Lys Leu His Leu Ala His Leu Ala His
1               5                   10                  15

His Leu Val Arg Arg Ala Asp Asn Arg Pro Gly
            20                  25

<210> SEQ ID NO 131
<211> LENGTH: 26
<212> TYPE: PRT
<213> ORGANISM: Artificial Sequence
<220> FEATURE:
<223> OTHER INFORMATION: Synthetic peptide

<400> SEQUENCE: 131

Lys Leu Ala Lys Leu Ala Lys Lys His Leu Ala His Leu Ala His His
1               5                   10                  15

Leu Val Arg Arg Ala Asp Asn Arg Pro Gly
            20                  25

<210> SEQ ID NO 132
<211> LENGTH: 25
<212> TYPE: PRT
<213> ORGANISM: Artificial Sequence
<220> FEATURE:
<223> OTHER INFORMATION: Synthetic peptide

<400> SEQUENCE: 132

Lys Leu Ala Lys Leu Ala Lys His Leu Ala His Leu Ala His His Leu
1               5                   10                  15

Val Arg Arg Ala Asp Asn Arg Pro Gly
            20                  25
```

```
<210> SEQ ID NO 133
<211> LENGTH: 32
<212> TYPE: PRT
<213> ORGANISM: Artificial Sequence
<220> FEATURE:
<223> OTHER INFORMATION: Synthetic peptide

<400> SEQUENCE: 133

His Leu Ala His Leu Ala His His Leu Ala His Leu Ala His Lys Leu
1               5                   10                  15

Ala Lys Leu Ala Lys Lys Leu Val Arg Arg Ala Asp Asn Arg Pro Gly
            20                  25                  30

<210> SEQ ID NO 134
<211> LENGTH: 31
<212> TYPE: PRT
<213> ORGANISM: Artificial Sequence
<220> FEATURE:
<223> OTHER INFORMATION: Synthetic peptide

<400> SEQUENCE: 134

His Leu Ala His Leu Ala His His Leu Ala His Leu Ala Lys Leu Ala
1               5                   10                  15

Lys Leu Ala Lys Lys Leu Val Arg Arg Ala Asp Asn Arg Pro Gly
            20                  25                  30

<210> SEQ ID NO 135
<211> LENGTH: 29
<212> TYPE: PRT
<213> ORGANISM: Artificial Sequence
<220> FEATURE:
<223> OTHER INFORMATION: Synthetic peptide

<400> SEQUENCE: 135

His Leu Ala His Leu Ala His His Leu Ala His Lys Leu Ala Lys Leu
1               5                   10                  15

Ala Lys Lys Leu Val Arg Arg Ala Asp Asn Arg Pro Gly
            20                  25

<210> SEQ ID NO 136
<211> LENGTH: 28
<212> TYPE: PRT
<213> ORGANISM: Artificial Sequence
<220> FEATURE:
<223> OTHER INFORMATION: Synthetic peptide

<400> SEQUENCE: 136

His Leu Ala His Leu Ala His His Leu Ala Lys Leu Ala Lys Leu Ala
1               5                   10                  15

Lys Lys Leu Val Arg Arg Ala Asp Asn Arg Pro Gly
            20                  25

<210> SEQ ID NO 137
<211> LENGTH: 27
<212> TYPE: PRT
<213> ORGANISM: Artificial Sequence
<220> FEATURE:
<223> OTHER INFORMATION: Synthetic peptide

<400> SEQUENCE: 137

His Leu Ala His Leu Ala His Leu Lys Leu Ala Lys Leu Ala Lys
1               5                   10                  15

Lys Leu Val Arg Arg Ala Asp Asn Arg Pro Gly
            20                  25
```

```
<210> SEQ ID NO 138
<211> LENGTH: 26
<212> TYPE: PRT
<213> ORGANISM: Artificial Sequence
<220> FEATURE:
<223> OTHER INFORMATION: Synthetic peptide

<400> SEQUENCE: 138

His Leu Ala His Leu Ala His His Lys Leu Ala Lys Leu Ala Lys Lys
1               5                   10                  15

Leu Val Arg Arg Ala Asp Asn Arg Pro Gly
            20                  25

<210> SEQ ID NO 139
<211> LENGTH: 25
<212> TYPE: PRT
<213> ORGANISM: Artificial Sequence
<220> FEATURE:
<223> OTHER INFORMATION: Synthetic peptide

<400> SEQUENCE: 139

His Leu Ala His Leu Ala His Lys Leu Ala Lys Leu Ala Lys Lys Leu
1               5                   10                  15

Val Arg Arg Ala Asp Asn Arg Pro Gly
            20                  25

<210> SEQ ID NO 140
<211> LENGTH: 31
<212> TYPE: PRT
<213> ORGANISM: Artificial Sequence
<220> FEATURE:
<223> OTHER INFORMATION: Synthetic peptide

<400> SEQUENCE: 140

Lys Leu Ala Lys Leu Ala Lys Lys Leu Ala Lys Leu Ala Lys His Leu
1               5                   10                  15

Ala His Leu Ala His His Val Arg Arg Ala Asp Asn Arg Pro Gly
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Synthetic peptide

<400> SEQUENCE: 141

Lys Leu Ala Lys Leu Ala Lys Lys Leu Ala Lys Leu Ala His Leu Ala
1               5                   10                  15

His Leu Ala His His Val Arg Arg Ala Asp Asn Arg Pro Gly
            20                  25                  30

<210> SEQ ID NO 142
<211> LENGTH: 29
<212> TYPE: PRT
<213> ORGANISM: Artificial Sequence
<220> FEATURE:
<223> OTHER INFORMATION: Synthetic peptide

<400> SEQUENCE: 142

Lys Leu Ala Lys Leu Ala Lys Lys Leu Ala Lys Leu His Leu Ala His
1               5                   10                  15

Leu Ala His His Val Arg Arg Ala Asp Asn Arg Pro Gly
            20                  25
```

```
<210> SEQ ID NO 143
<211> LENGTH: 28
<212> TYPE: PRT
<213> ORGANISM: Artificial Sequence
<220> FEATURE:
<223> OTHER INFORMATION: Synthetic peptide

<400> SEQUENCE: 143

Lys Leu Ala Lys Leu Ala Lys Lys Leu Ala Lys His Leu Ala His Leu
1               5                   10                  15

Ala His His Val Arg Arg Ala Asp Asn Arg Pro Gly
            20                  25

<210> SEQ ID NO 144
<211> LENGTH: 27
<212> TYPE: PRT
<213> ORGANISM: Artificial Sequence
<220> FEATURE:
<223> OTHER INFORMATION: Synthetic peptide

<400> SEQUENCE: 144

Lys Leu Ala Lys Leu Ala Lys Lys Leu Ala His Leu Ala His Leu Ala
1               5                   10                  15

His His Val Arg Arg Ala Asp Asn Arg Pro Gly
            20                  25

<210> SEQ ID NO 145
<211> LENGTH: 26
<212> TYPE: PRT
<213> ORGANISM: Artificial Sequence
<220> FEATURE:
<223> OTHER INFORMATION: Synthetic peptide

<400> SEQUENCE: 145

Lys Leu Ala Lys Leu Ala Lys Lys Leu His Leu Ala His Leu Ala His
1               5                   10                  15

His Val Arg Arg Ala Asp Asn Arg Pro Gly
            20                  25

<210> SEQ ID NO 146
<211> LENGTH: 25
<212> TYPE: PRT
<213> ORGANISM: Artificial Sequence
<220> FEATURE:
<223> OTHER INFORMATION: Synthetic peptide

<400> SEQUENCE: 146

Lys Leu Ala Lys Leu Ala Lys Lys His Leu Ala His Leu Ala His His
1               5                   10                  15

Val Arg Arg Ala Asp Asn Arg Pro Gly
            20                  25

<210> SEQ ID NO 147
<211> LENGTH: 24
<212> TYPE: PRT
<213> ORGANISM: Artificial Sequence
<220> FEATURE:
<223> OTHER INFORMATION: Synthetic peptide

<400> SEQUENCE: 147

Lys Leu Ala Lys Leu Ala Lys His Leu Ala His Leu Ala His His Val
1               5                   10                  15

Arg Arg Ala Asp Asn Arg Pro Gly
            20
```

```
<210> SEQ ID NO 148
<211> LENGTH: 31
<212> TYPE: PRT
<213> ORGANISM: Artificial Sequence
<220> FEATURE:
<223> OTHER INFORMATION: Synthetic peptide

<400> SEQUENCE: 148

His Leu Ala His Leu Ala His His Leu Ala His Leu Ala His Lys Leu
1               5                   10                  15

Ala Lys Leu Ala Lys Lys Val Arg Arg Ala Asp Asn Arg Pro Gly
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Synthetic peptide

<400> SEQUENCE: 149

His Leu Ala His Leu Ala His His Leu Ala His Leu Ala Lys Leu Ala
1               5                   10                  15

Lys Leu Ala Lys Lys Val Arg Arg Ala Asp Asn Arg Pro Gly
            20                  25                  30

<210> SEQ ID NO 150
<211> LENGTH: 29
<212> TYPE: PRT
<213> ORGANISM: Artificial Sequence
<220> FEATURE:
<223> OTHER INFORMATION: Synthetic peptide

<400> SEQUENCE: 150

His Leu Ala His Leu Ala His His Leu Ala His Leu Lys Leu Ala Lys
1               5                   10                  15

Leu Ala Lys Lys Val Arg Arg Ala Asp Asn Arg Pro Gly
            20                  25

<210> SEQ ID NO 151
<211> LENGTH: 28
<212> TYPE: PRT
<213> ORGANISM: Artificial Sequence
<220> FEATURE:
<223> OTHER INFORMATION: Synthetic peptide

<400> SEQUENCE: 151

His Leu Ala His Leu Ala His His Leu Ala His Lys Leu Ala Lys Leu
1               5                   10                  15

Ala Lys Lys Val Arg Arg Ala Asp Asn Arg Pro Gly
            20                  25

<210> SEQ ID NO 152
<211> LENGTH: 27
<212> TYPE: PRT
<213> ORGANISM: Artificial Sequence
<220> FEATURE:
<223> OTHER INFORMATION: Synthetic peptide

<400> SEQUENCE: 152

His Leu Ala His Leu Ala His His Leu Ala Lys Leu Ala Lys Leu Ala
1               5                   10                  15

Lys Lys Val Arg Arg Ala Asp Asn Arg Pro Gly
            20                  25
```

-continued

<210> SEQ ID NO 153
<211> LENGTH: 26
<212> TYPE: PRT
<213> ORGANISM: Artificial Sequence
<220> FEATURE:
<223> OTHER INFORMATION: Synthetic peptide

<400> SEQUENCE: 153

His Leu Ala His Leu Ala His His Leu Lys Leu Ala Lys Leu Ala Lys
1               5                   10                  15

Lys Val Arg Arg Ala Asp Asn Arg Pro Gly
            20                  25

<210> SEQ ID NO 154
<211> LENGTH: 25
<212> TYPE: PRT
<213> ORGANISM: Artificial Sequence
<220> FEATURE:
<223> OTHER INFORMATION: Synthetic peptide

<400> SEQUENCE: 154

His Leu Ala His Leu Ala His His Lys Leu Ala Lys Leu Ala Lys Lys
1               5                   10                  15

Val Arg Arg Ala Asp Asn Arg Pro Gly
            20                  25

<210> SEQ ID NO 155
<211> LENGTH: 24
<212> TYPE: PRT
<213> ORGANISM: Artificial Sequence
<220> FEATURE:
<223> OTHER INFORMATION: Synthetic peptide

<400> SEQUENCE: 155

His Leu Ala His Leu Ala His Lys Leu Ala Lys Leu Ala Lys Lys Val
1               5                   10                  15

Arg Arg Ala Asp Asn Arg Pro Gly
            20

<210> SEQ ID NO 156
<211> LENGTH: 30
<212> TYPE: PRT
<213> ORGANISM: Artificial Sequence
<220> FEATURE:
<223> OTHER INFORMATION: Synthetic peptide

<400> SEQUENCE: 156

Lys Leu Ala Lys Leu Ala Lys Lys Leu Ala Lys Leu Ala Lys His Leu
1               5                   10                  15

Ala His Leu Ala His Val Arg Arg Ala Asp Asn Arg Pro Gly
            20                  25                  30

<210> SEQ ID NO 157
<211> LENGTH: 29
<212> TYPE: PRT
<213> ORGANISM: Artificial Sequence
<220> FEATURE:
<223> OTHER INFORMATION: Synthetic peptide

<400> SEQUENCE: 157

Lys Leu Ala Lys Leu Ala Lys Lys Leu Ala Lys Leu Ala His Leu Ala
1               5                   10                  15

His Leu Ala His Val Arg Arg Ala Asp Asn Arg Pro Gly
            20                  25

```
<210> SEQ ID NO 158
<211> LENGTH: 28
<212> TYPE: PRT
<213> ORGANISM: Artificial Sequence
<220> FEATURE:
<223> OTHER INFORMATION: Synthetic peptide

<400> SEQUENCE: 158

Lys Leu Ala Lys Leu Ala Lys Lys Leu Ala Lys Leu His Leu Ala His
1               5                   10                  15

Leu Ala His Val Arg Arg Ala Asp Asn Arg Pro Gly
            20                  25

<210> SEQ ID NO 159
<211> LENGTH: 27
<212> TYPE: PRT
<213> ORGANISM: Artificial Sequence
<220> FEATURE:
<223> OTHER INFORMATION: Synthetic peptide

<400> SEQUENCE: 159

Lys Leu Ala Lys Leu Ala Lys Lys Leu Ala Lys His Leu Ala His Leu
1               5                   10                  15

Ala His Val Arg Arg Ala Asp Asn Arg Pro Gly
            20                  25

<210> SEQ ID NO 160
<211> LENGTH: 26
<212> TYPE: PRT
<213> ORGANISM: Artificial Sequence
<220> FEATURE:
<223> OTHER INFORMATION: Synthetic peptide

<400> SEQUENCE: 160

Lys Leu Ala Lys Leu Ala Lys Lys Leu Ala His Leu Ala His Leu Ala
1               5                   10                  15

His Val Arg Arg Ala Asp Asn Arg Pro Gly
            20                  25

<210> SEQ ID NO 161
<211> LENGTH: 25
<212> TYPE: PRT
<213> ORGANISM: Artificial Sequence
<220> FEATURE:
<223> OTHER INFORMATION: Synthetic peptide

<400> SEQUENCE: 161

Lys Leu Ala Lys Leu Ala Lys Lys Leu His Leu Ala His Leu Ala His
1               5                   10                  15

Val Arg Arg Ala Asp Asn Arg Pro Gly
            20                  25

<210> SEQ ID NO 162
<211> LENGTH: 24
<212> TYPE: PRT
<213> ORGANISM: Artificial Sequence
<220> FEATURE:
<223> OTHER INFORMATION: Synthetic peptide

<400> SEQUENCE: 162

Lys Leu Ala Lys Leu Ala Lys Lys His Leu Ala His Leu Ala His Val
1               5                   10                  15

Arg Arg Ala Asp Asn Arg Pro Gly
            20
```

```
<210> SEQ ID NO 163
<211> LENGTH: 23
<212> TYPE: PRT
<213> ORGANISM: Artificial Sequence
<220> FEATURE:
<223> OTHER INFORMATION: Synthetic peptide

<400> SEQUENCE: 163

Lys Leu Ala Lys Leu Ala Lys His Leu Ala His Leu Ala His Val Arg
1               5                   10                  15

Arg Ala Asp Asn Arg Pro Gly
            20

<210> SEQ ID NO 164
<211> LENGTH: 30
<212> TYPE: PRT
<213> ORGANISM: Artificial Sequence
<220> FEATURE:
<223> OTHER INFORMATION: Synthetic peptide

<400> SEQUENCE: 164

His Leu Ala His Leu Ala His His Leu Ala His Leu Ala His Lys Leu
1               5                   10                  15

Ala Lys Leu Ala Lys Val Arg Arg Ala Asp Asn Arg Pro Gly
            20                  25                  30

<210> SEQ ID NO 165
<211> LENGTH: 29
<212> TYPE: PRT
<213> ORGANISM: Artificial Sequence
<220> FEATURE:
<223> OTHER INFORMATION: Synthetic peptide

<400> SEQUENCE: 165

His Leu Ala His Leu Ala His His Leu Ala His Leu Ala Lys Leu Ala
1               5                   10                  15

Lys Leu Ala Lys Val Arg Arg Ala Asp Asn Arg Pro Gly
            20                  25

<210> SEQ ID NO 166
<211> LENGTH: 28
<212> TYPE: PRT
<213> ORGANISM: Artificial Sequence
<220> FEATURE:
<223> OTHER INFORMATION: Synthetic peptide

<400> SEQUENCE: 166

His Leu Ala His Leu Ala His His Leu Ala His Leu Lys Leu Ala Lys
1               5                   10                  15

Leu Ala Lys Val Arg Arg Ala Asp Asn Arg Pro Gly
            20                  25

<210> SEQ ID NO 167
<211> LENGTH: 27
<212> TYPE: PRT
<213> ORGANISM: Artificial Sequence
<220> FEATURE:
<223> OTHER INFORMATION: Synthetic peptide

<400> SEQUENCE: 167

His Leu Ala His Leu Ala His His Leu Ala His Lys Leu Ala Lys Leu
1               5                   10                  15

Ala Lys Val Arg Arg Ala Asp Asn Arg Pro Gly
            20                  25
```

```
<210> SEQ ID NO 168
<211> LENGTH: 26
<212> TYPE: PRT
<213> ORGANISM: Artificial Sequence
<220> FEATURE:
<223> OTHER INFORMATION: Synthetic peptide

<400> SEQUENCE: 168

His Leu Ala His Leu Ala His His Leu Ala Lys Leu Ala Lys Leu Ala
1               5                   10                  15

Lys Val Arg Arg Ala Asp Asn Arg Pro Gly
            20                  25

<210> SEQ ID NO 169
<211> LENGTH: 25
<212> TYPE: PRT
<213> ORGANISM: Artificial Sequence
<220> FEATURE:
<223> OTHER INFORMATION: Synthetic peptide

<400> SEQUENCE: 169

His Leu Ala His Leu Ala His His Leu Lys Leu Ala Lys Leu Ala Lys
1               5                   10                  15

Val Arg Arg Ala Asp Asn Arg Pro Gly
            20                  25

<210> SEQ ID NO 170
<211> LENGTH: 24
<212> TYPE: PRT
<213> ORGANISM: Artificial Sequence
<220> FEATURE:
<223> OTHER INFORMATION: Synthetic peptide

<400> SEQUENCE: 170

His Leu Ala His Leu Ala His His Lys Leu Ala Lys Leu Ala Lys Val
1               5                   10                  15

Arg Arg Ala Asp Asn Arg Pro Gly
            20

<210> SEQ ID NO 171
<211> LENGTH: 23
<212> TYPE: PRT
<213> ORGANISM: Artificial Sequence
<220> FEATURE:
<223> OTHER INFORMATION: Synthetic peptide

<400> SEQUENCE: 171

His Leu Ala His Leu Ala His Lys Leu Ala Lys Leu Ala Lys Val Arg
1               5                   10                  15

Arg Ala Asp Asn Arg Pro Gly
            20
```

COMPOSITIONS AND METHODS FOR TARGETED ENDOMETRIOSIS TREATMENT

CROSS-REFERENCE TO RELATED APPLICATIONS

This application is a 371 application of International Application No. PCT/US2014/041912, filed Jun. 11, 2014, which claims benefit of U.S. Provisional Application No. 61/833,519, entitled "Compositions and Methods for Targeted Endometriosis Treatment" by Michiko Fukuda and Kazuhiro Sugihara, filed Jun. 11, 2013, all of which are herein incorporated by reference.

STATEMENT REGARDING FEDERALLY SPONSORED RESEARCH

This invention was made with government support under Grant HD43108 from the National Institutes of Health (NIH) and Grant W81XWH-04-1-0917 from the Department of Defense (DoD). The government has certain rights in the invention.

BACKGROUND

Endometriosis is a commonly encountered gynecologic disease requiring medical or surgical therapy. As many as 6 to 10% of women of reproductive age are considered affected by this disease (Houston, 1984; Sensky and Liu, 1980). Although endometriosis can appear benign and its symptoms usually disappear in post-menopausal women, resultant infertility and severe, disabling pain significantly diminish patients' quality of life (Farquhar, 2000; Murphy, 2002). In developing countries the number of endometriosis patients is increasing (Bruner-Tran et al., 1999; Osteen and Sierra-Rivera, 1997; Rier and Foster, 2002; Rier, 2002).

Endometriosis occurs only in higher primates, including humans and baboons. Spontaneous endometriosis reportedly occurs in about 25% of captive baboons, and its prevalence increases with captivity duration (D'Hooghe, 1997). Experiments in non-human primates show a clear positive correlation between endometriosis and a diet containing the chemical dioxin (Rier et al., 1993; Rier et al., 2001), which may promote endometriosis by acting as an estrogen-like factor. In patients with endometriosis, many of the pathologic processes including inflammation, the immune response, angiogenesis and apoptosis are all favored for promoting endometriosis in a manner dependent on steroid hormones (Giudice and Kao, 2004; Osteen and Sierra-Rivera, 1997). Thus, in the past most treatment was via therapeutics targeting steroid hormones and their receptors (Hayes and Rock, 2002; Olive and Pritts, 2001). These drugs can only be administered for a short term due to side effects. Current first-line therapy is oral contraceptive pills (OCPs), which halt an ovulation and suppress endometriosis tissue growth with minimum side effects (Amsterdam et al., 2005). OCPs are also administered with nonsteroidal anti-inflammatory drugs (NSAIDs), further reducing endometriosis-associated pain (Johnson and Farquhar, 2006; Vercellini et al., 2003). Nonetheless these treatments do not remove endometriosis, and patients with severe symptoms must undergo surgery. However, even then symptoms can recur, requiring multiple surgeries in many cases (Vercellini et al., 2009). Thus it is critical to develop new strategies to cure this disease.

BRIEF SUMMARY

Disclosed are compositions comprising a targeting peptide that selectively binds an endometriosis cell. Disclosed herein are compositions and methods for specifically targeting endometriosis cells. Also disclosed are endosome escape peptides, compositions containing endosome escape peptides, and methods of using endosome escape peptides to treat subjects. Also disclosed are antibodies to specific for cyclic nucleotide-gated channel beta 3 (CNGB3), antibodies specific for an epitope of cyclic nucleotide-gated channel beta 3 (CNGB3), and methods of using such antibodies.

Also disclosed are compositions comprising an endosome escape signal and a targeting peptide that selectively binds an endometriosis cell. The endosome escape signal can comprise an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38).

Also disclosed are compositions comprising an effector molecule and a targeting peptide that selectively binds an endometriosis cell. In some forms, the effector molecule can comprise a peptide, apoptosis-inducing compound, apoptosis-inducing peptide, small molecule, pharmaceutical drug, toxin, fatty acid, detectable marker, conjugating tag, nanoparticle, or enzyme. Where the erector molecule is a peptide it can be referred to as an effector peptide. In some forms, the effector molecule can comprise an apoptosis-inducing peptide. In some forms, the apoptosis-inducing peptide can comprise two or more KLAKLAK sequences (SEQ ID NO:39). In some forms, the apoptosis-inducing peptide can comprise the sequence KLAKLAKKLAKLAKKLAK (SEQ ID NO:40). In some forms, the apoptosis-inducing peptide can comprise (KLAKLAK)$_2$ (SEQ ID NO:26).

In some forms, the targeting peptide can bind to cyclic nucleotide-gated channel beta 3 (CNGB3). In some forms, the targeting peptide can bind to an epitope of CNGB3 comprising the amino acid sequence SEQ ID NO:32. In some forms, the targeting peptide can comprise the amino acid sequence set forth in SEQ ID NO:1. In some forms, the targeting peptide can comprise the amino acid sequence set forth in SEQ ID NO:2, 3 or 4.

Also disclosed are methods comprising administering to a subject a composition comprising a targeting peptide that selectively binds an endometriosis cell.

Also disclosed are methods of targeting an endometriosis cell in a subject, the method comprising administering to the subject a composition comprising a targeting peptide that selectively binds an endometriosis cell.

Also disclosed are methods of treating a subject suffering endometriosis, the method comprising administering to the subject a composition comprising an endosome escape signal and a targeting peptide that selectively binds an endometriosis cell, thereby treating the subject. The endosome escape signal can comprise an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38).

The composition can further comprise an effector molecule. In some forms, the effector molecule can comprise a peptide, apoptosis-inducing compound, apoptosis-inducing peptide, small molecule, pharmaceutical drug, toxin, fatty acid, detectable marker, conjugating tag, nanoparticle, or enzyme. In some form, the effector molecule can comprise an apoptosis-inducing peptide. In some forms, the apoptosis-inducing peptide can comprise two or more KLAKLAK sequences (SEQ ID NO:39). In some forms, the apoptosis-inducing peptide can comprise the sequence KLAKLAK-KLAKLAKKLAK (SEQ ID NO:40).

Also disclosed are antibodies, wherein the antibody is specific for the cyclic nucleotide-gated channel beta 3 (CNGB3). Also disclosed are antibodies, wherein the antibody is specific for an epitope comprising the amino acid sequence SEQ ID NO:32.

Also disclosed are methods comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both. The subject can comprise a cell, wherein the cell is an endometriosis cell.

Also disclosed are methods of detecting endometriosis in a subject, the method comprising administering to the subject a composition comprising a targeting peptide that selectively binds an endometriosis cell and detecting the composition in the subject, thereby detecting endometriosis.

Also disclosed are methods of diagnosing endometriosis in a subject, the method comprising administering to the subject a composition comprising a targeting peptide that selectively binds an endometriosis cell and detecting the composition in the subject, thereby diagnosing endometriosis in the subject.

Also disclosed are methods of determining the prognosis of endometriosis in a subject, the method comprising administering to the subject a composition comprising a targeting peptide that selectively binds an endometriosis cell and detecting the composition in the subject, wherein the level, amount, concentration, or a combination of binding of the composition to endometriosis tissue in the subject indicates the prognosis of the endometriosis in the subject.

Also disclosed are methods of determining the progress of endometriosis in a subject, the method comprising administering to the subject a composition comprising a targeting peptide that selectively binds an endometriosis cell, detecting the composition in the subject, and repeating the administration and detection at a later time, wherein a change in the level, amount, concentration, or a combination of binding of the composition to endometriosis tissue in the subject indicates the progress of the endometriosis in the subject.

Also disclosed are methods of determining the progress of treatment of endometriosis in a subject, the method comprising administering to the subject a composition comprising a targeting peptide that selectively binds an endometriosis cell, detecting the composition in the subject, and repeating the administration and detection following treatment, wherein a change in the level, amount, concentration, or a combination of binding of the composition to endometriosis tissue in the subject indicates the progress the treatment of the endometriosis in the subject.

Additional advantages of the disclosed methods and compositions will be set forth in part in the description which follows, and in part will be understood from the description, or may be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed methods and compositions.

DETAILED DESCRIPTION

Figure 1:
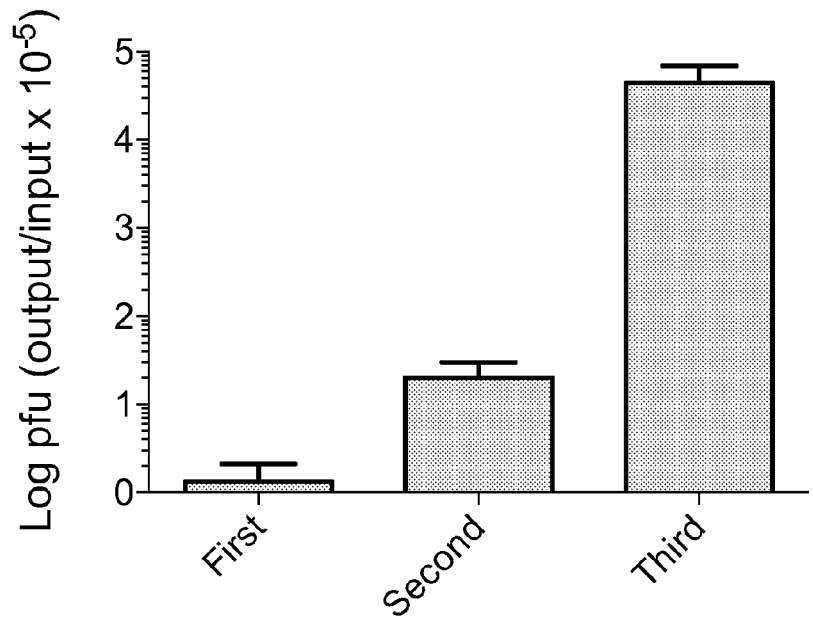
FIG. 1 is a graph of plaque forming units (log pfu) of phage selected over three rounds of subtractive phage library screening resulting in identification of endometriosis-targeting peptides. Binding efficiency of phage pools obtained after each screening round was assessed by plaque forming assay.

The disclosed methods and compositions may be understood more readily by reference to the following detailed description of particular embodiments and the Example included herein and to the Figures and their previous and following description.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

One proposed cause for endometriosis is through retrograde menstrual reflux of the endometrium which becomes implanted in regions of the pelvis (Vinatier et al., 2001), most commonly on the ovaries and areas facing the peritoneum (Shampson, 1940; Vinatier et al., 2001). It was discovered that a molecule specifically expressed on the endometrial surface is not expressed by other peritoneal surfaces and can be targeted by a peritoneally-injected drug. A 9-mer peptide that specifically binds to glandular epithelial cells of endometriosis in peritoneum was also discovered. The receptor of this peptide was also discovered as the cyclic nucleotide gated channel β3 (CNGB3). Expression in endometriosis of CNGB3 was confirmed. Based on these findings, therapeutics for peritoneal endometriosis were developed and their activity tested successfully in baboon endometriosis models.

Disclosed are compositions comprising an endosome escape signal and a targeting peptide that selectively binds an endometriosis cell. In some forms, the endosome escape molecule can comprise an endosome escape peptide. Also disclosed are nucleic acids comprising a nucleic acid sequence encoding an endosome escape peptide and a targeting peptide that selectively binds an endometriosis cell. Also disclosed are compositions comprising an effector molecule and a targeting peptide that selectively binds an endometriosis cell. In some forms, the effector molecule can comprise an apoptosis-inducing peptide. Also disclosed are nucleic acids comprising a nucleic acid sequence encoding an effector molecule and a targeting peptide that selectively binds an endometriosis cell. Also disclosed are compositions comprising an endosome escape signal, an effector molecule, and a targeting peptide that selectively binds an endometriosis cell. In some forms, the endosome escape molecule can comprise an endosome escape peptide and the effector molecule can comprise an apoptosis-inducing peptide. Also disclosed are nucleic acids comprising a nucleic acid sequence encoding an endosome escape signal, an effector molecule, and a targeting peptide that selectively binds an endometriosis cell. Also disclosed are nucleic acids comprising a nucleic acid sequence encoding an endosome escape peptide, an apoptosis-inducing peptide, and a targeting peptide that selectively binds an endometriosis cell. Also disclosed are CNGB3 as the peritoneal endosome specific receptor for drug targeting.

In some forms, the compositions comprise two peptides. In some forms, the first peptide can comprise an endosome escape signal and a targeting peptide that selectively binds an endometriosis cell. In some forms, the second peptide can comprise an effector molecule and a second targeting peptide that selectively binds an endometriosis cell. In some forms, the endosome escape molecule can comprise an apoptosis-inducing peptide. Also disclosed are compositions comprising an endosome escape signal, an effector molecule, and a targeting peptide that selectively binds an endometriosis cell. Also disclosed are nucleic acids comprising a nucleic acid sequence encoding an endosome escape signal, an effector molecule, and a targeting peptide that selectively binds an endometriosis cell. Also disclosed are peptides targeting receptor CNGB3.

In some forms, the compositions can comprise two components that are not covalently coupled to each other. In some forms, the compositions can comprise two components that are non-covalently associated with each other. In some forms, the compositions can comprise two components that are not covalently couple or non-covalently associated with each other. In some forms, the first component can comprise an endosome escape signal and a targeting peptide that selectively binds an endometriosis cell. In some forms, the second component can comprise an effector molecule and a second targeting peptide that selectively binds an endometriosis cell. The first component and/or second component can be peptides and/or can comprise peptides.

In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38). In some forms, the endosome escape peptide can comprise HLAHLAHH (amino acids 1 to 8 of SEQ ID NO:38), HLAHLAHHL (amino acids 1 to 9 of SEQ ID NO:38), HLAHLAHHLA (amino acids 1 to 10 of SEQ ID NO:38), HLAHLAHHLAH (amino acids 1 to 11 of SEQ ID NO:38), HLAHLAHHLAHL (amino acids 1 to 12 of SEQ ID NO:38), HLAHLAHHLAHLA (amino acids 1 to 13 of SEQ ID NO:38), or HLAHLAHHLAHLAH (amino acids 1 to 14 of SEQ ID NO:38).

In some form, the effector molecule can comprise an apoptosis-inducing peptide. In some forms, the apoptosis-inducing peptide can comprise two or more KLAKLAK sequences (SEQ ID NO:39). In some forms, the apoptosis-inducing peptide can comprise the sequence KLAKLAKKLAKLAKKLAK (SEQ ID NO:40). In some forms, the apoptosis-inducing peptide can comprise $(KLAKLAK)_2$ (SEQ ID NO:26). In some forms, the effector molecule can comprise KLAKLAKK (amino acids 1 to 8 of SEQ ID NO:40), KLAKLAKKL (amino acids 1 to 9 of SEQ ID NO:40), KLAKLAKKLA (amino acids 1 to 10 of SEQ ID NO:40), KLAKLAKKLAK (amino acids 1 to 11 of SEQ ID NO:40), KLAKLAKKLAKL (amino acids 1 to 12 of SEQ ID NO:40), KLAKLAKKLAKLA (amino acids 1 to 13 of SEQ ID NO:40), or KLAKLAKKLAKLAK (amino acids 1 to 14 of SEQ ID NO:40).

In some forms, the targeting peptide can bind to cyclic nucleotide-gated channel beta 3 (CNGB3). In some forms, the targeting peptide can bind to CNGB3. In some forms, the targeting peptide can comprise the amino acid sequence set forth in SEQ ID NO:1. In some forms, the targeting peptide can comprise the amino acid sequence set forth in SEQ ID NO:2, 3 or 4.

Also disclosed are methods comprising administering to a subject the composition or nucleic acid.

The subject can comprise a cell, wherein the cell is an endometriosis cell. The nucleic acid can be expressed in a cell, wherein the nucleic acid is administered to the subject by administering the cell to the subject. The cell can be a cell from the subject, wherein the nucleic acid is introduced to the cell ex vivo.

The endosome escape signal can be an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38). The endosome escape signal can be covalently linked to the targeting peptide. The endosome escape signal can be linked to the amino terminal end of the targeting peptide. The endosome escape signal can be linked to the carboxy terminal end of the targeting peptide. The endosome escape signal can be linked to an amino acid within the targeting peptide. The composition can further comprise a linker connecting the endosome escape signal and targeting peptide. The composition can further comprise an effector molecule.

The composition can comprise a peptide, wherein the peptide comprises the endosome escape peptide and the targeting peptide. The peptide can comprise the amino acid sequence of SEQ ID NO:28. The peptide can comprise the amino acid sequence of SEQ ID NO:30. The peptide can comprise the amino acid sequence of SEQ ID NO:35. The peptide can comprise the amino acid sequence of SEQ ID NO:36.

The effector molecule can be a peptide, apoptosis-inducing compound, apoptosis-inducing peptide, small molecule, pharmaceutical drug, toxin, fatty acid, detectable marker, conjugating tag, nanoshell, or enzyme. In some forms, the apoptosis-inducing peptide can comprise two or more KLAKLAK sequences (SEQ ID NO:39). In some forms, the apoptosis-inducing peptide can comprise the sequence KLAKLAKKLAKLAKKLAK (SEQ ID NO:40). In some forms, the apoptosis-inducing peptide can comprise $(KLAKLAK)_2$ (SEQ ID NO:26). The effector molecule can be covalently linked to the targeting peptide. The effector molecule can be linked to the amino terminal end of the targeting peptide. The effector molecule can be linked to the carboxy terminal end of the targeting peptide. The effector molecule can be linked to an amino acid within the targeting peptide. The composition can further comprise a linker connecting the effector molecule and targeting peptide. The composition can further comprise an endosome escape signal. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38).

The composition can comprise a peptide, wherein the peptide comprises the effector molecule and the targeting peptide. The peptide can comprise the amino acid sequence of SEQ ID NO:41. The peptide can comprise the amino acid sequence of SEQ ID NO:42. In some forms, the peptide comprises the endosome escape signal, the effector molecule, and the targeting peptide. In some forms, the endosome escape signal is N-terminal to the effector molecule and the targeting peptide. In some forms, the effector molecule is N-terminal to the targeting peptide. In some forms, the targeting peptide is N-terminal to the effector molecule. In some forms, the effector molecule is N-terminal to the endosome escape signal and the targeting peptide. In some forms, the endosome escape molecule is N-terminal to the targeting peptide. In some forms, the targeting peptide is N-terminal to the endosome escape molecule. In some forms, the targeting peptide is N-terminal to the effector molecule and the endosome escape signal. In some forms, the effector molecule is N-terminal to the endosome escape signal. In some forms, the endosome escape signal is N-terminal to the effector molecule.

Examples of such chimeric or hybrid peptides include peptides of the formula $X_7$-$X_8$-$X_9$, $X_8$-$X_7$-$X_9$, $X_7$-$X_9$-$X_8$, $X_8$-$X_9$-$X_7$, $X_9$-$X_7$-$X_8$, and $X_9$-$X_8$-$X_7$, where $X_7$ is effector molecule, $X_8$ is the endosome escape signal, and $X_9$ is the targeting peptide. Examples of the effector molecule include sequences KLAKLAK (SEQ ID NO:39), $(KLAKLAK)_2$ (SEQ ID NO:26), KLAKLAKK (amino acids 1 to 8 of SEQ ID NO:40), KLAKLAKKL (amino acids 1 to 9 of SEQ ID NO:40), KLAKLAKKLA (amino acids 1 to 10 of SEQ ID NO:40), KLAKLAKKLAK (amino acids 1 to 11 of SEQ ID NO:40), KLAKLAKKLAKL (amino acids 1 to 12 of SEQ ID NO:40), KLAKLAKKLAKLA (amino acids 1 to 13 of SEQ ID NO:40), KLAKLAKKLAKLAK (amino acids 1 to 14 of SEQ ID NO:40), and KLAKLAKKLAKLAKKLAK (SEQ ID NO:40).

Examples of the endosome escape signal include sequences HLAHLAH (SEQ ID NO:37), HLAHLAHH (amino acids 1 to 8 of SEQ ID NO:38), HLAHLAHHL (amino acids 1 to 9 of SEQ ID NO:38), HLAHLAHHLA (amino acids 1 to 10 of SEQ ID NO:38), HLAHLAHHLAH (amino acids 1 to 11 of SEQ ID NO:38), HLAHLAH-HLAHL (amino acids 1 to 12 of SEQ ID NO:38), HLAHL-AHHLAHLA (amino acids 1 to 13 of SEQ ID NO:38), HLAHLAHHLAHLAH (amino acids 1 to 14 of SEQ ID NO:38), and HLAHLAHHLAHLAHHLAH (SEQ ID NO:38).

Examples of the targeting peptide include sequences VRRAXNXPG (SEQ ID NO:1), VRRANNLPG (SEQ ID NO:2), VRRADNRPG (SEQ ID NO:3), and VRRANNRPG (SEQ ID NO:4).

Examples of peptides comprising an endosome escape signal, an effector molecule, and a targeting peptide include the following sequences:

```
(SEQ ID NO: 45)
KLAKLAKKLAKLAKHLAHLAHHLAHLAHVRRADNRPG;

(SEQ ID NO: 46)
KLAKLAKKLAKLAHLAHLAHHLAHLAHVRRADNRPG;

(SEQ ID NO: 47)
KLAKLAKKLAKLHLAHLAHHLAHLAHVRRADNRPG;

(SEQ ID NO: 48)
KLAKLAKKLAKHLAHLAHHLAHLAHVRRADNRPG;

(SEQ ID NO: 49)
KLAKLAKKLAHLAHLAHHLAHLAHVRRADNRPG;

(SEQ ID NO: 50)
KLAKLAKKLHLAHLAHHLAHLAHVRRADNRPG;

(SEQ ID NO: 51)
KLAKLAKKHLAHLAHHLAHLAHVRRADNRPG;

(SEQ ID NO: 52)
KLAKLAKHLAHLAHHLAHLAHVRRADNRPG;

(SEQ ID NO: 53)
HLAHLAHHLAHLAHKLAKLAKKLAKLAKVRRADNRPG;

(SEQ ID NO: 54)
HLAHLAHHLAHLAKLAKLAKKLAKLAKVRRADNRPG;

(SEQ ID NO: 55)
HLAHLAHHLAHLKLAKLAKKLAKLAKVRRADNRPG;

(SEQ ID NO: 56)
HLAHLAHHLAHKLAKLAKKLAKLAKVRRADNRPG;

(SEQ ID NO: 57)
HLAHLAHHLAKLAKLAKKLAKLAKVRRADNRPG;

(SEQ ID NO: 58)
HLAHLAHHLKLAKLAKKLAKLAKVRRADNRPG;

(SEQ ID NO: 59)
HLAHLAHHKLAKLAKKLAKLAKVRRADNRPG;
```

-continued

```
(SEQ ID NO: 60)
HLAHLAHKLAKLAKKLAKLAKVRRADNRPG;

(SEQ ID NO: 61)
KLAKLAKKLAKLAKHLAHLAHHLAHLAVRRADNRPG;

(SEQ ID NO: 62)
KLAKLAKKLAKLAHLAHLAHHLAHLAVRRADNRPG;

(SEQ ID NO: 63)
KLAKLAKKLAKLHLAHLAHHLAHLAVRRADNRPG;

(SEQ ID NO: 64)
KLAKLAKKLAKHLAHLAHHLAHLAVRRADNRPG;

(SEQ ID NO: 65)
KLAKLAKKLAHLAHLAHHLAHLAVRRADNRPG;

(SEQ ID NO: 66)
KLAKLAKKLHLAHLAHHLAHLAVRRADNRPG;

(SEQ ID NO: 67)
KLAKLAKKHLAHLAHHLAHLAVRRADNRPG;

(SEQ ID NO: 68)
KLAKLAKHLAHLAHHLAHLAVRRADNRPG;

(SEQ ID NO: 69)
HLAHLAHHLAHLAHKLAKLAKKLAKLAVRRADNRPG;

(SEQ ID NO: 70)
HLAHLAHHLAHLAKLAKLAKKLAKLAVRRADNRPG;

(SEQ ID NO: 71)
HLAHLAHHLAHLKLAKLAKKLAKLAVRRADNRPG;

(SEQ ID NO: 72)
HLAHLAHHLAHKLAKLAKKLAKLAVRRADNRPG;

(SEQ ID NO: 73)
HLAHLAHHLAKLAKLAKKLAKLAVRRADNRPG;

(SEQ ID NO: 74)
HLAHLAHHLKLAKLAKKLAKLAVRRADNRPG;

(SEQ ID NO: 75)
HLAHLAHHKLAKLAKKLAKLAVRRADNRPG;

(SEQ ID NO: 76)
HLAHLAHKLAKLAKKLAKLAVRRADNRPG;

(SEQ ID NO: 77)
KLAKLAKKLAKLAKHLAHLAHHLAHLVRRADNRPG;

(SEQ ID NO: 78)
KLAKLAKKLAKLAHLAHLAHHLAHLVRRADNRPG;

(SEQ ID NO: 79)
KLAKLAKKLAKLHLAHLAHHLAHLVRRADNRPG;

(SEQ ID NO: 80)
KLAKLAKKLAKHLAHLAHHLAHLVRRADNRPG;

(SEQ ID NO: 81)
KLAKLAKKLAHLAHLAHHLAHLVRRADNRPG;

(SEQ ID NO: 82)
KLAKLAKKLHLAHLAHHLAHLVRRADNRPG;

(SEQ ID NO: 83)
KLAKLAKKHLAHLAHHLAHLVRRADNRPG;

(SEQ ID NO: 84)
KLAKLAKHLAHLAHHLAHLVRRADNRPG;

(SEQ ID NO: 85)
HLAHLAHHLAHLAHKLAKLAKKLAKLVRRADNRPG;

(SEQ ID NO: 86)
HLAHLAHHLAHLAKLAKLAKKLAKLVRRADNRPG;
```

-continued

```
                                      (SEQ ID NO: 87)
HLAHLAHHLAHLKLAKLAKKLAKLVRRADNRPG;

(SEQ ID NO: 88)
HLAHLAHHLAHKLAKLAKKLAKLVRRADNRPG;

(SEQ ID NO: 89)
HLAHLAHHLAKLAKLAKKLAKLVRRADNRPG;

(SEQ ID NO: 90)
HLAHLAHHLKLAKLAKKLAKLVRRADNRPG;

(SEQ ID NO: 91)
HLAHLAHHKLAKLAKKLAKLVRRADNRPG;

(SEQ ID NO: 92)
HLAHLAHKLAKLAKKLAKLVRRADNRPG;

(SEQ ID NO: 93)
KLAKLAKKLAKLAKHLAHLAHHLAHVRRADNRPG;

(SEQ ID NO: 94)
KLAKLAKKLAKLAHLAHLAHHLAHVRRADNRPG;

(SEQ ID NO: 95)
KLAKLAKKLAKLHLAHLAHHLAHVRRADNRPG;

(SEQ ID NO: 96)
KLAKLAKKLAKHLAHLAHHLAHVRRADNRPG;

(SEQ ID NO: 97)
KLAKLAKKLAHLAHLAHHLAHVRRADNRPG;

(SEQ ID NO: 98)
KLAKLAKKLHLAHLAHHLAHVRRADNRPG;

(SEQ ID NO: 99)
KLAKLAKKHLAHLAHHLAHVRRADNRPG;

(SEQ ID NO: 100)
KLAKLAKHLAHLAHHLAHVRRADNRPG;

(SEQ ID NO: 101)
HLAHLAHHLAHLAHKLAKLAKKLAKVRRADNRPG;

(SEQ ID NO: 102)
HLAHLAHHLAHLAKLAKLAKKLAKVRRADNRPG;

(SEQ ID NO: 103)
HLAHLAHHLAHLKLAKLAKKLAKVRRADNRPG;

(SEQ ID NO: 104)
HLAHLAHHLAHKLAKLAKKLAKVRRADNRPG;

(SEQ ID NO: 105)
HLAHLAHHLAKLAKLAKKLAKVRRADNRPG;

(SEQ ID NO: 106)
HLAHLAHHLKLAKLAKKLAKVRRADNRPG;

(SEQ ID NO: 407)
HLAHLAHHKLAKLAKKLAKVRRADNRPG;

(SEQ ID NO: 108)
HLAHLAHKLAKLAKKLAKVRRADNRPG;

(SEQ ID NO: 109)
KLAKLAKKLAKLAKHLAHLAHHLAVRRADNRPG;

(SEQ ID NO: 110)
KLAKLAKKLAKLAHLAHLAHHLAVRRADNRPG;

(SEQ ID NO: 111)
KLAKLAKKLAKLHLAHLAHHLAVRRADNRPG;

(SEQ ID NO: 112)
KLAKLAKKLAKHLAHLAHHLAVRRADNRPG;

(SEQ ID NO: 113)
KLAKLAKKLAHLAHLAHHLAVRRADNRPG;

(SEQ ID NO: 114)
KLAKLAKKLHLAHLAHHLAVRRADNRPG;

(SEQ ID NO: 115)
KLAKLAKKHLAHLAHHLAVRRADNRPG;

(SEQ ID NO: 116)
KLAKLAKHLAHLAHHLAVRRADNRPG;

(SEQ ID NO: 117)
HLAHLAHHLAHLAHKLAKLAKKLAVRRADNRPG;

(SEQ ID NO: 118)
HLAHLAHHLAHLAKLAKLAKKLAVRRADNRPG;

(SEQ ID NO: 119)
HLAHLAHHLAHLKLAKLAKKLAVRRADNRPG;

(SEQ ID NO: 120)
HLAHLAHHLAHKLAKLAKKLAVRRADNRPG;

(SEQ ID NO: 121)
HLAHLAHHLAKLAKLAKKLAVRRADNRPG;

(SEQ ID NO: 122)
HLAHLAHHLKLAKLAKKLAVRRADNRPG;

(SEQ ID NO: 123)
HLAHLAHHKLAKLAKKLAVRRADNRPG;

(SEQ ID NO: 124)
HLAHLAHKLAKLAKKLAVRRADNRPG;

(SEQ ID NO: 125)
KLAKLAKKLAKLAKHLAHLAHHLVRRADNRPG;

(SEQ ID NO: 126)
KLAKLAKKLAKLAHLAHLAHHLVRRADNRPG;

(SEQ ID NO: 127)
KLAKLAKKLAKLHLAHLAHHLVRRADNRPG;

(SEQ ID NO: 128)
KLAKLAKKLAKHLAHLAHHLVRRADNRPG;

(SEQ ID NO: 129)
KLAKLAKKLAHLAHLAHHLVRRADNRPG;

(SEQ ID NO: 130)
KLAKLAKKLHLAHLAHHLVRRADNRPG;

(SEQ ID NO: 131)
KLAKLAKKHLAHLAHHLVRRADNRPG;

(SEQ ID NO: 132)
KLAKLAKHLAHLAHHLVRRADNRPG;

(SEQ ID NO: 133)
HLAHLAHHLAHLAHKLAKLAKKLVRRADNRPG;

(SEQ ID NO: 134)
HLAHLAHHLAHLAKLAKLAKKLVRRADNRPG;

(SEQ ID NO: 135)
HLAHLAHHLAHLKLAKLAKKLVRRADNRPG;

(SEQ ID NO: 136)
HLAHLAHHLAHKLAKLAKKLVRRADNRPG;

(SEQ ID NO: 137)
HLAHLAHHLAKLAKLAKKLVRRADNRPG;

(SEQ ID NO: 138)
HLAHLAHHLKLAKLAKKLVRRADNRPG;

(SEQ ID NO: 139)
HLAHLAHHKLAKLAKKLVRRADNRPG;

(SEQ ID NO: 140)
HLAHLAHKLAKLAKKLVRRADNRPG;
```

KLAKLAKKLAKLAKHLAHLAHHVRRADNRPG; (SEQ ID NO: 141)

KLAKLAKKLAKLAHLAHLAHHVRRADNRPG; (SEQ ID NO: 142)

KLAKLAKKLAKLHLAHLAHHVRRADNRPG; (SEQ ID NO: 143)

KLAKLAKKLAKHLAHLAHHVRRADNRPG; (SEQ ID NO: 144)

KLAKLAKKLAHLAHLAHHVRRADNRPG; (SEQ ID NO: 145)

KLAKLAKKLHLAHLAHHVRRADNRPG; (SEQ ID NO: 146)

KLAKLAKKHLAHLAHHVRRADNRPG; (SEQ ID NO: 147)

KLAKLAKHLAHLAHHVRRADNRPG; (SEQ ID NO: 148)

HLAHLAHHLAHLAHKLAKLAKKVRRADNRPG; (SEQ ID NO: 149)

HLAHLAHHLAHLAKLAKLAKKVRRADNRPG; (SEQ ID NO: 150)

HLAHLAHHLAHLKLAKLAKKVRRADNRPG; (SEQ ID NO: 151)

HLAHLAHHLAHKLAKLAKKVRRADNRPG; (SEQ ID NO: 152)

HLAHLAHHLAKLAKLAKKVRRADNRPG; (SEQ ID NO: 153)

HLAHLAHHLKLAKLAKKVRRADNRPG; (SEQ ID NO: 154)

HLAHLAHHKLAKLAKKVRRADNRPG; (SEQ ID NO: 155)

HLAHLAHKLAKLAKKVRRADNRPG; (SEQ ID NO: 156)

KLAKLAKKLAKLAKHLAHLAHVRRADNRPG; (SEQ ID NO: 157)

KLAKLAKKLAKLAHLAHLAHVRRADNRPG; (SEQ ID NO: 158)

KLAKLAKKLAKLHLAHLAHVRRADNRPG; (SEQ ID NO: 159)

KLAKLAKKLAKHLAHLAHVRRADNRPG; (SEQ ID NO: 160)

KLAKLAKKLAHLAHLAHVRRADNRPG; (SEQ ID NO: 161)

KLAKLAKKLHLAHLAHVRRADNRPG; (SEQ ID NO: 162)

KLAKLAKKHLAHLAHVRRADNRPG; (SEQ ID NO: 163)

KLAKLAKHLAHLAHVRRADNRPG; (SEQ ID NO: 164)

HLAHLAHHLAHLAHKLAKLAKVRRADNRPG; (SEQ ID NO: 165)

HLAHLAHHLAHLAKLAKLAKVRRADNRPG; (SEQ ID NO: 166)

HLAHLAHHLAHLKLAKLAKVRRADNRPG; (SEQ ID NO: 167)

HLAHLAHHLAHKLAKLAKVRRADNRPG; (SEQ ID NO: 168)

HLAHLAHHLAKLAKLAKVRRADNRPG; (SEQ ID NO: 169)

HLAHLAHHLKLAKLAKVRRADNRPG; (SEQ ID NO: 170)

HLAHLAHHKLAKLAKVRRADNRPG; (SEQ ID NO: 171)
and

HLAHLAHKLAKLAKVRRADNRPG. (SEQ ID NO: 172)

The targeting peptide comprises at least 9 amino acids, wherein the targeting peptide has at least 70% sequence identity with SEQ ID NO:1. The targeting peptide can comprise at least 9 amino acids, wherein the targeting peptide has at least 80% sequence identity with SEQ ID NO:1. The targeting peptide can comprise at least 9 amino acids, wherein the targeting peptide can have at least 90% sequence identity with SEQ ID NO:1. The targeting peptide can have at least 65% sequence identity to the amino acid sequence set forth in SEQ ID NO:2, 3, or 4. The targeting peptide can have at least 75% sequence identity to the amino acid sequence set forth in SEQ ID NO:2, 3, or 4. The targeting peptide can have at least 85% sequence identity to the amino acid sequence set forth in SEQ ID NO:2, 3, or 4. The targeting peptide can comprise an amino acid segment of at least 6 consecutive amino acids having at least 65% sequence identity to the amino acid sequence set forth in SEQ ID NO:2, 3, or 4. The targeting peptide can comprise an amino acid segment of at least 6 consecutive amino acids having at least 75% sequence identity to the amino acid sequence set forth in SEQ ID NO:2, 3, or 4. The targeting peptide can comprise an amino acid segment of at least 6 consecutive amino acids having at least 85% sequence identity to the amino acid sequence set forth in SEQ ID NO:2, 3, or 4. The targeting peptide can comprise an amino acid segment of at least 6 consecutive amino acids having the amino acid sequence set forth in SEQ ID NO:2, 3, or 4. The amino acid segment can consist essentially of nine consecutive amino acids.

Any variation of the targeting peptide from SEQ ID NO:1 can be a conservative amino acid substitution. Any variation of the targeting peptide from SEQ ID NO:2, 3, or 4 can be a conservative amino acid substitution. The targeting peptide can comprise at least 6 amino acids. The targeting peptide can comprise at least 7 amino acids. The targeting peptide can comprise at least 8 amino acids. The targeting peptide can comprise at least 9 amino acids. The targeting peptide can comprise the amino acid sequence set forth in SEQ ID NO:1. The targeting peptide can comprise the amino acid sequence set forth in SEQ ID NO:2, 3 or 4.

The composition can further comprise a progestational agent. The composition can further comprise a Gonadotropin-releasing hormone (GnRH), GnRH analog, or GnRH agonist. The composition can further comprise an aromatase inhibitor. The composition can further comprise a narcotic. The composition can further comprise a non-steroidal anti-inflammatory drug (NSAID). The composition can further comprise a pharmaceutically acceptable carrier.

The nucleic acid can further encode an endosome escape signal. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAH-HLAH (SEQ ID NO:38). The nucleic acid can encode a peptide, wherein the peptide comprises the endosome escape peptide and the targeting peptide. The peptide can comprise the amino acid sequence of SEQ ID NO:28. The peptide can comprise the amino acid sequence of SEQ ID NO:30. The peptide can comprise the amino acid sequence of SEQ ID NO:35. The peptide can comprise the amino acid sequence of SEQ ID NO:36.

The nucleic acid sequence encoding the effector molecule can be 5' to the nucleic acid sequence encoding the targeting peptide. The nucleic acid sequence encoding the effector molecule can be 3' to the nucleic acid sequence encoding the targeting peptide. The nucleic acid can encode a fusion protein comprising the targeting peptide and the effector molecule. The nucleic acid sequence encoding the endosome escape signal can be 5' to the nucleic acid sequence encoding the targeting peptide. The nucleic acid sequence encoding the endosome escape signal can be 3' to the nucleic acid sequence encoding the targeting peptide. The nucleic acid can encode a fusion protein comprising the targeting peptide and the endosome escape signal. The nucleic acid sequence encoding the endosome escape signal can be 5' to the nucleic acid sequence encoding the targeting peptide and the effector molecule. The nucleic acid sequence encoding the endosome escape signal can be 3' to the nucleic acid sequence encoding the targeting peptide and the effector molecule. The nucleic acid can encode a fusion protein comprising the targeting peptide, the effector molecule and the endosome escape signal. The nucleic acid sequence encoding the effector molecule can be 5' to the nucleic acid sequence encoding the targeting peptide and the endosome escape signal. The nucleic acid sequence encoding the effector molecule can be 3' to the nucleic acid sequence encoding the targeting peptide and the endosome escape signal.

Disclosed are antibodies, wherein the antibody is specific for cyclic nucleotide-gated channel beta 3 (CNGB3). Also disclosed are antibodies, wherein the antibody is specific for an epitope comprising the amino acid sequence SEQ ID NO:32.

Disclosed are methods comprising administering to a subject an antibody, wherein an antibody is specific for the cyclic nucleotide-gated channel beta 3 (CNGB3), wherein the antibody is specific for an epitope comprising the amino acid sequence SEQ ID NO:32, or both. The subject can comprise a cell, wherein the cell is an endometriosis cell. Also disclosed are methods of targeting, detecting, inhibiting, killing, or a combination cells expressing CNGB3. Also disclosed are methods of targeting, detecting, inhibiting, killing, or a combination endometriosis cells.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

The terms "targeting" or "homing", as used herein can refer to the preferential movement, binding and/or accumulation of a targeted compound or composition, such as the disclosed compositions, at a site or a location as compared to a non-targeted compound or composition. For example, in the context of in vivo administration to a subject, "targeting" or "homing" can refer to the preferential movement, binding, and/or accumulation of a compound or composition, such as the disclosed compositions, in or at, for example, target tissue, target cells, and/or target structures as compared to non-target tissue, cells and/or structures.

The term "target tissue" as used herein refers to an intended site for accumulation of a targeted compound or composition, such as the disclosed compositions, following administration to a subject. For example, the methods of the presently disclosed subject matter employ a target tissue comprising endometriosis.

By "treatment" or "treating" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. The term "suffering" from a disease or condition as used herein refers to a judgment made by a caregiver (e.g. physician, nurse, nurse practitioner, or individual in the case of humans; veterinarian in the case of animals, including non-human mammals) that a subject has or is suspected of having the disease or condition. These judgments can be made based on a variety of factors that are in the realm of a care giver's expertise, but that include the knowledge that the subject is ill, or will be ill, as the result of a condition.

As used herein, "subject" includes, but is not limited to, animals, such as mammals and, preferably, humans. The term does not denote a particular age. In particular embodiments, adult females are intended to be covered. A patient refers to a subject afflicted with a disease or disorder. The term "patient" can include human and veterinary subjects. In the context of endometriosis and endometriosis cells, it is understood that a subject is a subject that has or can have endometriosis and/or endometriosis cells.

As used herein, reference to components (such as a first peptide comprising an endosome escape signal and a target peptide and a second peptide comprising an effector molecule and a target peptide) as being "not covalently coupled" means that the components are not connected via covalent bonds (for example, that the first peptide and the second peptide are not connected via covalent bonds). That is, there is no continuous chain of covalent bonds between, for example, the first peptide and the second peptide. Conversely, reference to components (such as an endosome escape signal and a target peptide) as being "covalently coupled" means that the components are connected via covalent bonds (for example, that the endosome escape signal and the target peptide are connected via covalent bonds). That is, there is a continuous chain of covalent bonds between, for example, the endosome escape signal and the target peptide. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a first peptide comprising an endosome escape signal and a target peptide and a second peptide comprising an effector molecule and a target peptide) as not being "non-covalently associated" means that there is no direct or indirect non-covalent association between the components. That is, for example, no atom covalently coupled to a first peptide is involved in a non-covalent bond with an atom covalently coupled to a second peptide. Within this meaning, a first peptide and a second peptide can be together in a composition where they are indirectly associated via multiple intervening non-covalent bonds while not being non-covalently associated as that term is defined herein. For example, a first peptide and a second peptide can be mixed together in a carrier where they are not directly non-covalently associated. A first peptide and a second peptide that are referred to as not indirectly non-covalently associated cannot be mixed together in a continuous composition. Reference to components (such as a first peptide comprising an endosome escape signal and a target peptide and a second peptide comprising an effector molecule and a target peptide) as not being "directly non-covalently associated" means that there is no direct non-covalent association between the components (an indirect non-covalent association may be present). Reference to components (such as a first peptide comprising an endosome escape signal and a target peptide and a second peptide comprising an effector molecule and a target peptide) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

B. Targeting Peptides

Disclosed are compositions comprising a targeting peptide that selectively binds a cell. In some aspects, the cell is an endometriosis cell. As used herein, an "endometriosis cell" refers to an endometrial cell that is ectopically located. Endometriosis is believed to be largely the result of transplantation of viable cells exfoliated from the endometrium to ectopic locations. This reflux menstruation theory is based on the hypothesis that viable endometrial cells are introduced to the peritoneal cavity through retrograde menstruation through the oviducts.

When a cell is targeted, the cell can be targeted specifically or non-specifically. That is, the cell can be a target of the composition or substantially the only target. For example, when an endometriosis cell is targeted, the endometriosis cell can be targeted specifically (for example, with no substantial targeting of endometrial cells that are not endometriosis cells) or non-specifically (with targeting of endometrial and endometriosis cells). Thus, in some aspects, the cell is not an endometrial cell.

As used herein, a "targeting peptide" is peptide or polypeptide that binds to a target, such as a cell. For example, a targeting peptide can display selective targeting activity. The terms "selective targeting" or "selective homing" as used herein each refer to a preferential localization of a compound or composition, such as the disclosed compositions, that results in an amount of the compound or composition in a target tissue that is, for example, about 2-fold greater than an amount of the peptide in a control tissue, about 5-fold or greater, or about 10-fold or greater. For example, the terms "selective targeting" and "selective homing" can refer to binding or accumulation of a compound or composition, such as the disclosed compositions in a target tissue concomitant with an absence of targeting to a control tissue or the absence of targeting to all control tissues.

Generally, a targeting peptide, or segment thereof, must comprise at least 5, 6, 7, 8, 9 contiguous amino acids that confer specificity and affinity. The targeting peptide can comprise, for example, the amino acid sequence set forth in SEQ ID NOs:1, 2, 3 or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4.

The targeting peptide can comprise, for example, an amino acid segment, wherein the segment has the amino acid sequence set forth in SEQ ID NOs:1, 2, 3, or 4. The targeting peptide can comprise an amino acid segment, wherein the segment has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The amino acid segment can have at least 5, 6, 7, 8, or 9 consecutive amino acids. Thus, the amino acid segment can consist essentially of 5, 6, 7, 8, or 9 consecutive amino acids. Thus, the targeting peptide can consist essentially of at least 5, 6, 7, 8, or 9 consecutive amino acids.

The disclosed targeting peptides can be artificial sequences and can be synthesized in vitro and/or recombinantly. The disclosed targeting peptides can be peptides that are not naturally occurring protein and can be peptides that have at least two contiguous sequences that are not contiguous in a naturally occurring protein. The disclosed targeting peptides can be 5 to about 50 amino acids in length. The disclosed targeting peptides can be less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids in length.

For clarity, different targeting peptides can be referred as, for example a first targeting peptide and a second targeting peptide. It is understood that all such targeting peptides are targeting peptides as described herein. The appended designation is used merely for convenience in distinguishing different instances of targeting peptides.

C. Endosome Escape Signals

Endosome escape signals are compounds and compositions, including, for example, polymers and sequences, that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. Endosomal release is important for the delivery of a wide variety of molecules which are endocytosed but incapable of diffusion across cellular membranes. Endosome escape signals undergo a shift in their physico-chemical properties over a physiologically relevant pH range (usually pH 5.5-8). This shift can be a change in the compound's solubility, ability to interact with other compounds, and a shift in hydrophobicity or hydrophilicity. Exemplary endosome escape signals can have pH-titratable groups or pH-labile groups or bonds. As used herein, pH-titratable groups reversibly accept or donate protons in water as a function of pH under physiological conditions, i.e. a pH range of 4-8. pH-titratable groups have $pK_a$'s in the range of 4-8 and act as buffers within this pH range. Thus, pH-titratable groups gain or lose charge in the lower pH environment of an endosome. In some embodiments, the pH-titratable groups gain charge in the lower pH environment of an endosome. Groups titratable at physiological pH can be determined experimentally by conducting an acid-base titration and experimentally determining if the group buffers within the pH-range of 4-8. Examples of groups that can exhibit buffering within this pH range include but are not limited to: carboxylic acids, imidazole, N-substituted imidazole, pyridine, phenols, and polyamines. An example of an amino acid useful in endosome escape signals is histidine. Compounds with pH-titratable groups may disrupt internal vesicles by the so-called proton sponge effect. A reversibly masked membrane active compound, wherein the masking agents are attached to the compound via pH labile bonds, can therefore be considered to be an endosome escape signal.

In some forms, the endosome escape signal can comprise an endosome escape peptide. An endosome escape peptide is a peptide that, in response to a change in pH, is able to cause disruption or lysis of an endosome or provide for escape of a normally membrane-impermeable compound, such as a polynucleotide or protein, from a cellular internal membrane-enclosed vesicle, such as an endosome or lysosome. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAH-HLAH (SEQ ID NO:38). In some forms, the endosome escape peptide can comprise two or more units of the sequence $HX_1X_2HX_3X_4H$, where $X_1$, $X_2$, $X_3$, and $X_4$ are each independently leucine, alanine, valine, or isoleucine. In some forms, the endosome escape peptide can comprise two or more units of the sequence $HX_1X_2HX_3X_4H$ followed by one unit of the sequence $HX_5X_6H$, where $X_1$, $X_2$, $X_3$, $X_4$, $X_5$, and $X_6$ are each independently leucine, alanine, valine, or isoleucine. In some forms, $X_1$, $X_2$, $X_3$, $X_4$, $X_5$, and $X_6$ are each independently leucine, alanine, valine, or isoleucine, where one of $X_1$, and $X_2$, is alanine or valine and the other is leucine or isoleucine, one of $X_3$, and $X_4$ is alanine or valine and the other is leucine or isoleucine, and one of $X_5$, and $X_6$ is alanine or valine and the other is leucine or isoleucine. In some forms, $X_1$, $X_2$, $X_3$, $X_4$, $X_5$, and $X_6$ are each independently leucine, alanine, valine, or isoleucine, where one of $X_1$, and $X_2$, is alanine and the other is leucine, one of $X_3$, and $X_4$ is alanine and the other is leucine, and one of $X_5$, and $X_6$ is alanine and the other is leucine.

A subset of endosome escape compounds is fusogenic compounds, including fusogenic peptides. Fusogenic peptides can facilitate endosomal release of agents such as oligomeric compounds to the cytoplasm. It is believed that fusogenic peptides change conformation in acidic pH, effectively destabilizing the endosomal membrane thereby enhancing cytoplasmic delivery of endosomal contents. Example fusogenic peptides include peptides derived from polymyxin B, influenza HA2, GALA, KALA, EALA, melittin and melittin-derived peptides, Alzheimer β3-amyloid peptide, and the like.

Surface charge reversal of compounds and compositions (from anionic to cationic) selectively in the acidic pH of endosomes and lysosomes is a mechanism for rapid endosomal and lysosomal escape of compounds and compositions. One of the strategies developed to facilitate endosomal escape mimics the fusion of viral envelopes with host cell endosomal membranes, which occurs during viral infections. Several synthetic fusogenic peptides have been synthesized based on the fusion domain of the influenza virus. Oliveira et al. (Fusogenic peptides enhance endosomal escape improving siRNA-induced silencing of oncogenes, International J. Pharmaceuticals 331(2):211-214 (2007)) evaluated the effects of the influenza-derived fusogenic peptide diINF-7 on gene silencing efficiency of siRNA targeting the epidermal growth factor receptor (EGFR) and the K-ras oncogenes. For both targets, strong enhancement of gene silencing activity was noted after addition of diINF-7 fusogenic peptide, identifying endosomal escape as a limiting factor for siRNA silencing efficiency.

D. Effectors

The disclosed compositions and antibodies can further comprise an effector molecule. By "effector molecule" is meant a substance that acts upon the target cell(s) or tissue to bring about a desired effect. The effect can, for example, be the labeling, activating, repressing, or killing of the target cell(s) or tissue. Thus, the effector molecule can, for example, be a peptide, apoptosis-inducing compound, apoptosis-inducing peptide, small molecule, pharmaceutical drug, toxin, fatty acid, detectable marker, conjugating tag, nanoparticle, or enzyme. Thus, the disclosed effector molecules are not limited to "molecules" as that term is used chemistry. Rather, an effector molecule can be, for example, a molecule, compound, composition, conjugate, or a plurality of such, or a combination of such.

The moiety can be, for example, a therapeutic moiety or a detectable moiety, a cytotoxic agent, an anti-lymphangiogenic agent, a cancer chemotherapeutic agent, a pro-apoptotic polypeptide (apoptosis-inducing peptide), a grafted polypeptide, a virus, a cell, or a liposome. Thus, the moiety can be a small molecule, pharmaceutical drug, toxin, fatty acid, detectable marker, conjugating tag, nanoparticle, or enzyme. For example, the moiety of the disclosed conjugate can be a pro-apoptotic peptide. A pro-apoptotic peptide (also referred to herein as an apoptosis-inducing peptide) is a peptide that can cause, induce, stimulate, or increase apoptosis in a cell or group of cells. Examples of pro-apoptotic peptides are the amino acid sequence such as $(KLAKLAK)_2$ or $_D(KLAKLAK)_2$ (SEQ ID NO:26), tumor necrosis factor (Curnis et al., Cancer Res. 64, 565-71, 2004) and tachyplesin (Chen et al., Cancer res. 61, 2434-8, 2001). Preferred apoptosis-inducing peptides comprise two or more KLAK-LAK sequences (SEQ ID NO:39). Also preferred are apoptosis-inducing peptides comprising the sequence KLAK-LAKKLAKLAKKLAK (SEQ ID NO:40). Many other pro-apoptotic peptides and compounds are known and can be used with and in the disclosed compositions, conjugates and methods.

The mitochondriotoxic pro-apoptotic peptide (PAP) of sequence $(KLAKLAK)_2$ (SEQ ID NO:26) is a synthetic peptide originally developed to enhance the activity of a natural antimicrobial peptide (Javadpour et al., J Med Chem 1996; 39: 3107-13). This class of polypeptides that preferentially permeabilizes bacterial membranes rich in anionic phospholipids has also been shown to affect mitochondrial function in vitro (Ellerby et al., J Neurosci 1997; 17: 6165-78; del Rio et al., FEBS Lett 2001; 494: 213-9). $(KLAKLAK)_2$ (SEQ ID NO:26) cannot efficiently permeate across eukaryotic plasma membranes and consequently, by itself, exhibits low mammalian cell cytotoxicity. However, when coupled to selective targeting domains, $(KLAKLAK)_2$ (SEQ ID NO:26) is internalized by cells, induces mitochondrial damage, and triggers apoptosis (Ellerby et al., Nat Med 1999; 5: 1032-8). This approach has been successfully employed to target angiogenic endothelial cells and the vasculature of white fat (Ellerby et al., Nat Med 1999; 5: 1032-8; Kolonin et al., Nat Med 2004; 10: 625-32). It has been proposed that the cationic and amphipatic nature of PAPs drives the alignment of the positively charged peptide surface with the negatively charged mitochondrial membrane, affecting its electro-elastic properties and compromising the organelle's biological function (Matsuzaki, Biochim Biophys Acta 1998; 1376: 391-400).

$(KLAKLAK)_2$ (SEQ ID NO:26) belongs to a class of compounds that induces apoptosis via a direct effect on mitochondria. A key event following mitochondria permeabilization during the course of the apoptotic response is the release to the cytosol of proapoptotic proteins, such as cytochrome c, normally stored in the intermembrane space (Green and Kroemer, Trends Cell Biol 1998; 8: 267-71; Scorrano and Korsmeyer, Biochem Biophys Res Commun 2003; 304:437-44). This event is in turn followed by the activation of cysteine aspartyl proteases (caspases) as well as endonucleases that execute the cleavage of specific protein substrates and of genomic DNA. $(KLAKLAK)_2$ (SEQ ID NO:26) has been previously shown to induce release of cytochrome c from mitochondria and loss of mitochondrial potential in vitro (Ellerby et al., Nat Med 1999; 5: 1032-8).

Examples of small molecules and pharmaceutical drugs that can be conjugated to a targeting peptide are known in the art. The effector can be a cytotoxic small molecule or drug that kills the target cell. The small molecule or drug can be designed to act on any critical cellular function or pathway. For example, the small molecule or drug can inhibit the cell cycle, activate protein degradation, induce apoptosis, modulate kinase activity, or modify cytoskeletal proteins. Any known or newly discovered cytotoxic small molecule or drugs is contemplated for use with the targeting peptides.

The effector can be a toxin that kills the targeted cell. Non-limiting examples of toxins include abrin, modeccin, ricin, and diphtheria toxin. Other known or newly discovered toxins are contemplated for use with the targeting peptides.

Fatty acids (i.e., lipids) that can be conjugated to the targeting peptide include those that allow the efficient incorporation of the peptide into liposomes. Generally, the fatty acid is a polar lipid. Thus, the fatty acid can be a phospholipid. The disclosed compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the disclosed compositions can comprise palmitoyl 16:0.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the targeting peptides.

The effector molecule can be a nanoparticle, such as a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, especially for use in cancer therapy, such as the use of heated probes, microwaves, ultrasound, lasers, perfusion, radiofrequency energy, and radiant heating is avoided since the levels of radiation used as described herein is insufficient to induce hyperthermia except at the surface of the nanoparticles, where the energy is more effectively concentrated by the metal surface on the dielectric. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The effector molecule can be covalently linked to the targeting peptide. The effector molecule can be linked to the amino terminal end of the targeting peptide. The effector molecule can be linked to the carboxy terminal end of the targeting peptide. The effector molecule can be linked to an amino acid within the targeting peptide. The disclosed compositions can further comprise a linker connecting the effector molecule and targeting peptide. The targeting peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the targeting peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy)sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy)sulfosuccinimide ester), SMPH (Succinimidyl-6-(beta-maleimidopropionamidohexanoate)),
SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

The disclosed compositions can further comprise a progestational agent. Thus, the compositions can comprise Danazol, medroxyprogesterone acetate, norethynodrel, megestrol acetate, dydrogesterone, norethisterone, or lynestrenol. The disclosed compositions can further comprise a Gonadotropin-releasing hormone (GnRH), GnRH analog, or GnRH agonist. Thus, the compositions can comprise leuprorelin, nafarelin, goserelin, buserelin, or triptorelin. The compositions can further comprise an aromatase inhibitor. Thus, the compositions can comprise letrozole or anasrozole. The compositions can further comprise a narcotic. The compositions can further comprise a non-steroidal anti-inflammatory drug (NSAID). Thus the compositions can comprise ibuprofen, naproxen, nurofen, ponstan, or voltaren.

1. Pharmaceutical Carriers

The disclosed targeting peptides and antibodies can be administered in vivo in a pharmaceutically acceptable carrier. Thus, the disclosed compositions and antibodies can further comprise a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The disclosed compositions and antibodies can be in solution, suspension (for example, incorporated into microparticles, liposomes, or cells). The disclosed compositions and antibodies can further be combined with antibodies, receptors, or receptor ligands to direct internalization of the composition into the targeted endometriosis cell. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Nucleic Acids

Disclosed are isolated nucleic acids comprising a nucleic acid sequence encoding a targeting peptide that selectively binds an endometriosis cell. The nucleic acid sequence can encode the amino acid sequence set forth in SEQ ID NOs:1, 2, 3, or 4.

The nucleic acid can further comprise a nucleic acid sequence encoding an effector molecule. For example, the effector molecule can be any polypeptide effector disclosed herein. The nucleic acid sequence encoding the effector molecule can be 5' to the nucleic acid sequence encoding the targeting peptide. The nucleic acid sequence encoding the effector molecule can be 3' to the nucleic acid sequence encoding the targeting peptide. The nucleic acid can encode a fusion protein comprising the targeting peptide and the effector molecule.

Also disclosed are isolated nucleic acids comprising a nucleic acid sequence encoding an antibody specific for the cyclic nucleotide-gated channel beta 3 (CNGB3), specific for an epitope comprising the amino acid sequence SEQ ID NO:32, or both.

3. Antibodies

Disclosed are antibodies, wherein the antibody is specific for the cyclic nucleotide-gated channel beta 3 (CNGB3). Also disclosed are antibodies, wherein the antibody is specific for an epitope comprising the amino acid sequence SEQ ID NO:32. Such antibodies can be used to target, detect, inhibit, or kill cells expressing CNGB3, and target, detect, inhibit, or kill endometriosis cells. Also disclosed are antibodies specific for the disclosed targeting peptides.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the targeting peptide such that the targeting peptide is inhibited from interacting with the target cell. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagen-

E. Compositions

Disclosed are compositions comprising an endosome escape signal and a targeting peptide that selectively binds an endometriosis cell. The endosome escape signal can comprise an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAHHLAH (SEQ ID NO:38).

Also disclosed are compositions comprising an effector molecule and a targeting peptide that selectively binds an endometriosis cell. The effector molecule can comprise a peptide, apoptosis-inducing compound, small molecule, pharmaceutical drug, toxin, fatty acid, detectable marker, conjugating tag, nanoparticle, or enzyme. For example, the effector can comprise an apoptosis-inducing compound. For example, the apoptosis-inducing compound can be a $(KLAKLAK)_2$ (SEQ ID NO:26) peptide or a peptide of the sequence KLAKLAKKLAKLAKKLAK (SEQ ID NO:40). The composition can also comprise an endosome escape signal. For example, the composition can comprise a polyhistidine peptide.

Also disclosed are compositions comprising an endosome escape signal, an effector molecule, and a targeting peptide that selectively binds an endometriosis cell. In some forms, the endosome escape molecule can comprise an endosome escape peptide and the effector molecule can comprise an apoptosis-inducing peptide. Also disclosed are nucleic acids comprising a nucleic acid sequence encoding an endosome escape signal, an effector molecule, and a targeting peptide that selectively binds an endometriosis cell. Also disclosed are nucleic acids comprising a nucleic acid sequence encoding an endosome escape peptide, an apoptosis-inducing peptide, and a targeting peptide that selectively binds an endometriosis cell.

In some forms, the compositions comprise two peptides. In some forms, the first peptide can comprise an endosome escape signal and a targeting peptide that selectively binds an endometriosis cell. In some forms, the second peptide can comprise an effector molecule and a second targeting peptide that selectively binds an endometriosis cell. In some forms, the endosome escape molecule can comprise an apoptosis-inducing peptide. Also disclosed are compositions comprising an endosome escape signal, an effector molecule, and a targeting peptide that selectively binds an endometriosis cell. Also disclosed are nucleic acids comprising a nucleic acid sequence encoding an endosome escape signal, an effector molecule, and a targeting peptide that selectively binds an endometriosis cell.

The disclosed compositions can comprise any of the components described herein. For example, the composition can comprise a targeting peptide, an effector molecule, an endosome escape signal, an internalization sequence, a pharmaceutical carrier, multiple types of any such components, and/or any combination of such components.

F. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

G. Protein Variants

The targeting peptide can comprise the amino acid sequence set forth in SEQ ID NOs:1, 2, 3, or 4, with one or more conservative amino acid substitutions. Thus, the targeting peptide can comprise the amino acid sequence set forth in SEQ ID NOs:1, 2, 3, or 4, with one, two or three conservative amino acid substitutions. As an example, the targeting peptide can comprise the amino acid sequence set forth in SEQ ID NOs:1, 2, 3, or 4, with one conservative amino acid substitution. The targeting peptide can also comprise an amino acid segment having the amino acid sequence set forth in SEQ ID NOs:1, 2, 3, or 4, with one or more conservative amino acid substitutions. Thus, the targeting peptide can comprises an amino acid segment having the amino acid sequence set forth in SEQ ID NOs:1, 2, 3, or 4, with one, two or three conservative amino acid substitutions. As an example, the targeting peptide can comprises an amino acid segment having the amino acid sequence set forth in SEQ ID NOs:1, 2, 3, or 4, with one conservative amino acid substitution. The targeting peptide can comprise at least 6 contiguous amino acids from the amino acid sequence set forth in SEQ ID NOs:1, 2, 3, or 4. The targeting peptide can have at least 5, 6, 7, 8, or 9 consecutive amino acids. Thus, targeting peptide can consist of 5, 6, 7, 8, or 9 consecutive amino acids.

As discussed herein targeting peptides can include numerous variants based on a starting targeting peptide. Protein and peptide variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 2

Amino Acid Substitutions

| Original Residue | Exemplary Conservative Substitutions (others are known in the art) |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that the description of conservative mutations and homology can be combined together in any combination, such as embodiments that have at least 70% homology to a particular sequence wherein the variants are conservative mutations.

As this specification discusses various peptide sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —$CH$=$CH$— (cis and trans), —$COCH_2$—, —$CH(OH)$ $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—$S$); Hann J. Chem. Soc Perkin Trans. I 307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)$ $CH_2$—); Holladay et al. Tetrahedron. Lett 24:4401-4404 (1983) (—$C(OH)CH_2$—); and Hruby Life Sci 31:189-199 (1982) (—$CH_2$—$S$—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (Rizo and Gierasch Ann. Rev. Biochem. 61:387 (1992), incorporated herein by reference).

H. Internalization Sequence

The disclosed compositions can further comprise a cellular internalization transporter or sequence. The Internalization sequence can be, for example, coupled to the targeting peptide or can be included in compositions containing the targeting peptide. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 1).

Thus, the disclosed targeting peptide can further comprise the amino acid sequence SEQ ID NO:10, SEQ ID NO:11 (Bucci, M. et al. 2000. Nat. Med. 6, 1362-1367), SEQ ID NO:12 (Derossi, D., et al. 1994. Biol. Chem. 269, 10444-10450), SEQ ID NO:13 (Fischer, P. M. et al. 2000. J. Pept. Res. 55, 163-172), SEQ ID NO:14 (Frankel, A. D. & Pabo, C. O. 1988. Cell 55, 1189-1193; Green, M. & Loewenstein, P. M. 1988. Cell 55, 1179-1188), SEQ ID NO:15 (Park, C.

B., et al. 2000. Proc. Natl Acad. Sci. USA 97, 8245-8250), SEQ ID NO:16 (Pooga, M., et al. 1998. FASEB J. 12, 67-77), SEQ ID NO:17 (Oehlke, J. et al. 1998. Biochim. Biophys. Acta. 1414, 127-139), SEQ ID NO:18 (Lin, Y. Z., et al. 1995. J. Biol. Chem. 270, 14255-14258), SEQ ID NO:19 (Sawada, M., et al. 2003. Nature Cell Biol. 5, 352-357), SEQ ID NO:20 (Lundberg, P. et al. 2002. Biochem. Biophys. Res. Commun 299, 85-90), SEQ ID NO:21 (Elmquist, A., et al. 2001. Exp. Cell Res. 269, 237-244), SEQ ID NO:22 (Morris, M. C., et al. 2001. Nature Biotechnol. 19, 1173-1176), SEQ ID NO:23 (Rousselle, C. et al. 2000. Mol. Pharmacol. 57, 679-686), SEQ ID NO:24 (Gao, C. et al. 2002. Bioorg. Med. Chem. 10, 4057-4065), or SEQ ID NO:25 (Hong, F. D. & Clayman, G. L. 2000. Cancer Res. 60, 6551-6556). The disclosed polypeptide can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety and for their teachings of cellular internalization vectors and sequences. Any other internalization sequences now known or later identified can be combined with a polypeptide disclosed herein.

TABLE 1

Cell Internalization Transporters

| Name | Sequence | SEQ ID NO |
|---|---|---|
| Antp | RQPKIWFPNRRKPWKK | (SEQ ID NO: 10) |
| HIV-Tat | GRKKRRQRPPQ | (SEQ ID NO: 11) |
| Penetratin | RQIKIWFQNRRMKWKK | (SEQ ID NO: 12) |
| Antp-3A | RQIAIWFQNRRMKWAA | (SEQ ID NO: 13) |
| Tat | RKKRRQRRR | (SEQ ID NO: 14) |
| Buforin II | TRSSRAGLQFPVGRVHRLLRK | (SEQ ID NO: 15) |
| Transportan | GWTLNSAGYLLGKINKALAALAKKIL | (SEQ ID NO: 16) |
| model amphipathic peptide (MAP) | KLALKLALKALKAALKLA | (SEQ ID NO: 17) |
| K-FGF | AAVALLPAVLLALLAP | (SEQ ID NO: 18) |
| Ku70 | VPMLK-PMLKE | (SEQ ID NO: 19) |
| Prion | MANLGYWLLALFVTMWTDVGLCKKRPKP | (SEQ ID NO: 20) |
| pVEC | LLIILRRRIRKQAHAHSK | (SEQ ID NO: 21) |
| Pep-1 | KETWWETWWTEWSQPKKKRKV | (SEQ ID NO: 22) |
| SynB1 | RGGRLSYSRRRFSTSTGR | (SEQ ID NO: 23) |
| Pep-7 | SDLWEMMMVSLACQY | (SEQ ID NO: 24) |
| HN-1 | TSPLNIHNGQKL | (SEQ ID NO: 25) |
| BGSC (Bis-Guanidinium-Spermidine-Cholesterol) | BGSC structure | |
| BGTC (Bis-Guanidinium-Tren-Cholesterol) | BGTC structure | |

I. Methods

1. Cell Targeting and Detection

Disclosed are methods comprising administering to a subject a composition comprising a targeting peptide that selectively binds a cell. In some forms, the cell is an endometriosis cell. In other forms, the cell is not an endometrial cell. The subject can comprise the cell. Thus, the subject can comprise an endometriosis cell. Also disclosed are methods comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both.

Also disclosed are methods of treating a subject suffering endometriosis, the method comprising administering to the subject a composition comprising an endosome escape signal and a targeting peptide that selectively binds an endometriosis cell, thereby treating the subject. In some forms, the endosome escape signal can comprise an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAH-HLAH (SEQ ID NO:38).

Also disclosed are methods of treating a subject suffering endometriosis, the method comprising administering to the subject a composition comprising an effector molecule and a targeting peptide that selectively binds an endometriosis cell, thereby treating the subject. For example, the effector can comprise an apoptosis-inducing compound. For example, the apoptosis-inducing compound can be a (KLAKLAK)$_2$ peptide.

The targeting peptide of the disclosed methods can be any of the herein disclosed targeting peptides. Thus, the targeting peptide can comprise the amino acid sequence set forth in SEQ ID NOs:1, 2, 3, or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The targeting peptide can comprise the amino acid sequence set forth in SEQ ID NOs:1, 2, 3, or 4 with one or more conservative amino acid substitutions. The composition or antibody of the disclosed methods can further comprise an effector molecule. Thus, the effector molecule is a small molecule, pharmaceutical drug, toxin, fatty acid, detectable marker, nanoparticle or enzyme.

Also disclosed are methods of treating a subject suffering endometriosis, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, thereby treating the subject.

Also disclosed are methods of targeting an endometriosis cell in a subject, the method comprising administering to the subject a composition comprising a targeting peptide that selectively binds an endometriosis cell. The cell can be an endometriosis cell. The targeting peptide can comprises the amino acid sequence set forth in SEQ ID NOs:1, 2, 3, or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The targeting peptide can comprise the amino acid sequence set forth in SEQ ID NOs:1, 2, 3, or 4 with one or more conservative amino acid substitutions.

Also disclosed are methods of targeting an endometriosis cell in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both.

The composition or antibody of the disclosed methods can further comprise an endosome escape signal. In some forms, the endosome escape signal can comprise an endosome escape peptide. In some forms, the endosome escape peptide can comprise multiple histidine residues. In some forms, the endosome escape peptide can form an alpha helix under acidic conditions. In some forms, the endosome escape peptide can comprise two or more HLAHLAH sequences (SEQ ID NO:37). In some forms, the endosome escape peptide can comprise the sequence HLAHLAHHLAHLAH-HLAH (SEQ ID NO:38).

The composition or antibody of the disclosed methods can further comprise an effector molecule. Thus, the effector molecule can be a small molecule, pharmaceutical drug, toxin, fatty acid, detectable marker, nanoparticle or enzyme. The composition of the methods can comprise a progestational agent. Thus, the composition or antibody can comprise Danazol, medroxyprogesterone acetate, norethynodrel, megestrol acetate, dydrogesterone, norethisterone, or lynestrenol. The composition or antibody can further comprise a Gonadotropin-releasing hormone (GnRH), GnRH analog, or GnRH agonist. Thus, the composition or antibody can comprise leuprorelin, nafarelin, goserelin, buserelin, or triptorelin. The composition or antibody can further comprise an aromatase inhibitor. Thus, the composition or antibody can comprise letrozole or anasrozole. The composition or antibody can further comprise a narcotic. The composition or antibody can further comprise a non-steroidal anti-inflammatory drug (NSAID). Thus the composition or antibody can comprise ibuprofen, naproxen, nurofen, ponstan, or voltaren.

Also disclosed are methods of detecting endometriosis in a subject, the method comprising administering to the subject a composition comprising a targeting peptide that selectively binds an endometriosis cell and detecting the composition in the subject, thereby detecting endometriosis. Also disclosed are methods of detecting endometriosis in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, and detecting the antibody in the subject, thereby detecting endometriosis. For example, the composition or antibody can comprise a label or other detectable moiety or molecule (as the effector, for example) and the composition or antibody can be detected by, for example, detecting the label or other detectable moiety or molecule. The presence, location, pattern or other characteristics of the detected composition or antibody can be used as an indicator that the subject has endometriosis.

Also disclosed are methods of diagnosing endometriosis in a subject, the method comprising administering to the subject a composition comprising a targeting peptide that selectively binds an endometriosis cell and detecting the composition in the subject, thereby diagnosing endometriosis in the subject. Also disclosed are methods of diagnosing endometriosis in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, and detecting the antibody in the subject, thereby diagnosing endometriosis in the subject. For example, the composition or antibody can comprise a label or other detectable moiety or molecule (as the effector, for example) and the composition or antibody can be detected by, for example, detecting the label or other detectable moiety or molecule. The presence, location, pattern or other characteristics of the detected composition or antibody can be used as an indicator that the subject has endometriosis.

Also disclosed are methods of determining the prognosis of endometriosis in a subject, the method comprising administering to the subject a composition comprising a targeting peptide that selectively binds an endometriosis cell and detecting the composition in the subject, wherein the level, amount, concentration, or a combination of binding of the composition to endometriosis tissue in the subject indicates the prognosis of the endometriosis in the subject. Also disclosed are methods of determining the prognosis of endometriosis in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, and detecting the antibody in the subject, wherein the level, amount, concentration, or a combination of binding of the antibody to endometriosis tissue in the subject indicates the prognosis of the endometriosis in the subject. For example, the composition or antibody can comprise a label or other detectable moiety or molecule (as the effector, for example) and the composition or antibody can be detected by, for example, detecting the label or other detectable moiety or molecule. The presence, location, pattern or other characteristics of the detected composition or antibody can be used as an indicator of the severity and/or future progress of the endometriosis.

Also disclosed are methods of determining the progress of endometriosis in a subject, the method comprising administering to the subject a composition comprising a targeting peptide that selectively binds an endometriosis cell, detecting the composition in the subject, and repeating the administration and detection at a later time, wherein a change in the level, amount, concentration, or a combination of binding of the composition to endometriosis tissue in the subject indicates the progress of the endometriosis in the subject. Also disclosed are methods of determining the progress of endometriosis in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, detecting the antibody in the subject, and repeating the administration and detection at a later time, wherein a change in the level, amount, concentration, or a combination of binding of the antibody to endometriosis tissue in the subject indicates the progress of the endometriosis in the subject. For example, the composition or antibody can comprise a label or other detectable moiety or molecule (as the effector, for example) and the composition or antibody can be detected by, for example, detecting the label or other detectable moiety or molecule. A change in the presence, location, pattern or other characteristics of the detected composition or antibody can be used as an indicator of the progress of the endometriosis.

Also disclosed are methods of determining the progress treatment of endometriosis in a subject, the method comprising administering to the subject a composition comprising a targeting peptide that selectively binds an endometriosis cell, detecting the composition in the subject, and repeating the administration and detection following treatment, wherein a change in the level, amount, concentration, or a combination of binding of the composition to endometriosis tissue in the subject indicates the progress the treatment of the endometriosis in the subject. Also disclosed are methods of determining the progress treatment of endometriosis in a subject, the method comprising administering to a subject an antibody, wherein the antibody is specific for the cyclic nucleotide-gated channel beta 3 (CNGB3), wherein the antibody is specific for an epitope comprising the amino acid sequence SEQ ID NO:32, or both, detecting the antibody in the subject, and repeating the administration and detection following treatment, wherein a change in the level, amount, concentration, or a combination of binding of the antibody to endometriosis tissue in the subject indicates the progress the treatment of the endometriosis in the subject. For example, the composition or antibody can comprise a label or other detectable moiety or molecule (as the effector, for example) and the composition or antibody can be detected by, for example, detecting the label or other detectable moiety or molecule. A change in the presence, location, pattern or other characteristics of the detected composition or antibody can be used as an indicator of the progress treatment of the endometriosis.

Also disclosed are methods of treating a subject in need thereof with a composition targeted to a cell or tissue of interest, where the composition comprises an endosome escape signal and a targeting peptide that selectively binds the cell or tissue of interest, where the endosome escape signal comprises an endosome escape peptide, and where the endosome escape peptide comprises two or more HLAHLAH sequences (SEQ ID NO:37). In some forms, the endosome escape peptide can comprise the sequence HLAHLAHHLAHLAHHLAH (SEQ ID NO:38). In some forms, the endosome escape peptide can comprise two or more units of the sequence $HX_1X_2HX_3X_4H$, where $X_1$, $X_2$, $X_3$, and $X_4$ are each independently leucine, alanine, valine, or isoleucine. In some forms, the endosome escape peptide can comprise two or more units of the sequence $HX_1X_2HX_3X_4H$ followed by one unit of the sequence $HX_5X_6H$, where $X_1$, $X_2$, $X_3$, $X_4$, $X_5$, and $X_6$ are each independently leucine, alanine, valine, or isoleucine. In some forms, $X_1$, $X_2$, $X_3$, $X_4$, $X_5$, and $X_6$ are each independently leucine, alanine, valine, or isoleucine, where one of $X_1$, and $X_2$, is alanine or valine and the other is leucine or isoleucine, one of $X_3$, and $X_4$ is alanine or valine and the other is leucine or isoleucine, and one of $X_5$, and $X_6$ is alanine or valine and the other is leucine or isoleucine. In some forms, $X_1$, $X_2$, $X_3$, $X_4$, $X_5$, and $X_6$ are each independently leucine, alanine, valine, or isoleucine, where one of $X_1$, and $X_2$, is alanine and the other is leucine, one of $X_3$, and $X_4$ is alanine and the other is leucine, and one of $X_5$, and $X_6$ is alanine and the other is leucine.

The targeting peptide of the disclosed methods of detection and diagnosis can be linked to a detectable marker, such as those known in the art or disclosed herein. The antibody of the disclosed methods of detection and diagnosis can be linked to a detectable marker, such as those known in the art or disclosed herein. The detectable markers can be detected using standard methods known in the art.

The disclosed compositions and antibodies can also be used in a variety of ways as research tools. For example, the disclosed compositions, such as SEQ ID NOs:1, 2, 3, or 4, and antibodies can be used to study protein expression by endometriosis cells. This can be accomplished by, for example, isolating or sorting cells based on the binding of the disclosed compositions to the cell. The disclosed compositions and antibodies can also be used diagnostic tools related to endometriosis. The disclosed compositions and antibodies can also be used as either reagents in micro arrays or as reagents to probe or analyze existing microarrays.

2. Administration

The compositions can be administered via any suitable route. Generally, the compositions can be administered intraperitoneally. For example, the disclosed compositions can be administered into a subject's peritoneal cavity during laparoscopy. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, extent of the disease in the patient, hormonal conditions, route of administration, or whether other drugs are included in the regimen, and can be determined by one of skill in the art. The dosage can be adjusted by the individual physician in the event of any counterindications. Dosage can vary for one or several days. Guidance can be found in the literature for appropriate dosages for given classes of pharmaceutical products. In some forms, the composition can be administered during surgery, for example, during laparoscopy. Such administration can be performed once, can be repeated one or more times, or can be combined with different administration(s) at different time(s).

The compositions disclosed herein and the compositions necessary to perform the disclosed methods can be made using any method known to those of skill in the art for that particular reagent or compound unless otherwise specifically noted.

One method of producing the disclosed peptides, such as SEQ ID NOs:1, 2, 3, or 4, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Production of antibodies is well known and some useful methods are described elsewhere herein.

J. Methods of Making the Compositions

The compositions disclosed herein and the compositions necessary to perform the disclosed methods can be made using any method known to those of skill in the art for that particular reagent or compound unless otherwise specifically noted.

Disclosed are processes for making the compositions as well as making the intermediates leading to the compositions. For example, disclosed are nucleic acid molecules produced by the process comprising linking in an operative way a nucleic acid molecule comprising a sequence encoding a peptide set forth in SEQ ID NO:1, 2, 3, 4, 26-30, or 35-172 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:1, 2, 3, 4, 26-30, or 35-172 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO:1, 2, 3, 4, 26-30, or 35-172 wherein any change is a conservative change, and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally occurring disclosed nucleic acids.

Disclosed are animals produced by the process of transfecting a cell within the animal with any of the nucleic acid molecules disclosed herein. Disclosed are animals produced by the process of transfecting a cell within the animal with any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

Production of antibodies is well known and some useful methods are described elsewhere herein.

1. Nucleic Acid Synthesis

The disclosed nucleic acids, such as the oligonucleotides to be used as primers, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:1, 2, 3, 4, 26-30, or 35-172, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

K. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for diagnosing endometriosis. The kit can comprise a composition comprising a targeting peptide conjugated to a detectable marker and a means for detection. Detectable markers are known in the art and include, for example, enzymes, fluorescent molecules and proteins, and radioactive isotopes. Means for detection are also known in the art and depend on the selected marker.

L. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising a composition comprising a targeting peptide conjugated to a nanoshell and a means for excitation of the nanoshell. Such means are known in the art.

EXAMPLES

A. Example 1

Results

Identification of Phage Clones

Since the endometrial adenocarcinoma Ishikawa line exhibits characteristics of endometrial epithelia (Lessey, B. A., et al., 1996; Castelbaum, A. J., et al.; 1997; Gong, Y., et al., 1994), Ishikawa cells were used as a target in library screening.

Because the goal was to identify a peptide that could be used to target peritoneal endometriosis, a subtraction step was included by mouse peritoneum during library screening (Stausbol-Gron, B., et al., 1996; Rasmussen, U. B., et al., 2002). Thus, a phage library ($10^{11}$ pfu) for linear 9-mer peptides was injected into the peritoneal cavity of a female mouse. The phage was incubated with peritoneal tissues by gentle massage. Thirty minutes later, the mouse was sacrificed and phage library was recovered from the peritoneum for the next step. This subtraction step was included in each cycle of the library screening. A peptide displaying phage library was subtracted using female mouse peritoneum followed by adhesion to and internalization by Ishikawa cells. In order to identify a peptide that internalizes to the cytoplasm of endometrial glandular epithelial cells, so that a drug conjugated with the peptide could effectively kill endometrial cells, a phage library was screened by incubating it with Ishikawa cells at room temperature or at 37° C. to facilitate internalization of phage upon binding to the cell surface. After three rounds of library screening by this strategy, the number of phage that bound to Ishikawa cells relative to the total number of added phage increased 10,000-fold (FIG. 1).

This phage pool was overlayed on frozen human tissue sections including uterine endometriosis, and the binding of phage to sections was visualized by the immunoperoxidase method using an anti-T7 phage antibody. Phage overlays were on frozen sections of human uterine endometriosis and human liver. Phage pools obtained after three rounds of screening were overlayed on frozen sections. Binding was visualized by the immunoperoxidase method using rabbit anti-T7 phage antibody. Counterstaining was done with hematoxylin. Strong signals were detected at glandular epithelial cells particularly at apical cell surfaces in endometriosis, and relatively weak signals were seen in smooth muscle cells, blood vessels, or stromal cells in the same sections. There were no obvious signals for phage overlayed on sections from human lung, colon, heart, and liver. These results indicate that the phage pool contains a clone or clones specifically binding to endometrial glandular epithelial cells of endometriosis. Each phage clone in this pool was therefore sequenced to determine the peptide sequence displayed on the phage (Table I).

Binding Specificity of Cloned Phage

Several selected phage clones showed a consensus sequence (Table 3). Peptide sequences on z12, z13, and z15 clones were VRRAXNXPG (SEQ ID NO:1), where X represents a variable amino acid residue among these clones. When z12, z13, and z15 clones were individually overlayed on frozen endometrial sections, immunohistochemistry by anti-phage antibody showed a similar staining pattern to that seen with the phage pools. An in vitro binding assay of clones using Ishikawa cells and control A431 cells indicated that z12, z13, and z15 phage bind to Ishikawa cells at significantly higher efficiency than to A431 cells. The binding assay also showed that z13 is the strongest binder of the three to Ishikawa cells. In addition to Ishikawa cells, it was determined that z13 phage binds to endometrial adenocarcinoma, SNG-II, RL95-2, Hec1A, and HES cells, whereas it does not bind to A431, prostate cancer PC-3 and cervical cancer HeLa cells, indicating that its binding is specific to endometrial cells. These results led us to focus on z13 phage, which displays the peptide sequence VRRADNRPG (SEQ ID NO:3).

TABLE 3

Peptide sequences displayed by clone phage.

| clone name | peptide sequence | SEQ ID |
|---|---|---|
| z11 | VRSSRSTPQ | SEQ ID NO: 7 |
| z12 | VRRANNLPG | SEQ ID NO: 2 |
| z13 | VRRADNRPG | SEQ ID NO: 3 |
| z15 | VRRANNRPG | SEQ ID NO: 4 |
| z24 | MQRTRATPG | SEQ ID NO: 8 |

Consensus amino acid residues are shown by bold letters.

In Vitro Targeting Activity of Synthetic z13 Peptide

When Ishikawa cells were overlayed with z13 phage and reacted with anti-phage antibody, immunofluorescence microscopy showed positive signals, whereas A431 cells overlayed with z13 phage did not show positive signals. FITC-z13, a synthetic fluorescence-tagged z13 peptide whose amino-terminus was conjugated, bound to Ishikawa cells, whereas FITC-z13 did not show fluorescence on A431 cells. These results indicate that peptide sequence displayed on z13 phage has binding activity to Ishikawa cells.

Z13 peptide was next chemically synthesized and conjugated at its amino terminus with palmitoyl C16 fatty acid, so that the peptide would be incorporated efficiently into liposomes. A fluorescent reagent (Qdot streptavidin) was enclosed in peptide-coated liposomes, enabling them to be traced under a fluorescence microscope. When z13 peptide-coated liposomes were added onto live Ishikawa cells, strong fluorescence signals were detected on the cell surface. By contrast, fluorescent liposomes coated with control (RGMSDTTAL, SEQ ID NO: 9) peptide, C16-m2, did not show fluorescence signals. These results indicate that liposomes coated with C16-z13 specifically target Ishikawa cells.

Synthetic cys-z13 peptide, CVRRADNRPG (SEQ ID NO:6), was conjugated to Qdot. When Qdot-cys-z13 was added to Ishikawa cell cultures, strong fluorescence was detected on Ishikawa cells, whereas Qdot-cys-m2, a Qdot conjugate of the control peptide, did not show fluorescence signals on Ishikawa cells. These results indicate that z13 peptide efficiently binds to Ishikawa cells regardless of its modification at the amino terminus.

Materials and Methods

Phage Library and Antibodies

A T7 phage library displaying random 9-mer peptide sequences constructed in the T7 Select 415-1b vector (Novagen) (Essler, M. & Ruoslahti, E., 2002). Polyclonal rabbit anti-T7 phage antibodies do not cross-react with frozen and paraffin sections of normal human and mouse tissues (Essler, M. & Ruoslahti, E., 2002).

Synthetic Peptides

The following peptides were synthesized by AnaSpec, San Jose, Calif.: z13, VRRADNRPG (SEQ ID NO:3); cys-z13, CVRRADNRPG (SEQ ID NO:6); cys-m2, CRGMSDTTAL (SEQ ID NO:5); fluorescent FITC-z13, and fatty acid conjugated C16-z13. Each cys-z13 and cys-m2 was bound to fluorescent nanocrystal Qdot605 using a Qdot antibody conjugation kit (Quantum Dot, Hayward, Calif.), according to the manufacturer's protocol.

Preparation of Liposomes

Twenty µl of C16-z13 peptide (10 mM in chloroform:methanol 2:1) was mixed with 20 µl phosphatidylcholine (100 mM in chloroform) and 10 µl cholesterol (100 mM in chloroform) in a round bottom flask and evaporated in a rotary evaporator. The sample was dried in a vacuum, dissolved in 500 µl 0.3M citric acid, and frozen and thawed three times, followed by sonication for 10 min. Five hundred µl of 0.2M $Na_2CO_3$ and 20 µl of 1 µM Qdot605 streptavidin was added and heated at 60° C. for 1 hour. After adding 1 ml of 20 mM Hepes buffer, pH7.2, the liposome solution was centrifuged at 90,000 rpm for 30 min at 4° C. and the pellet dissolved in PBS.

Cell Lines and Cell Culture

A human endometrial adenocarcinoma cell line, Ishikawa (Lessey, B. A., et al., 1996; Castelbaum, A. J., et al., 1997) was obtained. The human endometrial epithelial cell line HES (Desai, N. N., et al., 1994) was obtained. The endometrial adenocarcinoma, SNG-II, was described previously (Nozawa, S., et al., 1989). Endometrial adenocarcinoma lines RL95-2 and Hec1A; the human squamous cell carcinoma A431; and human cervical carcinoma HeLa cells were obtained from American Tissue Culture Collection, Manassas, Va. All cells were cultured in Dulbecco's modified Eagle's medium with high glucose supplemented with 10% fetal calf serum, 2 mM glutamine, 1 mM pyruvate, 100 Units/ml penicillin, and 100 µg/ml streptomycin, at 37° C. in a humidified incubator under 5% $CO_2$.

Phage Library Screening

A 6-week-old C57/BL6 female mouse was anesthetized with avertin, and 1 ml of a T7 phage library containing a total of $10^{11}$ clones was injected into the peritoneal cavity. After 30 min, the library was recovered by washing the peritoneal cavity with 10 ml PBS. This subtracted library was added to a monolayer of Ishikawa cells grown in a 3.5 cm tissue culture plate and incubated at 37° C. for 30 min, allowing bound phage to be internalized by endocytosis. Cells were washed 6 times with DME and detached by trypsinization. Cells were solubilized by 1% NP-40 in PBS, and competent BL21 bacteria were infected with the released phage. T7 phage was amplified in BL21 cells until lysis occurred. Amplified phage, $1 \times 10^7$ clones (1 ml), was subtracted again by the mouse peritoneum and selected by incubation with Ishikawa cells as described. This cycle was repeated three times. Binding of each cloned phage to target cells was determined by counting the number of phage plaques recovered from Ishikawa cells as a positive control or from A431 cells as a negative control. Sequencing of the phage clone was performed as described (Hoffman, J. A., et al., 2002).

Fluorescence Microscopy

Ishikawa cells and A431 cells were grown on glass coverslips in 3.5 cm tissue culture plates. Each phage clone including z13 was added to these cells, incubated at 4° C. for 15 min, washed with cold PBS, and fixed with 1% paraformaldehyde (PFA) in PBS. Phage was detected using rabbit anti-T7 antibody and FITC-conjugated goat anti-rabbit IgG antibody. After washing three times with PBS, cells were fixed with 1% paraformaldehyde in PBS and inspected under a Zeiss Axioplan fluorescence microscope. Ishikawa cells grown on glass coverslips were incubated in medium containing FITC-z13 peptide (1 µg/ml) at 37° C. for 15 min. After washing with PBS, cells were fixed with 1% PFA in PBS, and inspected under the fluorescence microscope. Qdot-encapsulated and C16-z13 peptide coated liposomes were prepared as described above. Ishikawa cells were incubated with these liposomes at 37° C. for 15 min, washed with PBS, fixed with 1% PFA, and inspected under the fluorescence microscope. Qdot605-conjugated peptide, Qdot-cys-z13, or control peptide, Qdot-cys-m2, was added to the culture at 100 nM and left at 37° C. for 15 min.

Phage Immunohistochemistry on Frozen Human Tissue Sections

Human tissues including uterine endometriosis (adenomyosis) were obtained from patients, after obtaining written informed consent from each patient. The Institutional Review Board of Shinshu University School of Medicine approved the use of human subjects for this study. These tissue specimens were fixed with 20% buffered formalin (pH 7.4) for 48 hours and then incubated with a 0.88 M hypertonic gum sucrose solution overnight. They were immediately frozen in an O.C.T. compound at −80° C. and sliced at 6 µm thickness. The frozen sections were placed on slides and stored frozen until use. Phage was overlayed on the sections at room temperature for 30 min, washed with PBS and fixed with 1% paraformaldehyde in PBS Immunohistochemistry of tissue sections was undertaken using rabbit anti-T7 phage antibody followed by immunoperoxidase reactions. Staining was visualized by DAB and hematoxylin was used for counterstaining.

Mouse model for peritoneal endometriosis. An endometriosis mouse model was constructed using the SCID mouse and human endometriosis tissues as described (Aoki, D., et al., 1994), except endometrial tissues were transplanted to the peritoneal wall. Briefly, human normal endometrial specimens were obtained during hysterectomy from patients who had undergone surgery for uterine myomas and ovarian cysts. Written informed consent was obtained from each patient. The use of human subjects for this study was approved by the Institutional Review Board of Keio University School of Medicine. After removing the myometrium from each specimen by gentle scraping, the remaining endometrium was cut into 2 mm cubes with a safety razor blade. Specimens were maintained in sterilized medium containing 30 ng/ml penicillin G (pH 7.4) until use. Each mouse under intraperitoneal anesthesia with avertin (50 mg/kg) was placed on its back and an incision about 2 cm in length was made in the abdomen. Two pieces of endometrial tissue, each a 2-mm cube, were grafted onto the peritoneal wall with absorbable suture material. Animals were maintained for up to 10 weeks.

B. Example 2

This example describes the discovery of peptides that bind selectively to endometriosis cells, the discovery of the binding target of the peptides, and demonstration of treatment of endometriosis in a baboon model. Endometriosis is a common gynecological disease associated with pelvic pain and infertility. Current treatments include oral contraceptives combined with non-steroidal anti-inflammatory drugs or surgery to remove lesions, all of which provide a temporary but not complete cure. As most endometriosis occurs on organ surfaces facing the peritoneum, a phage display library was subtracted with female mouse peritoneum tissue and phage clones were selected by binding to human endometrial epithelial cells. An endometriosis-targeting peptide internalized by cells, designated z13, was discovered. Proteomics analysis revealed the z13 receptor as the cyclic nucleotide gated channel β3, a sorting pathway protein. When z13 linked with an apoptosis-inducing peptide and with an endosome-escaping peptide were co-administered into the peritoneum of baboons with endometriosis, cells in lesions selectively underwent apoptosis with no effect on neighboring organs. This demonstrates a therapeutic capable of reducing or eliminating endometriosis from the human peritoneum.

Results

Identification of Peptides Targeting Peritoneal Endometriosis

It was realized that some, if not all, human endometrial adenocarcinoma cell lines would express cell surface proteins expressed in glandular epithelial cells in endometriosis. To devise a probe that specifically binds to the endometriosis surface but not to the surface of other organs facing the peritoneum, subtractive phage library screening was used (Eisenhardt et al., 2007; Zhang et al., 2001). A T7 phage based library ($10^9$ clones, $10^{11}$ pfu) of linear 9-mer peptides was injected into the peritoneal cavity of a female mouse to allow absorption of phage clones to the peritoneal surface in vivo for 1 hour. The pre-cleared library was recovered from peritoneal fluid and added to a monolayer of human endometrial adenocarcinoma Ishikawa cells cultured in vitro. Ishikawa cells were chosen as this line shares characteristics with mature endometrial epithelial cells (Castelbaum et al., 1997; Lessey et al., 1996). A goal was to identify a peptide internalized by endometrial glandular epithelial cells so that a drug conjugated with that peptide would penetrate target cells. Phage were incubated with live Ishikawa cells at 37° C. for 30 min to facilitate phage internalization. Selected phage clones were recovered after solubilization of cells with detergent and amplified in bacteria. After three rounds of subtractive library screening, the number of phage clones with Ishikawa cell-binding activity relative to the total number of added phage increased 10,000-fold (FIG. 1).

The third screen-positive phage pool was overlayed on frozen tissue sections of endometriosis lesions surgically isolated from endometriosis patients. Binding of phage to tissue was visualized by the immunoperoxidase method using rabbit anti-T7 phage antibody. Hematoxylin served as counterstain. Immunohistochemistry using an anti-phage antibody showed positive signals on glandular epithelial cells, particularly at apical cell surfaces in endometriosis. Weak signals were also detected in smooth muscle or stromal cells in the same sections. Neither the original phage library nor phage lacking inserts stained endometriosis tissues. These results indicate that the positive phage pool contained a clone or clones specifically binding to endometrial glandular epithelial cells.

Figure 2:
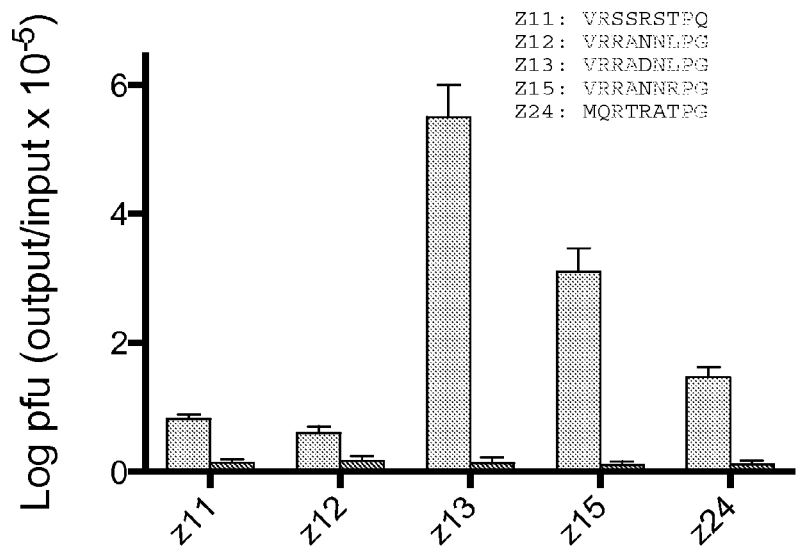
FIG. 2 is a graph of plaque forming units (log pfu) of phage binding to cells for different phage clones identified in the phage library screening. Binding of cloned phage to Ishikawa (left bars) and control A431 (right bars) cells. Each cloned phage was added to a monolayer of each cell line at 37° C. for 30 min. Internalized phage was counted by a plaque forming assay. Sequences are z11 (SEQ ID NO:7), z12 (SEQ ID NO:2), z13 (SEQ ID NO:3), z15 (SEQ ID NO:4), and z24 (SEQ ID NO:8).
Figure 3:
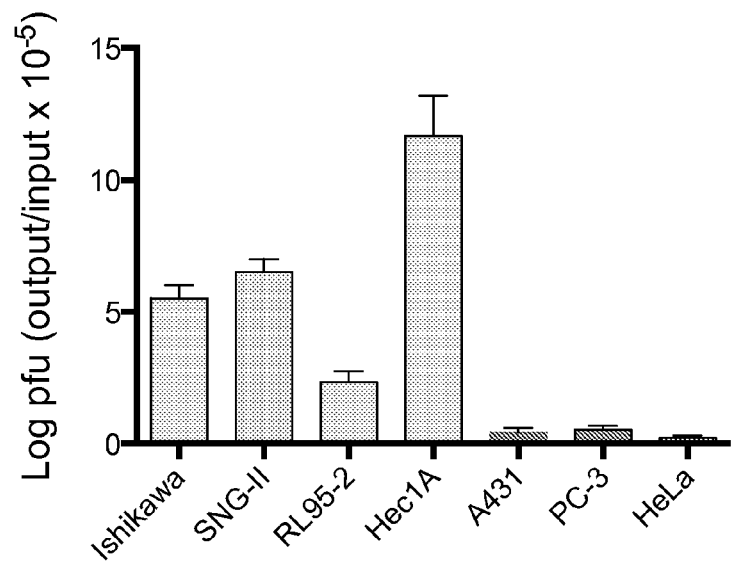
FIG. 3 is a graph of plaque forming units (log pfu) of z13 phage binding to different cells. Z13 phage binding to endometrial cell lines (first four bars) and control non-endometrial cell lines (last three bars). Each cloned phage was added to a monolayer of each cell line at 37° C. for 30 min. Internalized phage was counted by a plaque forming assay.

Sequencing of insert DNAs from isolated phage clones revealed the deduced consensus sequence VRRAXNXPG (SEQ ID NO:1; where X represents a varying amino acid residue) (FIG. 2). Although the number of phage clones with binding activity to endometrial cells was not determined, 24 clones in the selected phage out of 50 sequenced exhibited the consensus sequence, indicating that close to half of the selected phage bind to endometrial cells. The presence of the consensus sequence at this high frequency attests to the high specificity of selected clones. In vitro binding assays indicated that each clone bound to Ishikawa cells at higher efficiency than to control skin epidermoid carcinoma A431 cells. Among the clones, z13, which displayed the sequence VRRADNRPG (SEQ ID NO:3), was the strongest binder. Z13 phage bound to endometrial adenocarcinoma SNG-II, RL95-2, and Hec1A cells but not to A431, prostate cancer PC3, or cervical cancer HeLa cells (FIG. 3).

When z13 phage was injected into mouse peritoneum and peritoneal tissues were examined by immunohistochemistry using an anti-phage antibody, positive signals were not detected. To confirm specific binding of z13 phage to human endometriosis in vivo, human endometrial tissues were transplanted into the peritoneal wall of immunodeficient mice (Aoki et al., 1994), and z13 phage was injected peritoneally into mice. Endometriosis patient tissue was implanted in the SCID mouse peritoneal wall, phage displaying z13 peptide was injected peritoneally, and sections from the endometriosis implant were examined by immunohistochemistry using an anti-T7 phage antibody. Immunohistochemistry showed phage binding to glandular epithelial cells in the transplant, indicating that z13 peptide-displaying phage targeted human endometrial glandular epithelia in the mouse peritoneum.

To confirm z13 peptide binding activity, cys-z13 conjugated to fluorescent nanoshell Qdots was chemically synthesized. When Qdot-z13 was added to the culture medium of live Ishikawa cells, it bound to Ishikawa but not to A431 cells. A z13 peptide with an N-terminal FITC-tag also bound to Ishikawa and not A431 cells. Micrographs of Ishikawa cells showed a punctuate cytoplasmic staining pattern, indicating that z13 is internalized to endosomes.

Identification of the z13 Peptide Receptor

To identify the z13 peptide receptor and support a clinically relevant therapeutic strategy, Ishikawa cells were surface biotinylated and lysed, and then lysates were incubated with z13 peptide-conjugated agarose beads. Bead-bound materials were then eluted by z13 peptide, and biotinylated proteins detected by avidin blot, revealing a single 68 kDa protein. To identify this protein, the microsomal membrane fraction was prepared from endometriosis tissue surgically removed from patients. Membrane proteins solubilized with detergent were applied to a z13 peptide affinity column and column-bound materials were eluted by z13 peptide. A silver-stained gel revealed a 68 kDa protein, and proteomic analysis identified it as the cyclic nucleotide-gated channel beta 3 or CNGB3. CNGB3 protein has six transmembrane domains (Peng et al., 2003). A large part of this protein is buried in the lipid bilayer, the N- and C-terminal domains are cytoplasmic, and the z13-binding regions are extracellular.

To assess binding of FITC-z13 to CNGB3, HeLa cells were transfected with a mammalian expression vector encoding a CNGB3-MYC fusion protein or with control empty vector. Fluorescence micrographs were made of HeLa cells transfected by control vector or with an expression vector encoding CNGB3-MYC. The micrographs showed binding of FITC-z13 peptide to HeLa cells transfected with mammalian expression vectors, immunostained with anti-MYC followed by Alexa 549-conjugated anti-mouse IgG antibody, and merged images including DAPI to indicate nuclear staining. FITC-z13 did not bind to vector-transfected control cells. HeLa cells transfected with the CNGB3-MYC expression construct and stained by anti-MYC antibody showed an endosome-like pattern. When FITC-z13 was added to culture medium of CNGB3-MYC-expressing HeLa cells, FITC-z13 bound to sites marked by MYC-epitope expression. These results indicate that recombinant CNGB3 expressed in a mammalian cell has z13 peptide binding activity on the cell surface and is internalized to endosome, indicating that CNGB3 is the z13 receptor.

To examine CNGB3 protein expression in endometriosis, a mouse monoclonal antibody was generated against an epitope displayed within the human CNGB3 cytoplasmic domain (designated 3B2; amino acids 728 to 750 of SEQ ID NO:34). Antibody specificity was validated by immunostaining of CNGB3-Myc expressed in HeLa cells. This antibody strongly stained glandular epithelia of endometriosis in tissue sections. Peritoneal surfaces from cycling women without endometriosis were not stained by this antibody, whereas those from endometriosis patients were stained by this antibody, indicating that endometrial cells are spread across a wide area on the peritoneum of endometriosis patients. Eutopic endometrial tissues at secretory and proliferative phases were weakly stained by this antibody Immunohistochemistry of human tissues showed this antibody did not stain the surface of organs facing the peritoneal cavity.

Induced Apoptosis of CNGB3-Expressing Cells

The above results support the discovery that z13 peptide can be used to deliver a drug against endometriosis expressing CNGB3. The pro-apoptotic 18-mer peptide, KLAKLAKKLAKLAKKLAK (SEQ ID NO:40) (abbreviated KLAK in this study, which was devised from [KLAKLAK]$_2$ peptide (SEQ ID NO:26; del Rio et al., 2001; Ellerby et al., 1999; Gerlag et al., 2001)) was chosen as an example therapeutic. In these types of peptides, one side of alpha-helix is hydrophilic and the other side is hydrophobic (FIG. 4, center), which has the overall effect of disrupting mitochondrial membranes. In dKLAK-z13, the KLAK moiety was made using d-amino acids to prevent proteolysis.

When dKLAK-z13 was added to culture medium of HEK293T cells transfected by expression vector for CNGB3-MYC, apoptosis was not induced, however. It was realized that this lack of effect could be due to the fact that receptor-bound dKLAK-z13 localizes to the luminal side of endosomes, a prediction supported by the endosome-like pattern of fluorescent z13. To release dKLAK-z13 from the endosomes to the cytoplasm, an endosome-escaping 18-mer peptide HLAHLAHHLAHLAHHLAH (SEQ ID NO:38; here abbreviated as HLAH) was devised by replacing lysines in KLAKLAK (SEQ ID NO:39) with histidines, to provide histidine-rich sequences capable of destabilizing endosome membranes at acidic pH (Midoux et al., 2002; Pichon et al., 2001). When biotinylated z13 was bound to HEK293T cells overexpressing CNGB3-MYC protein, biotin-z13 showed a punctuate endosome/lysosome-like pattern, whereas it showed diffuse cytoplasmic signals in the presence of HLAH-z13, indicating that HLAH-z13 promotes endosome-escaping activity releasing biotin-z13 from endosomes to the cytoplasm. For this experiment, biotin-z13 was bound to CNGB3-MYC expressing HEK293T cells at 37° C. for 30 min with or without HLAH-z13. Cells were stained by Alexa 488-conjugated avidin followed by DAPI nuclear staining.

Figure 5:
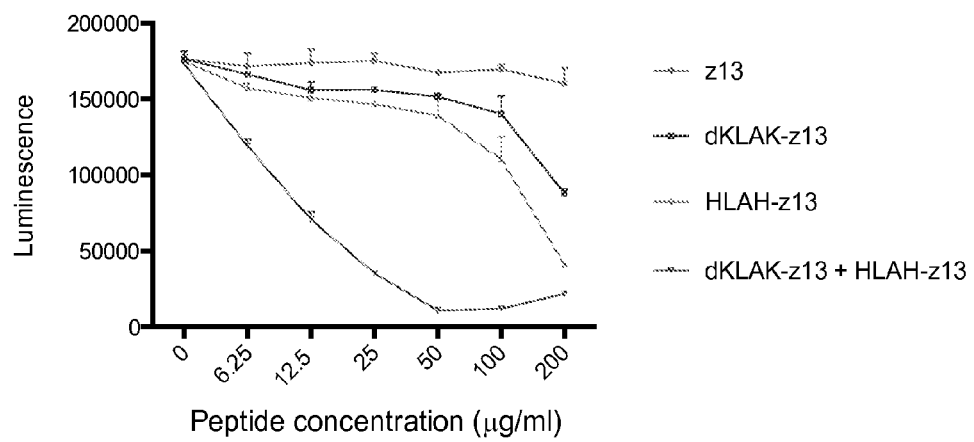
FIG. 5 is a graph of luminescence of live cells cultured in medium containing peptides on CNGB3-MYC expressing A431 cells versus peptide concentration for the four different peptide combinations: z13, dKLAK-z13, HLAH-z13, or dKLAK-z13 plus HLAH-z13. Cells were cultured in medium containing each peptide at the indicated concentrations at 37° C. for 1 hour. ATP levels were measured by CellTiter Glo (Promega). Lines represent, in order from top to bottom: z13, dKLAK-z13, HLAH-z13, and dKLAK-z13 plus HLAH-z13.
Figure 7:
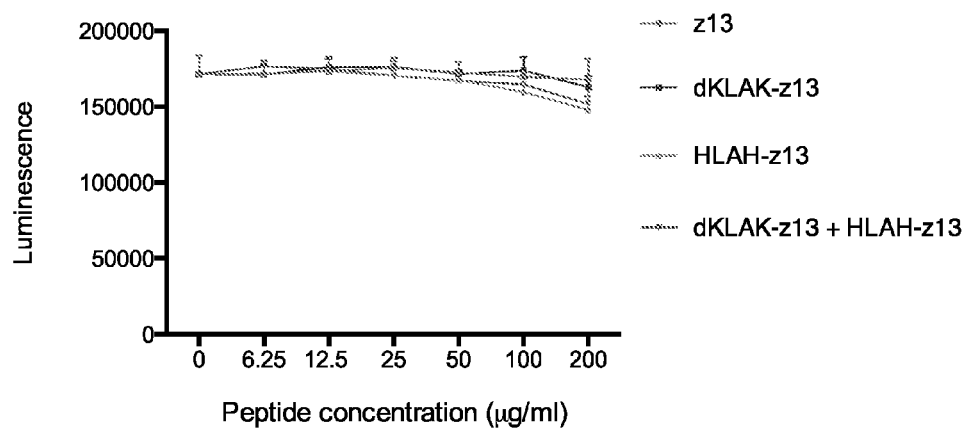
FIG. 7 is a graph of luminescence of live cells cultured in medium containing peptides on CNGB3-MYC negative A431 cells versus peptide concentration for the four different peptide combinations: z13, dKLAK-z13, HLAH-z13, or dKLAK-z13 plus HLAH-z13. Cells were cultured in medium containing each peptide at the indicated concentrations at 37° C. for 1 hour. ATP levels were measured by CellTiter Glo (Promega). Lines represent, in order from top to bottom: dKLAK-z13, z13, dKLAK-z13 plus HLAH-z13, and HLAH-z13.

Cytotoxic activity of dKLAK-z13 was then assessed in the presence of HLAH-z13 using a cell viability assay (FIG. 5). When CNGB3-expressing HEK293T cells were cultured in medium containing z13, dKLAK-z13, or HLAH-z13 at 37° C. for 1 hour, cell viability was not affected except at high concentration of dKLAK-z13 (at 200 µg/ml) or HLAH-z13 (at 50 µg/ml). By contrast, a mixture of dKLAK-z13 and HLAH-z13, each at low concentration, showed clear cytotoxicity, whereas the mixture did not show a toxic effect to control A431 cells (FIG. 7). For this experiment, cells were cultured at 37° C. for 20 hours in medium containing no peptide; z13 (100 µg/ml); dKLAK (100 µg/ml); dKLAK-z13 (100 µg/ml); HLAH-z13 (25 µg/ml); or dKLAK-z13 (100 µg/ml) plus HLAH-z13 (25 µg/ml). The same mixture showed time-dependent cytotoxicity in CNGB3-expressing HEK293T cells, whereas it had no effect on control A431 cells. These results indicate that a mixture of dKLAK-z13 and HLAH-z13 specifically targets CNGB3-expressing cells to induce apoptotic cell death.

Targeted Apoptosis of Peritoneal Endometriosis In Vivo in the Baboon

The effect of a mixture of dKLAK-z13 and HLAH-z13 peptides on baboon endometriosis models was test in vivo. Three female baboons with advanced endometriosis were identified based on clinical symptoms, which include infertility and behavior consistent with the inability to conceive, namely, dysmenorrhea and extended menses. Under general anesthesia, a 5 mm diagnostic laparoscope was used to inspect pelvic organs, which confirmed endometriosis. After washing the peritoneal cavity with PBS, a mixture of dKLAK-z13 (100 µg/ml) and HLAH-z13 (25 µg/ml) peptides dissolved in PBS (150 ml) was injected into the peritoneum. Animals were left approximately 20 hours after administration of the peptides to allow apoptosis to occur. Endometriosis lesions and surrounding peritoneal tissues were collected post mortem.

Histology of hematoxylin and eosin stained tissue sections revealed evidence of endometriosis in all three animals treated with a mixture of dKLAK-z13 and HLAH-z13 peptides. TUNEL assays of endometriosis lesions collected from three untreated control baboons revealed infrequent TUNEL-positivity in gland tissue (FIG. 6, left column) By contrast, TUNEL-positive glands were found in tissues collected from all three baboons treated with the dKLAK-z13 and HLAH-z13 peptide mixture (FIG. 6, right column) Those signals were seen in glandular epithelial cells in ovarian endometriosis and in the lumen of endometrial gland in the omentum. No evidence of apoptosis was detected in epithelial cells facing peritoneum in liver, kidney, spleen, colon, and stomach. These results show that z13-targeted induced apoptosis occurred in endometriosis model in baboons in vivo.

Discussion

Figure 4:
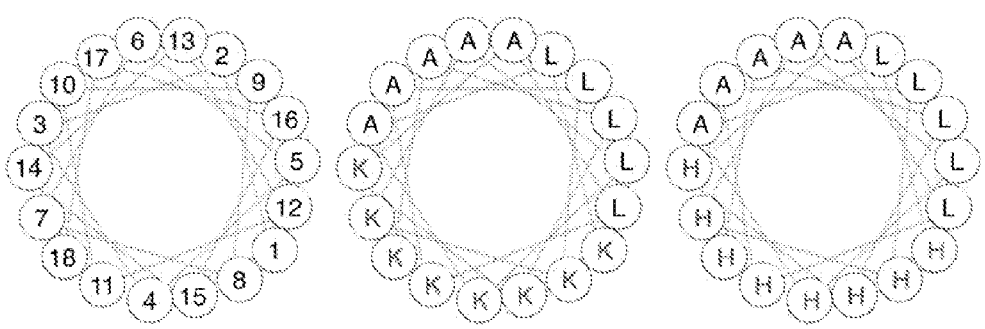
FIG. 4 shows helical wheel diagrams of alpha helix (left), and alignment of KLAKLAKKLAKLAKKLAK (SEQ ID NO:40) (center) and HLAHLAHHLAHLAHHLAH (SEQ ID NO:38) (right). Note that polar or hydrophilic amino acids are concentrated on one side of helix, and hydrophobic amino acids on the other.

Peptides that target endometriosis but not non-endometrial cells facing peritoneal cavity were identified. Endometriosis is notoriously resistant to apoptosis (Beliard et al., 2004; Dmowski et al., 2001). By combining endometriosis-targeting peptide with pro-apoptotic KLAK peptide (SEQ ID NO:40; del Rio et al., 2001; Ellerby et al., 1999) and that with newly developed potent endosome-escaping HLAHLAH peptide (SEQ ID NO:38; FIG. 4), apoptosis was induced in cells of endometriosis in vivo in baboon models. These results provide evidence that these reagents represent therapeutics for endometriosis.

Phage display technology allows unbiased identification of a factor in the absence of biochemical or cell biological information. The strength of this technology is the very large size of the library, which contains as many as $10^9$ clones. In addition, identified short peptide sequences can be synthesized chemically and modified for further functionality. This technology has been successfully used to identify peptide ligands specific for organ vasculature (Ruoslahti, 2002), tumor vasculature (Laakkonen et al., 2004; Oku et al., 2002), and cell adhesion molecules (Fukuda et al., 2000; Sugihara et al., 2007). In this example, subtractive library screening was used to identify a peptide, z13, which targets endometriosis tissue by eliminating phage clones with binding activity to the peritoneal surface and organs facing the peritoneum.

The z13 receptor CNGB3 is highly expressed in endometrial glandular epithelial cells and peritoneal surfaces in specimens collected from endometriosis patients, whereas CNGB3 protein was not detected in peritoneal surfaces and organs facing peritoneum in healthy women. This indicates that peritoneally-injected drug with CNGB3-binding activity can target macroscopically invisible endometrial epithelial cells adhering to the peritoneal surfaces. Such targeting activity by z13 is significant, as these cells are difficult to remove surgically and if they are left in peritoneum they could potentially develop into endometriosis lesions.

When z13 peptide was conjugated to an apoptosis-inducing dKLAK peptide, this construct did not induce apoptosis of CNGB3-expressing cells. It was realized that dKLAK-z13 binds to CNGB3 on the endometrial glandular cell surface and is internalized to endosomes but not released to the cytoplasm where mitochondria reside. To circumvent this problem, an endosome-escaping peptide comprised of histidine-rich sequences was developed (FIG. 4) (Jones et al., 1992; Martin and Rice, 2007; Midoux et al., 2002). The pKa of the histidine imidazole group is 6.5, and thus histidine behaves as hydrophobic residue at neutral pH, whereas it is protonated and behaves as a basic peptide in the slightly acidic endosomal milieu. Once protonated, the peptide disrupts endosomal membranes, destabilizing endosomes. An endosome-escaping HLAH peptide was devised by replacing K in KLAK peptide with H (FIG. 4). The HLAH peptide devised here can have wide applications to enhance activity of drugs that are not functional when trapped in endosomes. It needs to be emphasized that this strategy should be applicable to any cell surface protein of sorting pathway, regardless of physiological activity of targeting proteins.

Figure 6:
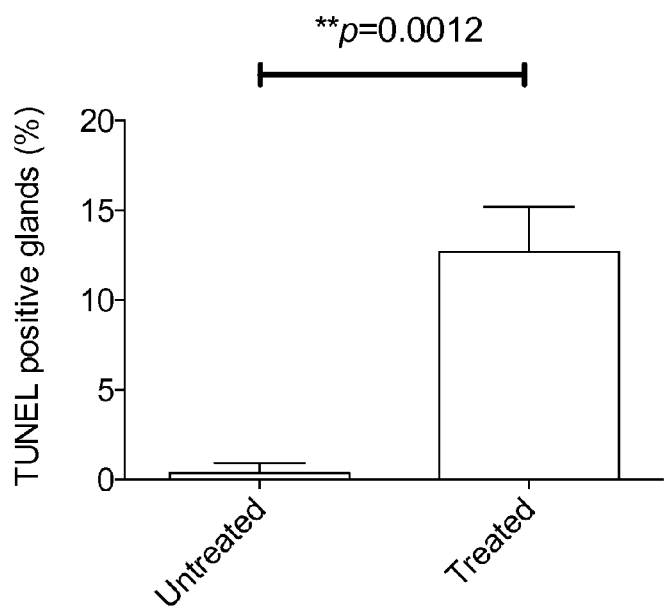
FIG. 6 is a graph of TUNEL positive glands in treated and untreated baboons indicating induced apoptosis in baboon endometriosis tissue in vivo. This quantitative TUNEL analysis shows the percentage of TUNEL-positive endometrial glands in tissues from three control untreated baboons compared with three animals treated with a mixture of dKLAK-z13 and HLAH-z13 peptides. Those percentages from untreated and treated animals were 0.33%±0.57 and 12.67%±2.517, respectively.

Human endometriosis tissues reportedly exhibit minimal apoptosis (Beliard et al., 2004; Hoffman et al., 2002). Indeed, apoptosis was rarely detected in endometriosis tissues in untreated baboons (FIG. 6). By contrast, in baboons treated overnight with a mixture of dKLAK-z13 and HLAH-z13, significant apoptosis was detected in endometriosis lesions (FIG. 6). This example indicates that dKLAK-z13 and HLAH-z13 can be used as clinically-relevant therapeutics to remove endometriosis lesions from the peritoneum of human patients.

Experimental Procedures

Synthetic Peptides

The following peptides were synthesized by GenScript (Piscataway, N.J.): z13, VRRADNRPG (SEQ ID NO:3); irrelevant peptide, RGMSDTTAL (SEQ ID NO:9); fluorescent FITC-z13; dKLAKLAK-z13, KLAKLAKKLAKLAK-KLAKVRRADNRPG (d-amino acids italicized; SEQ ID NO:29); HLAH-z13, HLAHLAHHLAHLAHHLAHVR-RADNRPG (SEQ ID NO:28; CNGB3 antigen, KENEDK-GKENEDKDKGREPEEKP (3B2 epitope; amino acids 728 to 750 of SEQ ID NO:34).

Phage Library Screening

A T7 phage library displaying random 9-mer peptide sequences constructed in the T7 Select 415-1b vector (Novagen, Madison, Wis.) was provided by Dr. Erkki Ruoslahati, Sanford-Burnham Medical Research Institute. A 6-week-old C57/BL6 female mouse was anesthetized with Avertin, and 1 ml of the T7 phage library containing a total of $10^{11}$ clones was injected into the peritoneal cavity and left for 1 hour. The library was recovered by washing the peritoneal cavity with 10 ml of 20 mM sodium phosphate buffer, pH 7.4, containing 0.15 M sodium chloride (PBS). This subtracted library was added to a monolayer of Ishikawa cells grown in a 3.5-cm tissue culture plate and incubated at 37° C. for 30 min, allowing bound phage to be internalized by endocytosis. Cells were washed 6 times with DMEM and detached by trypsinization. Cells were solubilized by 1% NP-40 in PBS, and competent BL21 bacteria were added. Phage-infected bacteria were cultured at 37° C. until lysis occurred. The amplified phage, $1\times10^7$ clones (1 ml), were subtracted again using mouse peritoneum and selected by incubation with Ishikawa cells as described. This cycle was repeated 3 times. Binding of each cloned phage to target cells was determined by counting the number of phage plaques recovered from cells relative to the phage numbers added to cells. Sequencing of the phage clone was performed as described (Hoffman et al., 2002).

Targeted Apoptosis of Peritoneal Endometriosis in the Baboon

The protocol and use of the baboon model of endometriosis were approved by the Institutional Animal Care and Use Committee (IACUC) of Texas Biomedical Research Institute. Three female baboons with advanced endometriosis were identified based on clinical symptoms, which include infertility and behavior consistent with the inability to conceive, namely, dysmenorrhea and extended menses. Candidate baboons also received an ultrasound as part of screening for study assessment. Under satisfactory anesthesia, abdominal cavity was insufflated using a 1.5 L per minute insufflator and Veress needle until the abdomen is distended and tympanic on percussion. A 5 mm diagnostic laparoscope was used to inspect pelvic organs. PBS (300 ml) was injected into the peritoneal cavity, adhesions were dissociated, and the peritoneum washed. Three baboons received PBS containing a mixture of dKLAK-z13 (100 μg/ml) and HLAH-z13 (25 μg/ml) in 150 ml through a laparoscope into the peritoneum. Gas was evacuated from the peritoneum and the incisions sutured. Baboons were left approximately 20 hours after administration and euthanized for tissue collection. Tissues were fixed with buffered formalin, and paraffin sections were made for histopathological analysis including TUNEL assay.

Quantitative TUNEL Analysis

Endometriosis lesions were identified in paraffin-embedded sections stained by hematoxylin and eosin. Endometrial glands were confirmed by immunostaining with an anti-keratan sulfate antibody (5D4) (Aplin et al., 1998) and an anti-estrogen receptor antibody (Nisolle et al., 1997). The number of glands counted for each baboon ranged from 8 to 26. A gland was scored as TUNEL-positive if it contained any TUNEL-positive cells. The number of TUNEL-positive glands in total glands was expressed as relative TUNEL positivity (%). Statistical analysis was performed using Student's two-tailed t-test using GraphPad Prism v.6 software.

Human Subjects

Endometrial specimens were obtained from patients undergoing hysterectomy for uterine myomas and ovarian cysts after each patient provided written informed consent. The use of human subjects in this study was approved by the Institutional Review Board (IRB) of Keio University School of Medicine. Formalin-fixed and paraffin-embedded tissue blocks of normal endometrium with adenomyosis (three patients) and peritoneum without endometriosis (four patients) were retrieved from pathology file of Department of Laboratory Medicine, Shinshu University Hospital. The IRB of Shinshu University School of Medicine approved the study plans, and granted a waiver of informed consent, since diagnostic use of the samples was completed before this study and there was no risk to the patients. All samples were number coded to protect patient confidentiality.

Use of Mice

The protocol for creation and use of the mouse model of endometriosis was approved by the Institutional Animal Care and Use Committee (IACUC) of Keio University School of Medicine. The protocols for monoclonal antibody production and use of mice for phage library screening were approved by the IACUC of the Sanford-Burnham Medical Research Institute.

Cell Lines and Culture

All cells were cultured in DME/F12 (50:50) mixed medium supplemented with 10% fetal calf serum, 2 mM glutamine, 1 mM pyruvate, 100 units/ml penicillin, and 100 µg/ml streptomycin at 37° C. in a humidified incubator under 5% $CO_2$.

Phage Immunohistochemistry Using Frozen Human Tissue Sections

Tissues were fixed with 20% buffered formalin (pH 7.4) for 48 hours and then incubated with a 0.88 M hypertonic gum-sucrose solution overnight. The tissues were immediately frozen in O.C.T. compound (Sakura Finetechnical, Tokyo, Japan) at −80° C. and sliced at 6 µm thickness. Frozen sections were placed on slides and stored frozen until use. Phage was overlaid on the sections at room temperature for 30 min, and sections were then washed with PBS and fixed with 1% paraformaldehyde (PFA) in PBS. Immunohistochemistry was undertaken using a rabbit anti-T7 phage antibody followed by immunoperoxidase reactions. Polyclonal rabbit anti-T7 phage antibodies were generated by Drs. P. Laakkonen, J. A. Hoffman, K. Pokka, and E. Ruoslahti, Sanford-Burnham Medical Research Institute. These antibodies do not stain frozen or paraffin sections of normal human and mouse tissues Staining was visualized by DAB (Zymed/Invitrogen, Carlsbad, Calif.) and hematoxylin was used for counterstaining.

Fluorescence Microscopy

Ishikawa cells and A431 cells were grown on glass coverslips in 3.5-cm tissue culture plates. Ishikawa cells grown on glass coverslips were incubated in medium containing FITC-z13 peptide (1 µg/ml) at 37° C. for 15 min. After washes with PBS, cells were fixed with 1% PFA in PBS and inspected under a fluorescence microscope. Qdot-cys-z13 was prepared by conjugating cys-z13 to Qdot nanoparticles (Qdot antibody conjugation kit, Quantum Dot, Hayward, Calif.) in accordance with the manufacturer's protocol. Cells were inspected under a Zeiss Axioplan fluorescence microscope.

Mouse Model for Peritoneal Endometriosis

An endometriosis mouse model was constructed using SCID mice and human endometriosis tissues as we described previously (Aoki et al., 1994), except that endometrial tissues were transplanted onto the peritoneal wall. Briefly, endometrial specimens were obtained during hysterectomy from patients who had undergone surgery for uterine myomas and ovarian cysts. After removing the myometrium from each specimen by gentle scraping, the remaining endometrium was cut into 2-mm cubes with a razor blade. Specimens were maintained in sterilized medium containing 30 ng/ml penicillin G (pH 7.4) until use. Each mouse was anesthetized by intraperitoneal Avertin (50 mg/kg) administration and placed on its back, and an incision about 2 cm in length was made in the abdomen. Two 2-mm cubes of endometrial tissue were grafted onto the peritoneal wall with absorbable suture material. Animals were maintained for up to 10 weeks.

Cell Surface Biotinylation and z13 Peptide Affinity Chromatography

An Ishikawa cell monolayer was washed 3 times with PBS. The biotinylation reagent sulfo-NHS-LC-biotin (Pierce, Rockford, Ill.) was dissolved in PBS and added to cells at 0.5 mg/ml. Thirty minutes later, the monolayer was washed 3 times with 20 mM Tris-HCl buffer, pH 7.4, containing 0.15 M sodium chloride (TBS). Cells were scraped from plates with a rubber policeman and solubilized in TBS containing 50 mM octyl-thio-glucoside and protease inhibitors (Complete mini, Roche, Indianapolis, Ind.) at 4° C. The cell lysate obtained after centrifugation was precleared with agarose beads at 4° C. for 2 hours. The precleared lysate was then incubated with z13-conjugated agarose beads, which were prepared by conjugating cys-z13 peptide (1 mg) to sulfo-link agarose beads (1 ml, Pierce). Z13 beads were washed with TBS containing 50 mM octyl-thio-glucoside and bead-bound materials were then eluted with TBS/octyl-thio-glucoside buffer containing z13 peptide (1 mg/ml). Biotinylated proteins eluted from the z13 beads were detected by SDS-PAGE followed by peroxidase avidin blot and an ECL (Amersham, Piscataway, N.J.) chemiluminescence reaction.

Z13 Peptide Affinity Chromatography and Proteomics

Surgically isolated endometriosis tissue (2 g) was homogenized in 100 ml TBS containing protease inhibitors (Complete mini, Roche). The homogenate was centrifuged at 2,000×g for 15 minutes, and the resulting supernatant was centrifuged at 100,000×g for 60 minutes. The pellet (membrane fraction) was resuspended in TBS containing 50 mM octyl-thio-glucoside and applied to 50 µl z13-conjugated agarose beads as described above. Z13 beads were washed 3 times with 1.5 ml TBS containing 50 mM octyl-thio-glucoside and then washed 3 times with 50 µl of the same buffer containing irrelevant peptide (1 mg/ml). Bead-bound materials were eluted with 50 µl of buffer containing z13 peptide (1 mg/ml). Eluted proteins were resolved on SDS-PAGE and detected by silver staining. A single band at 68 kDa was excised from the gel, digested with trypsin, and analyzed by MALDI-TOF mass spectrometry at the proteomics facility at the Sanford-Burnham Medical Research Institute.

Monoclonal Anti-CNGB3 Antibody and Immunohistochemistry

A peptide sequence of human CNGB3, corresponding to $K^{721}$ to $P^{750}$, was synthesized by GenScript. A cysteine was added at the C-terminus for conjugation to keyhole limpet hemocyanin (Immunopure KLH, Pierce) using a SMPB cross-linker (Pierce) according to the manufacturer's protocol. Female Balb/c mice were immunized with this conjugate, and spleens were isolated from the immunized mice. Lymphocytes released from the spleen were fused to mouse myeloma B3X cells, and hybridoma clones were screened by immunostaining as Ishikawa (positive) and A431 (negative) cells. A hybridoma clone was subcloned by a limited dilution, establishing the 3B2 clone. Tissue sections from endometriosis patients were obtained from Folio Biosciences (Columbus, Ohio). A normal uterine endometrium tissue microarray (60 cores) and a normal tissue microarray (60 cores) were obtained from Imgenex (San Diego, Calif.). Antigen retrieval was performed by autoclaving sections at 110° C. for 1 min in antigen retrieval solution (Vector Laboratories). Immunohistochemistry with 3B2 (mouse IgG) was performed using an ABC kit (Vector Laboratories) with a DAB color reaction and hematoxylin counterstaining.

Expression of Recombinant CNGB3

CNGB3 cDNA was kindly provided by Dr. Hisao Ueyama, Department of Ophthalomology, Shiga University of Medical Science, Japan. cDNA encoding full-length CNGB3 was excised by HindIII and BsrGI and ligated into the HindIII and Asp718I sites of pcDNA3.1/myc-His-B vector (Invitrogen). HeLa cells were transfected with this vector, and expression of CNGB3-MYC/His fusion protein was determined by immunohistochemistry with an anti-MYC antibody and the anti-CNGB3 antibody (clone 3B2) described above. To test binding of z13 peptide to CNGB3, FITC-z13 was added (5 µg/ml) to the medium of HeLa cells transfected by the above-described vector and incubated at 37° C. for 15 min. Cells were washed with PBS, fixed with 4% PFA in PBS, and observed under a fluorescence microscope.

Targeted Apoptosis by dKLAK-z13 and HLAH-z13

Each peptide was dissolved in dimethylsulfoxide at 100 µg/µl. Each peptide was added to the medium of cells, and the cells were cultured at 37° C. for 20 hours. Apoptosis of CNGB3-Myc cDNA-transfected HEK293T cells was determined by TUNEL assay using the ApopTag immunoperoxidase kit (Chemicon, Temecula, Calif.).

C. Example 3

Peptides including an endosome escape signal, a targeting peptide, and an effector molecule were synthesized and tested for function. The specific peptides were:

```
KLA-HLA-z13:
                                        (SEQ ID NO: 45)
KLAKLAKKLAKLAKHLAHLAHHLAHLAHVRRADNRPG;
and HLA-KLA-z13:
                                        (SEQ ID NO: 53)
HLAHLAHHLAHLAHKLAKLAKKLAKLAKVRRADNRPG.
```

Figure 8:
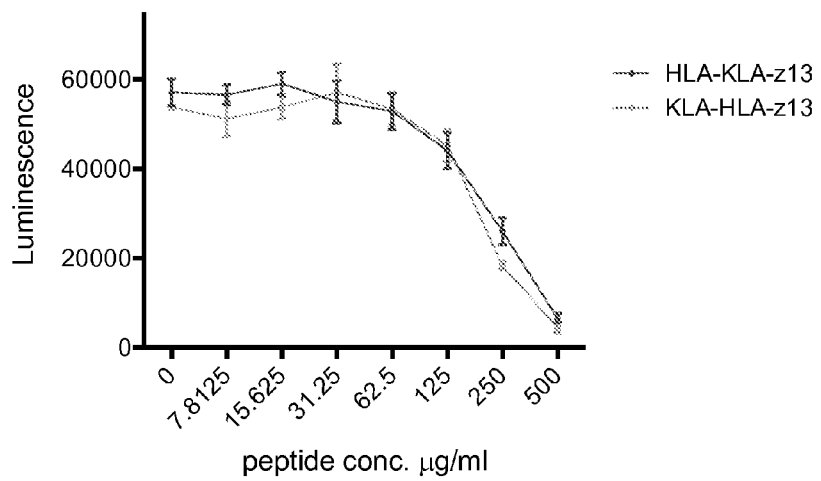
FIG. 8 is a graph of luminescence versus peptide concentration in μg/ml. The graph shows cell viability of CNGB3-positive A431 cells after incubating cells with KLA-HLAhybrid z13 peptides. Cells were cultured in medium containing each peptide at indicated concentrations at 37° C. for 6 hours. ATP levels were measured by CellTiter Glo (Promega).

The effect of these peptides was tested using CNGB3-positive A431 cells, which was generated by transfecting A431 cells with CNGB3-Myc gene driving lenti viral vector. Cell viability assay measuring ATP (FIG. 8) and TUNEL assay showed that both hybrid peptides induced apoptosis to CNGB3-positive A431 cells. The assays used detected no difference between these two peptides. The TUNEL assay was of CNGB3-MYC expressing A431 cells after culturing in medium containing KLA-HLA-z13 for 24 hours. The TUNEL assay shows a dose-dependent increase in the frequency of TUNEL-positive cells. A similar result was obtained by HLA-KLA-z13.

REFERENCES

Amsterdam, L. L., Gentry, W., Jobanputra, S., Wolf, M., Rubin, S. D., and Bulun, S. E. (2005). Anastrazole and oral contraceptives: a novel treatment for endometriosis. *Fertil Steril* 84, 300-304.

Aoki, D., Katsuki, Y., Shimizu, A., Kakinuma, C., and Nozawa, S. 1994. Successful heterotransplantation of human endometrium in SCID mice. *Obstet Gynecol* 83:220-228.

Aplin, J. D., Hey, N. A., and Graham, R. A. (1998). Human endometrial MUC1 carries keratan sulfate: characteristic glycoforms in the luminal epithelium at receptivity. *Glycobiology* 8, 269-276.

Arap, W., Pasqualini, R. & Ruoslahti, E. (1998) Science 279, 377-80.

Arici, A., Matalliotakis, I., Goumenou, A., Koumantakis, G., Fragouli, Y. & Mahutte, N. G. (2003) Am J Reprod Immunol 49, 70-4.

Arimoto, T., Katagiri, T., Oda, K., Tsunoda, T., Yasugi, T., Osuga, Y., Yoshikawa, H., Nishii, O., Yano, T., Taketani, Y., et al. 2003. Genome-wide cDNA microarray analysis of gene-expression profiles involved in ovarian endometriosis. *Int J Oncol* 22:551-560.

Awwad, J. T., Sayegh, R. A., Tao, X. J., Hassan, T., Awwad, S. T., and Isaacson, K. 1999. The SCID mouse: an experimental model for endometriosis. *Hum Reprod* 14:3107-3111.

Barbieri, R. L. & Missmer, S. (2002) Ann N Y Acad Sci 955, 23-33; discussion 34-6, 396-406.

Barbieri, R. L. (1988) N Engl J Med 318, 512-4.

Beck, L., Mularoni, A., Cardis, P., Adessi, G. L., and Nicollier, M. 1995. Adenosine 3',5'-monophosphate mediates progesterone effect on sulfate uptake in endometrial epithelial cells. *Endocrinology* 136:1737-1743.

Beliard, A., Noel, A., and Foidart, J. M. (2004). Reduction of apoptosis and proliferation in endometriosis. *Fertil Steril* 82, 80-85.

Brodzik, R., Glogowska, M., Bandurska, K., Okulicz, M., Deka, D., Ko, K., van der Linden, J., Leusen, J. H., Pogrebnyak, N., Golovkin, M., et al. 2006. Plant-derived anti-Lewis Y mAb exhibits biological activities for efficient immunotherapy against human cancer cells. *Proc Natl Acad Sci USA* 103:8804-8809.

Bruner-Tran, K. L., Rier, S. E., Eisenberg, E., and Osteen, K. G. (1999). The potential role of environmental toxins in the pathophysiology of endometriosis. *Gynecol Obstet Invest* 48 Suppl 1, 45-56.

Castelbaum, A. J., Ying, L., Somkuti, S. G., Sun, J., Ilesanmi, A. O., and Lessey, B. A. 1997. Characterization of integrin expression in a well differentiated endometrial adenocarcinoma cell line (Ishikawa). *J Clin Endocrinol Metab* 82:136-142.

Castillo, J., Winer, E., and Quesenberry, P. 2008. Newer monoclonal antibodies for hematological malignancies. *Exp Hematol* 36:755-768.

Clayton, G. M., Silverman, W. R., Heginbotham, L., and Morais-Cabral, J. H. 2004. Structural basis of ligand activation in a cyclic nucleotide regulated potassium channel. *Cell* 119:615-627.

Cramer, D. W. & Missmer, S. A. (2002) Ann N Y Acad Sci 955, 11-22; discussion 34-6, 396-406.

Das, S. K., Paria, B. C., Chakraborty, I., and Dey, S. K. 1995. Cannabinoid ligand-receptor signaling in the mouse uterus. *Proc Natl Acad Sci USA* 92:4332-4336.

De Maria, R., Lenti, L., Malisan, F., d'Agostino, F., Tomassini, B., Zeuner, A., Rippo, M. R., and Testi, R. Requirement for GD3 ganglioside in CD95- and ceramide-induced apoptosis. Science, 277: 1652-1655, 1997.

del Rio, G., Castro-Obregon, S., Rao, R., Ellerby, H. M., and Bredesen, D. E. 2001. APAP, a sequence-pattern recognition approach identifies substance P as a potential apoptotic peptide. *FEBS Lett* 494:213-219.

Desai, N. N., Kennard, E. A., Kniss, D. A. & Friedman, C. I. (1994) Fertil Steril 61, 760-6.

D'Hooghe, T. M. (1997). Clinical relevance of the baboon as a model for the study of endometriosis. *Fertil Steril* 68, 613-625.

DiMasi, J. A., Feldman, L., Seckler, A., and Wilson, A. (2010). Trends in risks associated with new drug development: success rates for investigational drugs. *Clin Pharmacol Ther* 87, 272-277.

Dmowski, W. P., Ding, J., Shen, J., Rana, N., Fernandez, B. B., and Braun, D. P. (2001). Apoptosis in endometrial glandular and stromal cells in women with and without endometriosis. *Hum Reprod* 16, 1802-1808.

Eisenhardt, S. U., Schwarz, M., Bassler, N., and Peter, K. 2007. Subtractive single-chain antibody (scFv) phage-display: tailoring phage-display for high specificity against function-specific conformations of cell membrane molecules. *Nat Protoc* 2:3063-3073.

Ellerby, H. M., Arap, W., Ellerby, L. M., Kain, R., Andrusiak, R., Rio, G. D., Krajewski, S., Lombardo, C. R., Rao, R., Ruoslahti, E., et al. 1999. Anti-cancer activity of targeted pro-apoptotic peptides. *Nat Med* 5:1032-1038.

Essler, M. & Ruoslahti, E. (2002) Proc Natl Acad Sci USA 99, 2252-7.

Eyster, K. M., Boles, A. L., Brannian, J. D., and Hansen, K. A. 2002. DNA microarray analysis of gene expression markers of endometriosis. *Fertil Steril* 77:38-42.

Farquhar, C. M. 2000. Extracts from the "clinical evidence". Endometriosis. *Bmj* 320:1449-1452.

Fukuda, M. N., Sato, T., Nakayama, J., Klier, G., Mikami, M., Aoki, D. & Nozawa, S. (1995) Genes Dev 9, 1199-210.

Fukuda, M. N., Ohyama, C., Lowitz, K., Matsuo, O., Pasqualini, R., Ruoslahti, E., and Fukuda, M. 2000. A peptide mimic of E-selectin ligand inhibits sialyl Lewis X-dependent lung colonization of tumor cells. *Cancer Res* 60:450-456.

Gerlag, D. M., Borges, E., Tak, P. P., Ellerby, H. M., Bredesen, D. E., Pasqualini, R., Ruoslahti, E. & Firestein, G. S. (2001) Arthritis Res 3, 357-61.

Giudice, L. C., and Kao, L. C. 2004. Endometriosis. *Lancet* 364:1789-1799.

Gong, Y., Murphy, L. C. & Murphy, L. J. (1994) J Steroid Biochem Mol Biol 50, 13-9.

Grummer, R., Schwarzer, F., Bainczyk, K., Hess-Stumpp, H., Regidor, P. A., Schindler, A. E., and Winterhager, E. 2001. Peritoneal endometriosis: validation of an in-vivo model. *Hum Reprod* 16:1736-1743.

Haffner, M. E., Whitley, J. & Moses, M. (2002) Nat Rev Drug Discov 1, 821-5.

Hayes, E. C., and Rock, J. A. (2002). COX-2 inhibitors and their role in gynecology. Obstet Gynecol Surv 57, 768-780.

Hoffman, J. A., Laakkonen, P., Porkka, K., and Ruoslahti, E. 2002. *Phage Display: A practical Approach*: Oxford University Press.

Houston, D. E. 1984. Evidence for the risk of pelvic endometriosis by age, race and socioeconomic status. *Epidemiol Rev* 6:167-191.

Iwamori, M., Sakayori, M., Nozawa, S., Yamamoto, T., Yago, M., Noguchi, M., and Nagai, Y. 1989. Monoclonal antibody-defined antigen of human uterine endometrial carcinomas is Leb. *J Biochem (Tokyo)* 105:718-722.

Johnson, N., and Farquhar, C. (2006). Endometriosis. *Clin Evid*, 2449-2464.

Jones, M. K., Anantharamaiah, G. M., and Segrest, J. P. (1992). Computer programs to identify and classify amphipathic alpha helical domains. *J Lipid Res* 33, 287-296.

Kao, L. C., Germeyer, A., Tulac, S., Lobo, S., Yang, J. P., Taylor, R. N., Osteen, K., Lessey, B. A., and Giudice, L. C. 2003. Expression profiling of endometrium from women with endometriosis reveals candidate genes for disease-based implantation failure and infertility. *Endocrinology* 144:2870-2881.

Kessler, C. A., Moghadam, K. K., Schroeder, J. K., Buckley, A. R., Brar, A. K., and Handwerger, S. 2005. Cannabinoid receptor I activation markedly inhibits human decidualization. *Mol Cell Endocrinol* 229:65-74.

Kolonin, M. G., Saha, P. K., Chan, L., Pasqualini, R. & Arap, W. (2004) Nat Med 10, 625-32.

Laakkonen, P., Akerman, M. E., Biliran, H., Yang, M., Ferrer, F., Karpanen, T., Hoffman, R. M., and Ruoslahti, E. 2004. Antitumor activity of a homing peptide that targets tumor lymphatics and tumor cells. *Proc Natl Acad Sci USA*.

Lessey, B. A., Damjanovich, L., Coutifaris, C., Castelbaum, A., Albelda, S. M. & Buck, C. A. (1992) J. Clin. Invest. 90, 188-195.

Lessey, B. A., Ilesanmi, A. O., Castelbaum, A. J., Yuan, L., Somkuti, S. G., Chwalisz, K., and Satyaswaroop, P. G. 1996. Characterization of the functional progesterone receptor in an endometrial adenocarcinoma cell line (Ishikawa): progesterone-induced expression of the alpha1 integrin. *J Steroid Biochem Mol Biol* 59:31-39.

Malisan, F. and Testi, R. GD3 ganglioside and apoptosis. Biochim Biophys Acta, 1585: 179-187, 2002.

Martin, M. E., and Rice, K. G. (2007). Peptide-guided gene delivery. *Aaps J* 9, E18-29.

Matsuzaki, S., Canis, M., Pouly, J. L., Botchorishvili, R., Dechelotte, P. J., and Mage, G. 2006. Differential expression of genes in eutopic and ectopic endometrium from patients with ovarian endometriosis. *Fertil Steril* 86:548-553.

Matsuzaki, S., Canis, M., Vaurs-Barriere, C., Pouly, J. L., Boespflug-Tanguy, O., Penault-Llorca, F., Dechelotte, P., Dastugue, B., Okamura, K., and Mage, G. 2004. DNA microarray analysis of gene expression profiles in deep endometriosis using laser capture microdissection. *Mol Hum Reprod* 10:719-728.

Midoux, P., LeCam, E., Coulaud, D., Delain, E., and Pichon, C. 2002. Histidine containing peptides and polypeptides as nucleic acid vectors. *Somat Cell Mol Genet* 27:27-47.

Moutsatsou, P., and Sekeris, C. E. 1997. Estrogen and progesterone receptors in the endometrium. *Ann N Y Acad Sci* 816:99-115.

Murphy, A. A. 2002. Clinical aspects of endometriosis. *Ann N Y Acad Sci* 955:1-10; discussion 34-16, 396-406.

Murphy, A. A., Green, W. R., Bobbie, D., dela Cruz, Z. C., and Rock, J. A. 1986. Unsuspected endometriosis documented by scanning electron microscopy in visually normal peritoneum. *Fertil Steril* 46:522-524.

Nisolle, M., Casanas-Roux, F., and Donnez, J. (1997) Immunohistochemical analysis of proliferative activity and steroid receptor expression in peritoneal and ovarian endometriosis. *Fertil Steril* 68, 912-919.

Nozawa, S., Sakayori, M., Ohta, K., Iizuka, R., Mochizuki, H., Soma, M., Fujimoto, J., Hata, J., Iwamori, M. & Nagai, Y. (1989) Am J Obstet Gynecol 161, 1079-86.

Okada, A., Ueyama, H., Toyoda, F., Oda, S., Ding, W. G., Tanabe, S., Yamade, S., Matsuura, H., Ohkubo, I., and Kani, K. 2004. Functional role of hCngb3 in regulation of human cone cng channel: effect of rod monochromacy-associated mutations in hCNGB3 on channel function. *Invest Ophthalmol Vis Sci* 45:2324-2332.

Oku, N., Asai, T., Watanabe, K., Kuromi, K., Nagatsuka, M., Kurohane, K., Kikkawa, H., Ogino, K., Tanaka, M., Ishikawa, D., et al. 2002. Anti-neovascular therapy using novel peptides homing to angiogenic vessels. *Oncogene* 21:2662-2669.

Oku, N., Doi, K., Namba, Y., and Okada, S. 1994. Therapeutic effect of adriamycin encapsulated in long-circulating liposomes on Meth-A-sarcoma-bearing mice. *Intl Cancer* 58:415-419.

Olive, D. L., and Pritts, E. A. (2001). Treatment of endometriosis. *N Engl J Med* 345, 266-275.

O'Mahony, D., and Bishop, M. R. 2006. Monoclonal antibody therapy. *Front Biosci* 11:1620-1635.

Osteen, K. G., and Sierra-Rivera, E. (1997). Does disruption of immune and endocrine systems by environmental toxins contribute to development of endometriosis? *Semin Reprod Endocrinol* 15, 301-308.

Pan, Q., Luo, X., Toloubeydokhti, T., and Chegini, N. 2007. The expression profile of micro-RNA in endometrium and endometriosis and the influence of ovarian steroids on their expression. *Mol Hum Reprod* 13:797-806.

Pasqualini, R. & Ruoslahti, E. (1996) Nature 380, 364-6.

Pasqualini, R., Koivunen, E., Kain, R., Landenranta, J., Sakamoto, M., Stryhn, A., Ashmun, R. A., Shapiro, L. H., Arap, W. & Ruoslahti, E. (2000) Cancer Res 60, 722-7.

Peng, C., Rich, E. D., and Varnum, M. D. (2003). Achromatopsia-associated mutation in the human cone photoreceptor cyclic nucleotide-gated channel CNGB3 subunit alters the ligand sensitivity and pore properties of heteromeric channels. *J Biol Chem* 278, 34533-34540.

Pichon, C., Goncalves, C., and Midoux, P. 2001. Histidine-rich peptides and polymers for nucleic acids delivery. *Adv Drug Deliv Rev* 53:75-94.

Rajotte, D. & Ruoslahti, E. (1999) J. Biol. Chem. 274, 11593-11598.

Rajotte, D., Arap, W., Hagedorn, M., Koivunen, E., Pasqualini, R. & Ruoslahti, E. (1998) J Clin Invest 102, 430-437.

Rasmussen, U. B., Schreiber, V., Schultz, H., Mischler, F. & Schughart, K. (2002) Cancer Gene Ther 9, 606-12.

Rier, S., and Foster, W. G. (2002). Environmental dioxins and endometriosis. *Toxicol Sci* 70, 161-170.

Rier, S. E. (2002). The potential role of exposure to environmental toxicants in the pathophysiology of endometriosis. *Ann N Y Acad Sci* 955, 201-212; discussion 230-202, 396-406.

Rier, S. E., Martin, D. C., Bowman, R. E., Dmowski, W. P., and Becker, J. L. (1993). Endometriosis in rhesus monkeys (*Macaca mulatta*) following chronic exposure to 2,3,7,8-tetrachlorodibenzo-p-dioxin. *Fundam Appl Toxicol* 21, 433-441.

Rier, S. E., Turner, W. E., Martin, D. C., Morris, R., Lucier, G. W., and Clark, G. C. (2001). Serum levels of TCDD and dioxin-like chemicals in Rhesus monkeys chronically exposed to dioxin: correlation of increased serum PCB levels with endometriosis. *Toxicol Sci* 59, 147-159.

Ruoslahti, E. (2000) Semin Cancer Biol 10, 435-42.

Ruoslahti, E. 2002. Drug targeting to specific vascular sites. *Drug Discov Today* 7:1138-1143.

Sensky, T. E., and Liu, D. T. 1980. Endometriosis: associations with menorrhagia, infertility and oral contraceptives. *Int J Gynaecol Obstet* 17:573-576.

Shampson, J. A. 1940. The development of the implantation theory for the origin of peritoneal endometriosis. *Am. J. Obstet. Gynecol.* 40:549-557.

Sherwin, J. R., Sharkey, A. M., Mihalyi, A., Simsa, P., Catalano, R. D., and D'Hooghe, T. M. 2008. Global gene analysis of late secretory phase, eutopic endometrium does not provide the basis for a minimally invasive test of endometriosis. *Hum Reprod* 23:1063-1068.

Smith, G. P. (1985) Science 228, 1315-7.

Stausbol-Gron, B., Wind, T., Kjaer, S., Kahns, L., Hansen, N. J., Kristensen, P., and Clark, B. F. 1996. A model phage display subtraction method with potential for analysis of differential gene expression. *FEBS Lett* 391:71-75.

Stavreus-Evers, A., Nikas, G., Sahlin, L., Eriksson, H., and Landgren, B. M. 2001. Formation of pinopodes in human endometrium is associated with the concentrations of progesterone and progesterone receptors. *Fertil Steril* 76:782-791.

Sugihara, K., Sugiyama, D., Byrne, J., Wolf, D. P., Lowitz, K. P., Kobayashi, Y., Kabir-Salmani, M., Nadano, D., Aoki, D., Nozawa, S., et al. 2007. Trophoblast cell activation by trophinin ligation is implicated in human embryo implantation. *Proc Natl Acad Sci USA* 104:3799-3804.

Thomas, E. J. & Campbell, I. G. (2000) Gynecol Obstet Invest 50 Suppl 1, 2-10.

Torchilin, V. P., Rammohan, R., Weissig, V., and Levchenko, T. S. 2001. TAT peptide on the surface of liposomes affords their efficient intracellular delivery even at low temperature and in the presence of metabolic inhibitors. *Proc Natl Acad Sci USA* 98:8786-8791.

Traish, A. M. & Wotiz, H. H. (1990) Endocrinology 127, 1167-75.

Van Ewijk, W., de Kruif, J., Germeraad, W. T., Berendes, P., Ropke, C., Platenburg, P. P., and Logtenberg, T. 1997. Subtractive isolation of phage-displayed single-chain antibodies to thymic stromal cells by using intact thymic fragments. *Proc Natl Acad Sci USA* 94:3903-3908.

Vercellini, P., Barbara, G., Abbiati, A., Somigliana, E., Vigano, P., and Fedele, L. (2009). Repetitive surgery for recurrent symptomatic endometriosis: what to do? *Eur J Obstet Gynecol Reprod Biol* 146, 15-21.

Vercellini, P., Frontino, G., De Giorgi, O., Pietropaolo, G., Pasin, R., and Crosignani, P. G. (2003). Continuous use of an oral contraceptive for endometriosis-associated recurrent dysmenorrhea that does not respond to a cyclic pill regimen. *Fertil Steril* 80, 560-563.

Vetter, A. E., Deachapunya, C., and O'Grady, S. M. 1997. Na absorption across endometrial epithelial cells is stimulated by cAMP-dependent activation of an inwardly rectifying K channel. *J Membr Biol* 160:119-126.

Vigano, P., Gaffuri, B., Somigliana, E., Busacca, M., Di Blasio, A. M. & Vignali, M. (1998) Mol Hum Reprod 4, 1150-6.

Vinatier, D., Orazi, G., Cosson, M., and Dufour, P. 2001. Theories of endometriosis. *Eur J Obstet Gynecol Reprod Biol* 96:21-34.

Wender, P. A., Mitchell, D. J., Pattabiraman, K., Pelkey, E. T., Steinman, L., and Rothbard, J. B. 2000. The design, synthesis, and evaluation of molecules that enable or enhance cellular uptake: peptoid molecular transporters. *Proc Natl Acad Sci USA* 97:13003-13008.

Zafrakas, M., Tarlatzis, B. C., Streichert, T., Pournaropoulos, F., Wolfle, U., Smeets, S. J., Wittek, B., Grimbizis, G., Brakenhoff, R. H., Pantel, K., et al. 2008. Genome-wide microarray gene expression, array-CGH analysis, and telomerase activity in advanced ovarian endometriosis: a high degree of differentiation rather than malignant potential. *Int J Mol Med* 21:335-344.

Zhang, J., Spring, H., and Schwab, M. 2001. Neuroblastoma tumor cell-binding peptides identified through random peptide phage display. *Cancer Lett* 171:153-164.

We claim:

1. A composition comprising a peptide, wherein the peptide comprises an endosome escape signal, an effector molecule, and a targeting peptide,
    wherein the endosome escape signal has the sequence HLAHLAH (SEQ ID NO:37), HLAHLAHH (amino acids 1 to 8 of SEQ ID NO:38), HLAHLAHHL (amino acids 1 to 9 of SEQ ID NO:38), HLAHLAHHLA (amino acids 1 to 10 of SEQ ID NO:38), HLAHLAHHLAH (amino acids 1 to 11 of SEQ ID NO:38), HLAHLAHHLAHL (amino acids 1 to 12 of SEQ ID NO:38), HLAHLAHHLAHLA (amino acids 1 to 13 of SEQ ID NO:38), HLAHLAHHLAHLAH (amino acids 1 to 14 of SEQ ID NO:38), or HLAHLAHHLAHLAHHLAH (SEQ ID NO:38); and
    wherein the effector molecule has the sequence KLAKLAK (SEQ ID NO:39), (KLAKLAK)$_2$ (SEQ ID NO:26), KLAKLAKK (amino acids 1 to 8 of SEQ ID NO:40), KLAKLAKKL (amino acids 1 to 9 of SEQ ID NO:40), KLAKLAKKLA (amino acids 1 to 10 of SEQ ID NO:40), KLAKLAKKLAK (amino acids 1 to 11 of SEQ ID NO:40), KLAKLAKKLAKL (amino acids 1 to 12 of SEQ ID NO:40), KLAKLAKKLAKLA (amino acids 1 to 13 of SEQ ID NO:40), KLAKLAKKLAKLAK (amino acids 1 to 14 of SEQ ID NO:40), or KLAKLAKKLAKLAKKLAK (SEQ ID NO:40).

2. The composition of claim 1, wherein the peptide has the formula $X_7$-$X_8$-$X_9$, $X_8$-$X_7$-$X_9$, $X_7$-$X_9$-$X_8$, $X_8$-$X_9$-$X_7$, $X_9$-$X_7$-$X_8$, or $X_9$-$X_8$-$X_7$, wherein $X_7$ is the effector molecule, $X_8$ is the endosome escape signal, and $X_9$ is the targeting peptide.

3. The composition of claim 2, wherein the endosome escape signal has the sequence HLAHLAHHLAH (amino acids 1 to 11 of SEQ ID NO:38), HLAHLAHHLAHL (amino acids 1 to 12 of SEQ ID NO:38), HLAHLAHHLAHLA (amino acids 1 to 13 of SEQ ID NO:38), HLAHLAHHLAHLAH (amino acids 1 to 14 of SEQ ID NO:38), or HLAHLAHHLAHLAHHLAH (SEQ ID NO:38).

4. The composition of claim 1, wherein the targeting peptide comprises the amino acid sequence set forth in SEQ ID NO:1, 2, 3 or 4.

5. A composition comprising an endosome escape signal and a targeting peptide that selectively binds an endometriosis cell, wherein the endosome escape peptide comprises HLAHLAHH (amino acids 1 to 8 of SEQ ID NO:38), HLAHLAHHL (amino acids 1 to 9 of SEQ ID NO:38), HLAHLAHHLA (amino acids 1 to 10 of SEQ ID NO:38), HLAHLAHHLAH (amino acids 1 to 11 of SEQ ID NO:38), HLAHLAHHLAHL (amino acids 1 to 12 of SEQ ID NO:38), HLAHLAHHLAHLA (amino acids 1 to 13 of SEQ ID NO:38), or HLAHLAHHLAHLAH (amino acids 1 to 14 of SEQ ID NO:38).

6. The composition of claim 5, wherein the endosome escape peptide forms an alpha helix under acidic conditions.

7. The composition of claim 5, wherein the endosome escape peptide comprises the sequence HLAHLAH (SEQ ID NO:37).

8. The composition of claim 5, wherein the endosome escape peptide comprises HLAHLAHHLAH (amino acids 1 to 11 of SEQ ID NO:38), HLAHLAHHLAHL (amino acids 1 to 12 of SEQ ID NO:38), HLAHLAHHLAHLA (amino acids 1 to 13 of SEQ ID NO:38), or HLAHLAHHLAHLAH (amino acids 1 to 14 of SEQ ID NO:38).

9. The composition of claim 5, wherein the endosome escape peptide comprises two or more HLAHLAH sequences (SEQ ID NO:37).

10. The composition of claim 9, wherein the endosome escape peptide comprises the sequence HLAHLAHHLAHLAHHLAH (SEQ ID NO:38).

11. The composition of claim 5, wherein the targeting peptide binds to cyclic nucleotide-gated channel beta 3 (CNGB3).

12. The composition of claim 5, wherein the targeting peptide binds to the amino acid sequence SEQ ID NO:32.

13. The composition of claim 5, wherein the targeting peptide comprises the amino acid sequence set forth in SEQ ID NO:1.

14. The composition of claim 5, wherein the targeting peptide comprises the amino acid sequence set forth in SEQ ID NO:2, 3 or 4.

15. The composition of claim 5 further comprising an effector molecule.

16. The composition of claim 15, wherein the effector molecule is a peptide, apoptosis-inducing compound, apoptosis-inducing peptide, small molecule, pharmaceutical drug, toxin, fatty acid, detectable marker, conjugating tag, nanoshell, or enzyme.

17. The composition of claim 5, wherein the effector molecule is an apoptosis-inducing peptide comprising the sequence KLAKLAK (SEQ ID NO:39).

18. The composition of claim 17, wherein the effector molecule comprises KLAKLAKK (amino acids 1 to 8 of SEQ ID NO:40), KLAKLAKKL (amino acids 1 to 9 of SEQ ID NO:40), KLAKLAKKLA (amino acids 1 to 10 of SEQ ID NO:40), KLAKLAKKLAK (amino acids 1 to 11 of SEQ ID NO:40), KLAKLAKKLAKL (amino acids 1 to 12 of SEQ ID NO:40), KLAKLAKKLAKLA (amino acids 1 to 13 of SEQ ID NO:40), or KLAKLAKKLAKLAK (amino acids 1 to 14 of SEQ ID NO:40).

19. The composition of claim 17, wherein the apoptosis-inducing peptide comprises two or more KLAKLAK sequences (SEQ ID NO:39).

20. The composition of claim 17, wherein the apoptosis-inducing peptide comprises the sequence KLAKLAKKLAKLAK (SEQ ID NO:40).

21. The composition of claim 17, wherein the apoptosis-inducing peptide comprises (KLAKLAK)$_2$ (SEQ ID NO:26).

22. The composition of claim 5, wherein the composition comprises two peptides, wherein the first peptide comprises the endosome escape signal and the targeting peptide, and wherein the second peptide comprises the effector molecule and a second targeting peptide.

23. The composition of claim 1, wherein the targeting peptide comprises at least 9 amino acids, wherein the targeting peptide has at least 70% sequence identity with SEQ ID NO:3.

24. The composition of claim 1, wherein the targeting peptide has at least 70% sequence identity to the amino acid sequence set forth in SEQ ID NO:2, 3, or 4.

25. The composition of claim 1, wherein any variation of the targeting peptide from SEQ ID NO:3 is a conservative amino acid substitution.

26. The composition of claim 1, wherein any variation of the targeting peptide from SEQ ID NO:2 or 4 is a conservative amino acid substitution.

27. The composition of claim 1, further comprising a progestational agent.

28. The composition of claim 1, further comprising a Gonadotropin-releasing hormone (GnRH), GnRH analog, or GnRH agonist.

29. The composition of claim 1, further comprising an aromatase inhibitor.

30. The composition of claim 1, further comprising a narcotic.

31. The composition of claim 1, further comprising a non-steroidal anti-inflammatory drug (NSAID).

32. The composition of claim 1, further comprising a pharmaceutically acceptable carrier.

33. A composition comprising an endosome escape signal and a targeting peptide that selectively binds a cell or tissue of interest, wherein the endosome escape signal comprises an endosome escape peptide, wherein the endosome escape peptide comprises two or more units of the sequence $HX_1X_2HX_3X_4H$, wherein $X_1$, $X_2$, $X_3$, and $X_4$ are each independently leucine, alanine, valine, or isoleucine.

34. The composition of claim 33, wherein the endosome escape peptide comprises two or more units of the sequence $HX_1X_2HX_3X_4H$ followed by one unit of the sequence $HX_5X_6H$, wherein $X_1$, $X_2$, $X_3$, $X_4$, $X_5$, and $X_6$ are each independently leucine, alanine, valine, or isoleucine.

35. The composition of claim 33, wherein one of $X_1$, and $X_2$, is alanine or valine and the other is leucine or isoleucine, one of $X_3$, and $X_4$ is alanine or valine and the other is leucine or isoleucine, and one of $X_5$, and $X_6$ is alanine or valine and the other is leucine or isoleucine.

36. The composition of claim 33, wherein one of $X_1$, and $X_2$, is alanine and the other is leucine, one of $X_3$, and $X_4$ is alanine and the other is leucine, and one of $X_5$, and $X_6$ is alanine and the other is leucine.

37. The composition of claim 33, wherein the endo some escape peptide comprises two or more HLAHLAH sequences (SEQ ID NO:37).

38. The composition of claim 37, wherein the endosome escape peptide comprises the sequence HLAHLAH-HLAHLAHHLAH (SEQ ID NO:38).

39. A method comprising administering to a subject a composition of claim 1.

40. The method of claim 39, wherein the subject comprises a cell, wherein the cell is an endometriosis cell.

41. An isolated nucleic acid comprising a nucleic acid sequence encoding the peptide of claim 1.

42. A method comprising administering to a subject the nucleic acid of claim 41.

43. The method of claim 42, wherein the subject comprises a cell, wherein the cell is an endometriosis cell.

44. The method of claim 42, wherein the nucleic acid is expressed in a cell, wherein the nucleic acid is administered to the subject by administering the cell to the subject.

45. The method of claim 44, wherein the cell is a cell from the subject, wherein the nucleic acid is introduced to the cell ex vivo.

46. A peptide comprising two or more HLAHLAH sequences (SEQ ID NO:37).

47. The peptide of claim 46 comprising the sequence HLAHLAHHLAHLAHHLAH (SEQ ID NO:38).

48. The composition of claim 1, wherein the targeting peptide is an antibody specific for the cyclic nucleotide-gated channel beta 3 (CNGB3).

49. The composition of claim 48, wherein the antibody is specific for an epitope comprising the amino acid sequence SEQ ID NO:32.

50. A method comprising administering to a subject the composition of claim 48.

51. The method of claim 50, wherein the subject comprises a cell, wherein the cell is an endometriosis cell.

\* \* \* \* \*